United States Patent
Goodenowe

(10) Patent No.: US 10,123,989 B2
(45) Date of Patent: *Nov. 13, 2018

(54) METHOD OF LOWERING CHOLESTEROL

(71) Applicant: MED-LIFE DISCOVERIES LP, Saskatoon (CA)

(72) Inventor: Dayan Burke Goodenowe, Saskatoon (CA)

(73) Assignee: Med-Life Discoveries LP, Saskatoon, Saskatchewan (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/349,831

(22) Filed: Nov. 11, 2016

(65) Prior Publication Data

US 2017/0056363 A1    Mar. 2, 2017

Related U.S. Application Data

(63) Continuation of application No. 14/674,705, filed on Mar. 31, 2015, now Pat. No. 9,517,222, which is a continuation of application No. 12/090,342, filed as application No. PCT/CA2007/001472 on Aug. 27, 2007, now Pat. No. 9,034,923.

(60) Provisional application No. 60/888,883, filed on Feb. 8, 2007.

(51) Int. Cl.
  *A61K 31/232* (2006.01)
  *A61K 31/661* (2006.01)
  *A61K 31/6615* (2006.01)
(52) U.S. Cl.
  CPC .......... *A61K 31/232* (2013.01); *A61K 31/661* (2013.01); *A61K 31/6615* (2013.01)

(58) Field of Classification Search
  CPC . A61K 31/232; A61K 31/661; A61K 31/6615
  See application file for complete search history.

(56) References Cited

U.S. PATENT DOCUMENTS

| 5,731,354 | A | 3/1998 | Pruss |
| 5,759,585 | A | 6/1998 | Forgeot |
| 6,177,476 | B1 | 1/2001 | Peterson et al. |
| 6,835,750 | B1 | 12/2004 | Henderson |

(Continued)

FOREIGN PATENT DOCUMENTS

| EP | 2123281 A1 | 11/2009 |
| JP | 2007-33410 A | 2/2007 |

(Continued)

OTHER PUBLICATIONS

Chen et al., "Changes of Erythrocyte and Platelet Membrane Lipid Pattern in Different Subtypes of Dementia," Chin. Med. 1 78:771-773 (1998).

(Continued)

*Primary Examiner* — Angela C Brown-Pettigrew
(74) *Attorney, Agent, or Firm* — LeClairRyan PLLC

(57) ABSTRACT

The present invention relates to the method of lowering cholesterol in a patient in need thereof by administering to said patient a therapeutic effective amount of a compound selected from the group consisting of 1-alkyl, 2-acyl-glyceraldehyde-3-phosphate (G3P), 1-alkyl, 2-acyl glycerol and 1-alkyl, 2-acyl-glycerylphosphatidylethanolamine (GPE) or a pharmaceutically acceptable salt thereof.

3 Claims, 31 Drawing Sheets

| GLYCERYL BACKBONE | sn-2/R2 PtdEt/PLASMANYL/PLASMENYL |
|---|---|
| sn-1 CH$_2$-R1<br>sn-2 CH-R2<br>sn-3 CH$_2$-R3 | O-C(O)-C17H35 (18:0)<br>O-C(O)-C17H33 (18:1)<br>O-C(O)-C17H31 (18:2)<br>O-C(O)-C19H31 (20:4)<br>O-C(O)-C21H35 (22:4)<br>O-C(O)-C21H31 (22:6) |
| sn-1/R1<br>PtdEt<br>O-C(O)-C15H31 (16:0)<br>O-C(O)-C17H35 (18:0) | sn-3/R3<br>PtdEt/PLASMANYL/PLASMENYL<br>O-P(O)-O-C2H4-NH2<br>   OH |
| PLASMANYL<br>O-CH2-CH2-C14H29 (16:0)<br>O-CH2-CH2-C16H33 (18:0) | EXAMPLE<br>CH$_2$-O-CH=CH-C16H33<br>CH-O-C(O)-C21H31<br>CH$_2$-O-P(O)-O-C2H4-NH2<br>         OH<br>[PLASMENYL (18:0/22:6)] |
| PLASMENYL<br>O-CH=CH-C14H29 (16:0)<br>O-CH=CH-C16H33 (18:0) | |

(56) References Cited

U.S. PATENT DOCUMENTS

| | | |
|---|---|---|
| 7,349,809 B2 | 3/2008 | Goodenowe |
| 2003/0225035 A1 | 12/2003 | Harats-Dror |
| 2004/0191294 A1 | 9/2004 | Ramaprasad et al. |
| 2012/0129934 A1 | 5/2012 | Goodenowe |

FOREIGN PATENT DOCUMENTS

| | | | |
|---|---|---|---|
| WO | 2003081506 A2 | 10/2003 | |
| WO | WO2007002285 | * 1/2007 | ............ A61K 48/00 |
| WO | 2007030928 A2 | 3/2007 | |
| WO | 2007030948 A1 | 3/2007 | |
| WO | 2007/098585 A1 | 9/2007 | |
| WO | 2007137410 A1 | 12/2007 | |

OTHER PUBLICATIONS

Chen et al., "Rheologic Determinant Changes of Erythrocytes in Binswanger's Disease," Chin. Med. J. (Taipei) 76:76-85 (1999) (Abstract in English).

Maeba, "Antioxidative Effect of Plasmalogens," Oleo Science 2(1):27-36 (2002) (Abstract in English).

Puglielli et al., "Alzheimer's Disease: The Cholesterol Connection," Nat. Neurosci. 6(4):345-351 (2003).

Scarpini et al., "Treatement of Alzheimer's Disease: Current Status and New Perspectives," Lancet Neurol. 2:539-547 (2003).

Zhang et al., "Free Fatty Acids, Neutral Glycerides, and Phosphoglycerides in Transient Focal Cerebral Ischemia," J. Neurochem. 64(4):1688-1695 (1995).

European Search Report for European Patent Application No. 13160192 dated Aug. 23, 2013.

Gorgas et al., "The Ether Lipid-Deficient Mouse: Tracking Down Plasmalogen Functions," Biochimica et Biophysica Acta 1763:1511-1526 (2006).

Brites et al., "Funtions and Biosynthesis of Plasmalogens in Health and Disease," Biochimica et Biophysica Acta 1636:219-231 (2004).

Munn et al., "Deficiency in Ethanolamine Plasmalogen Leads to Altered Cholesterol Transport," J. Lipid Res. 44:182-192 (2003).

Urano et al., "Oxidative Injury of Synapse and Alteration of Antioxidative Defense Systems in Rats, and its Prevention by Vitamin E," Eur. J. Biochem. 245:64-70 (1997).

Das et al., "Dietary Ether Lipid Incorporation into Tissue Plasmalogens of Humans and Rodents," Lipids 27(6):401-405 (1992).

Hermetter et al., "Ether Lipids: Biochemical and Biomedical Aspects," Ether Lipids:Chemistry and Biology (Academic Press, New York) Chapter 22 pp. 260-273 (1983).

Paltauf, "Ether Lipids in Biomembranes," Chem. Phys. Lipids 74:101-139 (1994).

Davis, "Oxidative Mechanisms in Beta-Amyloid Cytotoxicity," Neurodegeneration 5:441-444 (1996).

Favreliere et al., "Age-related Changes in Ethanolamine Glycerophospholipid Fatty Acid Levels in Rat Frontal Cortex and Hippocampus," Neurobiol. Aging 21:653-660 (2000).

Han et al., "Plasmalogen Deficiency in Early Alzheimer's Disease Subjects and in Animal Models: Molecular characterization using Electrospray Ionization Mass Spectrometry," J. Neurochem. 77:1168-1180 (2001).

Han, "Lipid Alterations in the Earliest Clinically Recognizable Stage of Alzheimer's Disease: Implication of the Role of Lipids in the Pathogenesis of Alzheimer's Disease," Curr. Alzheimer Res. 2:65-77 (2005).

Janssen et al., "Neuronal Migration Depends on Intact Peroxisomal Function in Brain and in Extraneuronal Tissues," J. Neurosci. 23(30):9732-9741 (2003).

Legakis et al., "Peroxisome Senescence in Human Fibroblasts," Mol. Biol. Cell 13:4243-4255 (2002).

Perichon et al., "Peroxisomal Beta-Oxidation Activity and Catalase Activity During Development and Aging in Mouse Liver," Biochimie 77:288-293 (1995).

Perichon et al., "The Role of Peroxisomes in Aging," Cell. Mol. Life Sci. 54:641-652 (1998).

Pratico et al., "Increased Lipid Peroxidation Precedes Amyloid Plaque Formation in an Animal Model of Alzheimer Amyloidosis," J. Neurosci. 21(12):4183-4187 (2001).

Andre et al., "Plasmalogen Metabolism-Related Enzymes in Rat Brain During Aging: Influence of n-3 Fatty Acid Intake," Biochimie 88:103-111 (2006).

Bourre et al., "Delta-6 Desaturation of Alpha-Linolenic Acid in Brain and Liver During Development and Aging in the Mouse," Neurosci. Lett. 141:65-68 (1992).

Brosche et al., "Erythrocyte Membrane Changes Associated with Nutrition and Aging—The Role of Plasmalogens," Arch. Gerontol. Geriatr. 9:291-296 (1989).

Burns et al., "White Matter Lesions are Prevalent but Differentially Related with Cognition in Aging and Early Alzheimer Disease," Arch. Neural. 62:1870-1876 (2005).

Butterfield et al., "Lipid Peroxidation and Protein Oxidation in Alzheimer's Disease Brain: Potential Causes and Consequences Involving Amyloid Beta-Peptide-Associated Free Radical Oxidative Stress," Free Rad. Biol. & Med. 32 (11):1050-1060 (2002).

Christen, "Oxidative Stress and Alzheimer Disease," Am. J. Clin. Nutr. 71:621S-629S (2000).

Reiss et al., "Delayed Oxidative Degradation of Polyunsaturated Diacyl Phospholipids in Presence of Plasmalogen Phospholipids in vitro," Biochem. J. 323:807-814 (1997).

Scott et al., "Membrane Docosahexaenoate is Supplied to the Developing Brain and Retina by the Liver," Proc. Nat. Acad. Sci. U.S.A. 86:2903-2907 (1989).

Weisser et al., "Dramatic Increase of Alpha-Hydroxyaldehydes Derived from Plasmalogens in the Aged Human Brain," Chem. Phys. Lipids 90:135-142 (1997).

Wells et al., "Neural Membrane Phospholipids in Alzheimer Disease," Neurochem. Res. 20(11):1329-1333 (1995).

Zoeller et al., "Isolation of Animal Cell Mutants Deficient in Plasmalogen Biosynthesis and Peroxisome Assembly," Proc. Nat. Acad. Sci. U.S.A. 83:5170-5174 (1986).

Zoeller et al., "Increasing Plasmalogen Levels Protects Human Endothelial Cells During Hypoxia," Am. J. Physiol. Heart Circ. Physiol. 283:H671-H679 (2002).

Ivy, "Effect of Pyruvate and Dihydroxyacetone on Metabolism and Aerobic Endurance Capacity," Med. Sci. Sports Exerc. 30(6):837-43 (1998) (Abstract).

Cheng et al., "Specificity and Potential Mechanism of Sulfatide Deficiency in Alzheimer's Disease: An Electrospray Ionization Mass Spectrometric Study," Cell Mol. Biol. 49:809-818 (2003).

Martinez, "Severe Deficiency of Docosahexaenoic Acid in Peroxisomal Disorders: A Defect of Delta 4 Desaturation?" Neurol. 40:1292-1298 (1990).

Nagan et al., "Plasmalogens: Biosynthesis and Functions," Progress in Lipid Research 40:199-229 (2001).

Ellison et al., "Phosphoethanolamine and Ethanolamine are Decreased in Alzheimer's Disease and Huntington's Disease," Brain Research 417:389-392 (1987).

Nitsch et al., "Evidence for a Membrane Defect in Alzheimer Disease Brain," Proceedings of the National Academy of Science 89:1671-1675 (1992).

Ginsberg et al., "Disease and Anatomic Specificity of Ethanolamine Plasmalogen Deficiency in Alzheimer's Disease Brain," Brain Research 698:223-226 (1995).

Marshall et al., "Effects of Ethanolamine (ETN) Administration on ETN and Choline (CH) Levels in Plasma, Brain Extracellular Fluid (ECF) and Brain Tissue, and on Brain Phospholipid Levels in Rats: An In Vivo Study," Neuroscience Research Communications 18(2):87-96 (1996).

Ginsberg et al., "Membrane Instability, Plasmalogen Content, and Alzheimer's Disease," Journal of Neurochemistry 70:2533-2538 (1998).

Guan et al., "Decrease and Structural Modifications of Phosphatidylethanolamine Plasmalogen in the Brain with Alzheimer Disease," Journal of Neuropathology and Experimental Neurology 58:740-747 (1999).

(56) References Cited

OTHER PUBLICATIONS

Pettegrew et al., "Brain Membrane Phospholipid Alterations in Alzheimer's Disease," Neurochemical Research 26:771-782 (2001).
Gruger et al., "Fatty Acid Composition," In Fish Oils: Their Chemistry, Technology, Stability, Nutritional Properties and Uses. M.E. Stansby (ed), pp. 3-30, 1967.

* cited by examiner

| | |
|---|---|
| GLYCERYL BACKBONE<br><br>sn-1 CH$_2$-R1<br>sn-2 CH-R2<br>sn-3 CH$_2$-R3 | sn-2/R2<br>PtdEt/PLASMANYL/PLASMENYL<br><br>O-C(O)-C17H35   (18:0)<br>O-C(O)-C17H33   (18:1)<br>O-C(O)-C17H31   (18:2)<br>O-C(O)-C19H31   (20:4)<br>O-C(O)-C21H35   (22:4)<br>O-C(O)-C21H31   (22:6) |
| sn-1/R1<br><br>PtdEt<br><br>O-C(O)-C15H31   (16:0)<br>O-C(O)-C17H35   (18:0)<br><br>PLASMANYL<br><br>O-CH2-CH2-C14H29   (16:0)<br>O-CH2-CH2-C16H33   (18:0)<br><br>PLASMENYL<br><br>O-CH=CH-C14H29   (16:0)<br>O-CH=CH-C16H33   (18:0) | sn-3/R3<br>PtdEt/PLASMANYL/PLASMENYL<br><br>O-P(O)-O-C2H4-NH2<br>   \|<br>   OH<br><br>EXAMPLE<br><br>CH$_2$-O-CH=CH-C16H33<br>CH-O-C(O)-C21H31<br>CH$_2$-O-P(O)-O-C2H4-NH2<br>         \|<br>         OH<br><br>[PLASMENYL (18:0/22:6)] |

*FIG. 1*

A. 1-O-1'-(Z)-octadecenyl-2-arachidoyl-sn-glycero-3-phosphoethanolamine (1)
HRAPCI-MS $m/z$: MEASURED 750.5482. ([M − H]⁻, calcd. 750.5477 FOR $C_{43}H_{77}NO_7P$).
MS/MS $m/z$ (RELATIVE INTENSITY): 750 ([M − H]⁻, 25%), 482 (1%), 464 (12%),
446 (5%), 329 (8%), 303 (100%), 259 (12%), 205 (8%), 140 (8%).

FRAGMENT ANALYSIS:

| $m/z$ | FORMULA | MOLECULAR FRAGMENT | FRAGMENT LOSS |
|---|---|---|---|
| 750 | $C_{43}H_{77}NO_7P$ | $H_2N\sim O-P(O)(O^-)-O-\text{glycerol}-O-C_{19}H_{31}, O-C_{16}H_{33}$ | $H^+$ |
| 482 | $C_{45}H_{41}NO_6P$ | $H_2N\sim O-P(O)(O^-)-O-\text{glycerol}-O-C_{19}H_{31}$ | $HO\sim C_{16}H_{33}$ |
| 464 | $C_{23}H_{47}NO_6P$ | $H_2N\sim O-P(O)(O^-)-O-CH(OH)-CH_2-O-C_{16}H_{33}$ | $O\sim C_{19}H_{31}$ |
| 462 | $C_{23}H_{45}NO_6P$ | $H_2N\sim O-P(O)(O^-)-O-CH(OH)-CH_2-O-C_{16}H_{33}$ | $O\sim C_{19}H_{31}$ |
| 444 | $C_{23}H_{43}NO_5P$ | $H_2N\sim O-P(O)(O^-)-O-CH=CH-O-C_{16}H_{33}$ | $462-H_2O$ |
| 436 | $C_{21}H_{43}NO_6P$ | $H_2N\sim O-P(O)(O^-)-O-CH(OH)-CH_2-O-C_{14}H_{29}$ | $464-C_2H_8$ |
| 331 | $C_{22}H_{35}O_2$ | $-O-C(O)-C_{19}H_{31}$ | i. $-O\sim C_{16}H_{33}$<br>ii. $H_2N\sim O-P(O)(OH)-OH$ |
| 303 | $C_{20}H_{31}O_2$ | $O\sim C_{19}H_{31}, O^-$ | $H_2N\sim O-P(O)(O^-)-O-CH_2-CH(O)-CH_2-O\sim C_{16}H_{33}$ |
| 259 | $C_{19}H_{31}$ | (alkyl chain) | $303-CO_2$ |
| 205 | $C_7H_{10}O_5P$ | $\sim O-P(O)(O^-)-O\sim O\sim$ | $464-H_2O, C_{16}H_{32}$ & $NH_3$ |

*FIG. 24A*

PROPOSED STRUCTURE:

B. 1-O-1'-(Z)-hexadecenyl-2-linoleyl-*sn*-glycero-3-phosphoethanolamine (2)
HRAPCI-MS *m/z*: MEASURED 698.5125 ([M − H]⁻, calcd. 698.5130 FOR $C_{39}H_{73}NO_7P$).
MS/MS *m/z* (RELATIVE INTENSITY): 698 ([M − H]⁻, 8%), 536 (4%), 279 (100%), 255 (15%), 119 (10%).

FRAGMENT ANALYSIS:

| m/z | FORMULA | MOLECULAR FRAGMENT | FRAGMENT LOSS |
|---|---|---|---|
| 698 | $C_{39}H_{73}NO_7P$ | | $H^+$ |
| 458 | $C_{23}H_{41}NO_6P$ | | $HO{\sim}C_{14}H_{29}$ |
| 436 | $C_{21}H_{43}NO_6P$ | | $O{\sim}C_{17}H_{31}$ |
| 418 | $C_{21}H_{41}NO_5P$ | | $436-H_2O$ |
| 279 | $C_{18}H_{31}O_2$ | | |
| 255 | $C_7H_{15}NO_5P^-$ | | $436-C_2H_5$ & |

PROPOSED STRUCTURE:

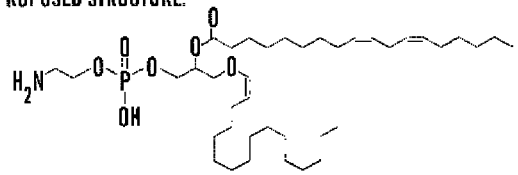

C. 1-O-1'-(Z)-hexadecenyl-2-arachidoyl-sn-glycero-3-phosphoethanolamine (3)
HRAPCI-MS m/z : MEASURED 722.5124 ([M – H]⁻, calcd. 722.5130 FOR $C_{41}H_{73}NO_7P$).
MS/MS m/z (RELATIVE INTENSITY): 722 ([M – H]⁻,12%), 482 (1%), 436 (15%),
418 (6%), 303 (100%), 279 (6%), 259 (15%), 255 (10%), 205 (4%), 140 (5%).

FRAGMENT ANALYSIS:

| m/z | FORMULA | MOLECULAR FRAGMENT | FRAGMENT LOSS |
|---|---|---|---|
| 722 | $C_{41}H_{72}NO_7P$ | 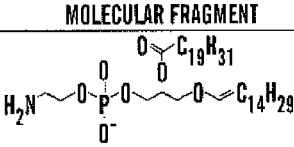 | H⁺ |
| 482 | $C_{25}H_{41}NO_6P$ | 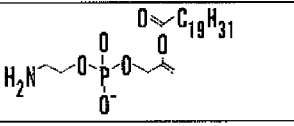 | HO~C₁₄H₂₉ |
| 466 | $C_{24}H_{37}NO_6P$ | 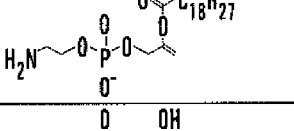 | 482−CH₄ |
| 436 | $C_{21}H_{43}NO_6P$ | 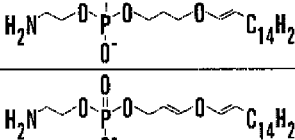 | O~C₁₉H₃₁ |
| 418 | $C_{21}H_{41}NO_5P$ | 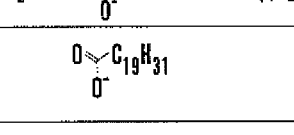 | O~C₁₉H₃₁ / O⁻ |
| 303 | $C_{20}H_{31}O_2$ | 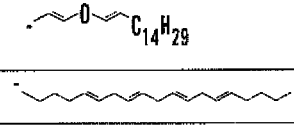 | 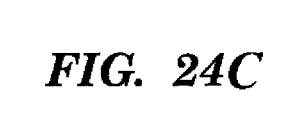 |
| 279 | $C_{19}H_{35}O$ | ~O~C₁₄H₂₉ | 418−H₂N~O-P-OH |
| 259 | $C_{19}H_{31}$ |  | 303−CO₂ |

*FIG. 24C*

| m/z | FORMULA | MOLECULAR FRAGMENT | FRAGMENT LOSS |
|---|---|---|---|
| 255 | $C_{15}H_{27}O_3$ |  | 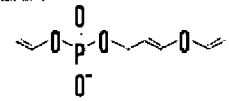 |
| 205 | $C_7H_{10}O_5P$ | 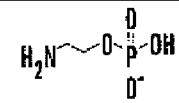 | $418-C_{14}H_{30}$ & $NH_3$ |
| 140 | $C_2H_7NO_4P$ | 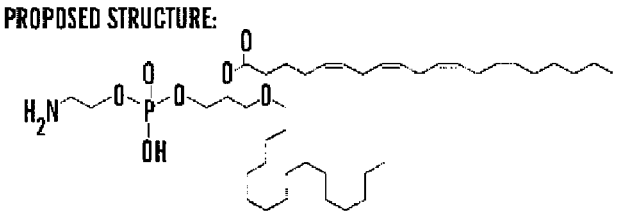 | |
PROPOSED STRUCTURE:
FIG. 24D

METHOD OF LOWERING CHOLESTEROL

This is a continuation of U.S. patent application Ser. No. 14/674,705, filed Mar. 31, 2015, which is a continuation of U.S. patent application Ser. No. 12/090,342, now U.S. Pat. No. 9,034,923, issued May 19, 2015, which is a national stage application under 35 USC § 371 of PCT/CA2007/001472, filed Aug. 27, 2007, which claims the priority benefit of U.S. Provisional Patent Application Ser. No. 60/888,883, filed Feb. 8, 2007.

FIELD OF THE INVENTION

The present invention relates to the diagnosis, risk assessment, prevention, and treatment of Senile Dementia of the Alzheimer's Type (SDAT). More specifically the present invention relates to the measurement of ethanolamine phospholipids in human serum. Further, the invention relates to the diagnosis of various stages of SDAT, the early detection and prevention of SDAT symptoms, the treatment of SDAT, the differential diagnosis of non-SDAT dementia, and the identification of molecular targets for which chemical or biological treatments can be designed for the therapeutic intervention of SDAT. The present invention also relates to methods of using a molecular diagnostic assay to direct and select the appropriate therapeutic intervention for subjects suffering from dementia. Further, this invention relates to small molecules or metabolites that are found to have significantly different abundances between persons with a clinical manifestation of SDAT and normal, non-demented patients.

BACKGROUND OF THE INVENTION

The most severe consequence of the aging brain is dementia. The number of elderly people is increasing rapidly within our society and as a consequence, dementia is growing into a major health problem. It has been estimated that 25% of the population over the age of 65 have a form of dementia (1) and that the cumulative incidence of dementia in individuals living to the age of 95 is greater than 80% (2,3).

The clinical manifestation of dementia can result from neurodegeneration (e.g. Senile Dementia of the Alzheimer's Type (SDAT), dementia with Lewy bodies (DLB) and frontotemporal lobe dementia (FTLD)), vascular (e.g. multi-infarct dementia) or anoxic event (e.g. cardiac arrest), trauma to the brain (e.g. dementia pugilistica [boxer's dementia]), or exposure to an infectious (e.g. Creutzfeldt-Jakob Disease) or toxic agent (e.g. alcohol-induced dementia) (4). The fact that dementia can result from multiple diseases indicates that the biochemical mechanism(s) of dementia are separate and distinct from the individual disease pathologies. The metabolic basis for the specific cognitive impairments caused by or associated with these specific pathologies are currently unknown.

The differential diagnosis of the types and causes of dementia is not straightforward. A prospective study on the prevalence of SDAT in people over the age of 85 indicated more than half of the individuals with neuropathological criteria for SDAT were either non-demented or were incorrectly diagnosed with vascular dementia. As well, 35% of the clinically diagnosis SDAT subjects did not exhibit neuropathological features sufficient to support the diagnosis (5). Clearly, SDAT symptmology can arise from multiple pathological states that are often clinically indistinguishable. Therefore there is a tremendous need for non-invasive biochemical testing procedures that can accurately identify subjects with a particular neuropathology or increased risk of acquiring a specific neuropathology. SDAT is the most common type of dementia and the percentage of dementias that is SDAT increases with increasing age (2) making this form of dementia the most important one to be able to diagnose in living subjects accurately.

The diagnosis of SDAT ultimately requires demonstration of SDAT pathology, namely the presence of argyrophilic plaques (amyloid deposition) and neurofibrillary degeneration of neurons in the cortex and hippocampus. However, SDAT pathology is often found in the brains of older persons without dementia or mild cognitive impairment (MCI) and may be related to subtle changes in episodic memory (6, 7, 8). At this time, the best post-mortem correlate with dementia in Alzheimer's disease (AD) remains the selective loss/dysfunction of cholinergic projections from the N. basalis and septum to the cortex and hippocampus, respectively.

In SDAT, the cholinergic deficit is best reflected by up to 80% decreases in choline acetyltransferase (ChAT) activity in the neocortex and hippocampus (9, 10, 11, 12, 13). Data indicate that degeneration or dysfunction of cholinergic neurons in the basal forebrain is a defining characteristic of SDAT. Reductions in cortical ChAT activity, monitored via biopsy or in autopsy samples, correlate with the extent of intellectual impairment in SDAT patients, as monitored by the Mini-Mental State Examination (MMSE), an index of global cognitive function (9, 14, 15). In addition, these cortical cholinergic deficits have been found in patients examined within a year of onset of symptoms and cholinesterase inhibitors, which potentiate residual cholinergic transmission, slow the decline in executive memory functions in SDAT patients (16).

Detailed analyses revealed that cholinergic neurons were generally shrunken and dysfunctional, but not dead, except in late stage AD (13, 18-22). These neuronal phenotypic changes without frank neuronal degeneration occur early in cognitive decline (23). The persistence of shrunken basal forebrain cholinergic neurons in SDAT is similar to that seen in experimental studies of retrograde cellular degeneration in the N. basalis following axotomy (19). It is the applicant's hypothesis that due to the preservation of these magnocellular cholinergic neurons in shrunken form and the applicant's novel discovery of a systemic depletion of key ether lipid molecules that the cholinergic dysfunction in SDAT may be responsive to restorative therapy through pharmacological or supplementation strategies involving ether lipids.

Studies of ChAT levels in the N. basalis and cortex in the same autopsy samples have shown that in 50% of AD patients there is a marked loss of cortical ChAT with no reduction in N. basalis ChAT (13) suggesting abnormal axonal transport in SDAT. In this regard there are significant reductions in frontal (11.9%) and temporal (29.4%) white matter in SDAT autopsy samples compared to normal controls (24). Atrophy of the corpus callosum also is correlated with frontal executive dysfunction in AD patients (25). These observations have led to suggestions that white matter degeneration is an intrinsic component of SDAT (26, 27). Moreover, white matter losses in preclinical SDAT where cortical atrophy is not evident (28), indicate that axonal dysfunction precedes the cortical atrophy observed in clinically manifested SDAT. In fact, white matter lesions are prevalent in aging, in MCI and in early-stage SDAT prior to the development of dementia (29, 30). Again it is this information in combination with the applicant's novel discovery of a systemic depletion of key ether lipid molecules that has led the applicant to the novel hypothesis that the early white matter losses described is due to decreased synthesis of key ether lipid molecules and that this loss could be restored through supplementation of ether lipid molecules.

Lipids make up over 50% of the dry weight of the human brain. Of these lipids, over mol % are phospholipids, and of these phospholipids over 60% are phosphatidylethanolamine (PtdEt or PE) lipids. Ethanolamine phospholipids can be further differentiated based on their sn-1 configurations (either acyl, ether, or vinyl ether). The sn-2 position is typically acyl and the sn-3 position contains the phosphoethanolamine moiety. Therefore the three classes are described as either diacyl (PtdEt), alkyl-acyl (plasmanyl) or alkenyl-acyl (EtnPl). Forty to forty five percent of the ethanolamine phospholipid content is of the PtdEt type and 40-45% is of the EtnPl type, and 10-15% of the plasmanyl type (36).

In the central nervous system (CNS), EtnPls constitute over 80% of the PE content in non-neuronal brain membranes and over 60 mol % in neurons and synaptosomes (34). EntPls in white matter counterparts contain predominantly 18 carbon mono- and di-unsaturated fatty acids (oleic acid (OA, 18:1), linoleic acid (LA, 18:2) at sn-2; in contrast, EtnPls in gray matter contain predominantly longer chain polyunsaturated fatty acids (for example, arachidonic acid (AA, 20:4) and docosohexaenoic acid (DHA, 22:6)) (34). These differences result in different structural characteristics. A high percentage of 18:1/18:2 at sn-2 results in very compact and stable membrane conformations (40, 41), which is consistent with myelin sheath function, whereas a high percentage of AA and DHA results in the fluid membrane structure required for membrane fusion, transmembrane protein function, and intra-cellular-extra-cellular cholesterol trafficking.

The second critical role that EtnPls play in the CNS is as a key membrane antioxidant. The EtnPl vinyl ether bond acts is preferentially oxidized to form a saturated aldehyde and a 1-lyso, 2-acyl GPE. The preferential oxidation of the vinyl ether linkage preserves sn-2 fatty acids such as DHA and AA (42) that require essential dietary omega-3 and -6 fatty acids, whereas the O-alkyl ether can be re-synthesized in the cell. Oxidation of the vinyl ether bond, however, results in the irreversible turn-over of EtnPls that can only be restored through the re-synthesis of these ether lipids in the peroxisome.

The key point in plasmalogen biosynthesis is that the creation of the 1-O-alkyl bond occurs exclusively in peroxisomes by the enzyme alkyl-dihydroxy acetone phosphate (DHAP) synthase. Loss of function of this enzyme either through point mutations or due to general peroxisomal dysfunction results in a severe plasmalogen deficiency. The remaining key synthetic processes occur in the endoplasmic reticulum (ER) where the sn-2 position is acylated and phosphoethanolamine is added to the sn-3 position to create plasmanyl PE. The final step involves a plasmanyl-specific enzyme that desaturates the 1-O-alkyl ether to form EtnPl.

Pathologically, the formation of extracellular Aβ plaques is a hallmark of SDAT. At the biochemical level, detailed analyses of brain lipids have demonstrated a dramatic (40 mol %) decrease in EtnPl levels of white matter in early SDAT patients, with no further progression in these lipid losses (33-35). In contrast, there is a 10 mol % decrease in gray matter EtnPls in early SDAT which progresses to 30 mol % later in the disease process (34, 35).

Decreased levels of DHA and AA containing EtnPls in gray matter correlate with both dementia severity and Aβ load, however significant changes do not occur until the moderate stage of dementia (34). In contrast, significantly decreased levels of oleic acid (OA)- and linoleic acid (LA)-containing EtnPl in white matter are observed at all stages of dementia (CDR0.5-3.0) in all brain regions, which is consistent with the prevalence of white matter lesions in aging, MCI and pre-dementia SDAT (29, 30). This information supports the present invention that these CNS decreases are the result of a peripheral dysfunction in ether lipid synthesis and not entirely due to oxidative breakdown.

Direct incubation of oligodendrocytes with Aβ peptides selectively decreases plasmenyl PE content (45) and CNS plasmenyl PE decreases correlate with both the temporal and anatomical characteristics of Aβ accumulation animal models (33, 34, 46). Aβ accumulation is also known to directly induce oxidative stress (47-49) and oxidative stress can directly disrupt vesicular fusion, acetylcholine release, and synaptosomal PE content (50). Oxidative stress also preferentially oxidizes EtnPls vs. PtlEts (42, 51). Due to the sensitivity of EtnPls to oxidation, previous researchers have concluded that decreased EtnPls in SDAT tissue is due to increased oxidative stress. It is only through applicant's discovery that both EtnPls and plasmanyl PEs decrease in SDAT that this generally accepted theory is likely to be wrong. To the applicant's best knowledge, this is the first evidence that a systemic reduction in ether lipid synthesis is a causative factor in SDAT.

In both humans and in animal models of Aβ overproduction, an age-related trigger is required before these peptides begin to accumulate extracellularly as plaques. In humans, signs of Aβ accumulation start as early as age 40 in non-demented subjects and the prevalence increases with increasing age (53, 54). In mice, genetic conditions that produce 30 times the normal amount Aβ, still fail to result in accumulation until after 8 months of age; thereafter, Aβ begins to accumulate at an exponential rate and preferentially in cortex and hippocampus vs. cerebellum (55). Other animal models of Aβ accumulation show similar age profiles (56). Clearly, Aβ production and accumulation are separately regulated biological processes. The sporadic accumulation of Aβ peptides in SDAT has been linked to a disruption in normal APP processing due to increased membrane cholesterol levels (57). This is consistent with the fact that membrane cholesterol increases with age in both rats and humans (58) and that a high cholesterol diet can increase deposition of Aβ (59).

Although, peroxisomal function as a whole is known to decline with age (68) and appears to be critical for neuronal migration (69), the applicant is the first to link the timing of Aβ accumulation and increased lipid peroxidation (55) to decreased peroxisomal activity in mice (70). Peroxisomal proliferation can inhibit Aβ induced neurodegeneration (71) and preserve cognition in early SDAT (72). Peroxisomes consume between 10 and 30% of total cellular oxygen and generate over 30% of the $H_2O_2$. Catalase, the principal peroxisomal enzyme responsible for detoxifying $H_2O_2$, decreases in activity with age (73-75), and has been linked with increased lipid peroxidation (73). The decrease in catalase import and increased intracellular $H_2O_2$ has been linked to severely compromised peroxisomal targeting signals, as age increases (79). Decreased peroxisomal function leads to decreased synthesis of EtnPls and DHA (80, 81), two critical components of normal neuronal functioning, and to increased oxidative stress (79).

With respect to the membrane dysfunction and SDAT, there are well documented age-related decreases in the bioactivities of peroxisomal enzymes involved in the synthesis of plasmalogens and DHA. The two most abundant fatty acids at the sn-2 position of EtnPls in neurons are AA and DHA. AA is an n-6 fatty acid, derived from linoleic acid (18:2, n-6), whereas DHA is an n-3 fatty acid, derived from linolenic acid (18:3, n-3). DHA synthesis involves chain elongation and desaturation of 18:3 n-3 in the ER to 24:6 n-3 with the final step being β-oxidation to DHA in the peroxisome (76). Both DHAP synthase (77) and β-oxidase (75) exhibit decreased function with age. AA synthesis does not require peroxisomal β-oxidation. DHA- and AA-containing EtnPls are selectively decreased with age with DHA-EtnPls being decreased to a greater extent than AA-EtnPls (78).

While the brain contains all of the peroxisomal machinery to synthesize both DHA and EtnPls, studies have shown that DHA is produced and incorporated into phospholipids in the liver, then transported to the brain in this form via the serum. Only trace levels of newly synthesized DHA are found as free fatty acid or in triglycerides (82). This provides further evidence to support the applicant's hypothesis that decreased CNS EtnPls is due to a peripheral dysfunction in ether lipid synthesis and that supplementation of ether lipids will have a positive effect on CNS neuronal composition and function, especially in subjects shown to be deficient in these molecules.

There is thus a need for a diagnostic assay that exploits the biochemical alterations present in SDAT. There is also a need to treat subjects identified as having this biochemical alteration in such a way as to restore this biochemical alteration to normal levels. There is also a need to be able to make this identification as early as possible in the disease progression process as to have maximal benefit to the health of an individual at risk or in the early stages of SDAT.

SUMMARY OF THE INVENTION

The present invention relates to the diagnosis, risk assessment, prevention, and treatment of Senile Dementia of the Alzheimer's Type (SDAT). More specifically the present invention relates to the measurement of ethanolamine phospholipids in human serum. Subsets of these molecules have been found to be significantly altered in subjects with pathologically confirmed deposits of β-amyloid versus subjects without β-amyloid deposits and in subjects with a clinical manifestation of dementia consistent with a diagnosis of SDAT versus non-demented controls. Of particular interest are changes in ethanolamine phospholipids containing a vinyl ether linkage at the sn-1 position, commonly referred to as ethanolamine plasmalogens (EtnPls).

The present invention relates to small molecules or metabolites that are found to have significantly different abundances between persons with a clinical manifestation of SDAT and normal, non-demented patients. The present invention also relates to small molecules or metabolites that have significantly different abundances between persons with a neuropathological accumulation of amyloid-β and persons absent of such pathology. Decreased levels of these small molecules or metabolites may be indicative of a pre-dementia pathological state. Specifically, the present invention identifies specific ethanoloamine phospholipids that are significantly decreased in the serum of subjects suffering from SDAT. The present invention also relates to methods for diagnosing dementia and other neurological disorders.

The present invention discloses how subjects with SDAT may have metabolically compromised ethanolamine plasmalogen system and that this process can be monitored in serum.

The present invention discloses that a depletion in plasmanyl ethanolamine phospholipids and EtnPls is a causal factor in SDAT.

The present invention also discloses how subjects with SDAT have metabolically compromised ether lipid synthesis capabilities, and how this system can be corrected through the administration of metabolic precursors or peroxisomal proliferator receptor activator agonists.

Thus, the present invention is directed a method of treating a patient with SDAT by administering to said patient a therapeutically effective amount of a metabolic precursor of ethanolamine plasmalogen biosynthesis system or a peroxisomal proliferator receptor activator agonist.

The present invention discloses a novel method of diagnosing the presence of SDAT in a subject by measuring the levels of specific ethanoloamine phospholipids present in a serum sample taken from a subject of unknown disease status and comparing these levels to "normal" or SDAT reference levels and through this comparison arriving at either an SDAT positive or SDAT negative diagnosis.

The present invention discloses a novel method for identifying subjects that are at risk of developing SDAT by comparing serum levels of one or more than one metabolites from a test subject to average level of such metabolites in either a control or a SDAT population.

The present invention also discloses a novel method for identifying subjects at risk of developing SDAT by comparing a mathematically determined metabolite score from a test subject to the average of such score from either a normal or SDAT reference population.

The present invention further discloses a novel method for identifying subjects at risk of developing SDAT by comparing the ratio of one or more than one metabolite to an endogenous reference metabolite from a test subject to the average of such ration from either a normal or SDAT reference population.

A method is provided for the diagnosis of subjects afflicted with SDAT and/or for the differential diagnosis of subjects afflicted with SDAT versus subjects afflicted from other dementia such as frontotemporal lobe dementia (FTD) or dementia with Lewy bodies (DLB). Further, a method is provided that determines whether a subject who does not show any cognitive signs of SDAT has the early neuropathological features of the disease.

The methods of the present invention can be used for the following, wherein the specific "health-state" in this application refers to, but is not limited to SDAT:

1. diagnosing a given health-state, or risk for development of a health-state by determining the levels of any combination of metabolite features disclosed in the method;
2. diagnosing a given health-state, or risk for development of a health-state by determining any combination of serum ratios of any of metabolite features disclosed in the method;
3. treating positively diagnosed or at-risk individuals by administration of one or more of the metabolite features alone or in combination with other therapies including, but not limited to, chemotherapy and/or biological therapy;
4. treating positively diagnosed or at-risk individuals by administration of a chemical analog, metabolic precursor, or formulation of any or a subset of the metabolite features alone or in combination with other therapies including, but not limited to, chemotherapy and/or biological therapy;

5. targeting the metabolic pathway responsible for the feature set perturbation in effort to restore levels of the features to within normal range using any of the following: chemotherapy, biological therapy, dietary intervention, lifestyle intervention, or other method. For example, and without wishing to be limiting, subjects which test positive (i.e. low plasmalogens) may preferentially benefit from the use of peroxisome proliferation activating receptor (PPAR) agonists such as Avandia (rosiglitazone) whereas, subjects that test normal may preferentially benefit from drugs or therapies that may not be directly related plasmalogens synthesis or degradation such as cholesterol lowering therapies like 3-hydroxy-3-methylglutaryl conenzyme A (HMG-CoA) reductase inhibitors such as Lipitor (atorvastatin);
6. monitoring therapeutic treatment of a health-state, including drug, dietary or lifestyle effects;
7. pre-dementia longitudinal monitoring of individual subjects in order to create an individual-specific baseline that can be used for the early detection of SDAT-like metabolic changes;
8. screening of the general population for one or more health-state using any single or combination of features disclosed in the method.

The present invention discloses endogenous human metabolites that can be extracted from a serum sample and quantitatively analyzed. The results of such analyses can then be used as a diagnostic indicator of disease presence as well as disease severity.

The present invention provides a method for differentially diagnosing between SDAT dementia, non-SDAT dementia, and non-demented normal states, comprising the steps of: obtaining a serum sample from one or more than one patient with dementia introducing said sample into an analytical instrument capable of quantifying all or a subset of the metabolites listed in Table 2, or closely related entities; obtaining quantifying data for the metabolites; creating a database of said data; and comparing the data from the sample with reference data obtained from similarly analyzed samples collected from one or more than one non-demented normal subject(s). Demented subjects with decreased levels of metabolites are diagnosed as SDAT. Demented subjects with normal levels of metabolites are diagnosed as non-SDAT.

The present invention also provides a method for identifying cognitively normal individuals who are at risk of developing SDAT comprising: obtaining a blood sample from said test subject; analyzing said blood sample to obtain quantifying data on all or a subset of the metabolites listed in Table 2, or closely related entities; comparing the data obtained on said metabolites in said test subject with reference data obtained from the analysis of a plurality of clinically-diagnosed SDAT human or from a plurality of non-demented humans and using said comparison to determine the probability that the test subject is at risk of developing SDAT. Non-demented subjects with decreases levels of metabolites relative to healthy controls are at risk of developing SDAT.

In another embodiment of the present invention there is provided a method for identifying individuals who would benefit from therapy targeted towards a specific biochemical pathway aimed at restoring EtnPls to normal levels comprising: obtaining a blood samples from said test subject; analyzing said blood sample to obtain quantifying data on all or a subset of the metabolites listed in Table 2, or closely related entities; comparing the data obtained on said metabolites in said test subject with reference data obtained from the analysis of a plurality of clinically-diagnosed SDAT human or from a plurality of non-demented humans; and using said comparison to determine the probability that the test subject would benefit from such therapy.

In still another embodiment of the present invention, there is provided a method for identifying an individual who would benefit from an SDAT-specific therapy comprising: obtaining a blood samples from said test subject; analyzing said blood sample to obtain quantifying data on all or a subset of the metabolites listed in Table 2, or closely related entities; comparing the data obtained on said metabolites in said test subject with reference data obtained from the analysis of a plurality of clinically-diagnosed SDAT human or from a plurality of non-demented humans; and using said comparison to determine the probability that the test subject is benefiting from such therapy.

In a further embodiment of the present invention there is provided a method for identifying individuals who are responding to a dietary, chemical, or biological therapeutic strategy designed to prevent, treat, or stabilize SDAT and/or dementia or improve symptoms associated SDAT and/or dementia comprising: obtaining a plurality of blood samples form said test subjects separated by time; analyzing said blood samples to obtain quantifying data on all or a subset of the metabolites listed in Table 2, or closely related entities; comparing the quantifying data obtained on said metabolites in said test subject with reference data obtained from the analysis of a plurality of clinically-diagnosed SDAT human or from a plurality of non-demented humans or with reference data obtained from said test subject; and using said comparison to determine whether the metabolic state of said test subject has improved during said therapeutic strategy The present invention further provides a method for identifying dietary, chemical, or biological therapeutic strategies for the prevention, treatment, stabilization of SDAT and/or dementia or the improvement of symptoms associated SDAT and/or dementia comprising: obtaining a plurality of blood samples from a plurality of test subjects; analyzing said blood samples to obtain quantifying data on all or a subset of the metabolites listed in Table 2, or closely related entities; comparing the data obtained on said metabolites in said test subject samples with epidemiological data comprising diet history, family disease incidence, geographical location, drug use history, age, weight, gender, smoking, alcohol use, physical activity, etc.; and using said comparison to determine optimal diet, drug and behavioral conditions for the treatment or prevention of SDAT and/or dementia.

In yet another embodiment of the present invention, there is provided a method for identifying dietary, chemical, or biological therapeutic strategies for the prevention, treatment, stabilization of SDAT and/or dementia or the improvement of symptoms associated with SDAT and/or dementia comprising: incubating an in vitro cell culture model of SDAT with putative dietary, chemical, or biological agents or combinations thereof, analyzing the cells of supernatant derived from such incubations to obtain quantifying data on all or a subset of the metabolites listed in Table 2, or closely related entities; comparing the data obtained on said metabolites to reference data obtained from a plurality of cells or supernatants derived from the incubation of said model with vehicle or a reference agent; and using said comparison to determine whether said putative agent may be viable for the prevention, treatment, stabilization of SDAT and/or dementia or the improvement of symptoms associated SDAT and/or dementia.

Another embodiment of the present invention provides a method for identifying dietary, chemical, or biological therapeutic strategies for the prevention, treatment, stabilization of SDAT and/or dementia or the improvement of symptoms associated with SDAT and/or dementia comprising: administering putative dietary, chemical, or biological agent or combination thereof to an in vivo and/or ex vivo animal model of SDAT and/or dementia, analyzing all or a subset of samples derived from biofluids or tissues derived from such animal model to obtain quantifying data on all or a subset of the metabolites listed in Table 2, or closely related entities; comparing the data obtained on said metabolites to reference data obtained from the administration of vehicle or a reference agent to said model; and using said comparison to determine whether said putative agent may be viable for the prevention, treatment, stabilization of SDAT and/or dementia or the improvement of symptoms associated SDAT and/or dementia.

In a further embodiment of the present invention there is provided a method for identifying dietary, chemical, or biological strategies for the visualization of these metabolites within biofluid or tissue comprising: developing antibody or specific histochemical staining techniques in fresh, frozen, paraffin-embedded, epoxy-embedded, or other tissue preparation, using said histochemical staining technique to visualize all or a subset of the metabolites listed in Table 2, or closely related entities; and using said data to determine the involvement of said metabolites in another human health disorder.

In still another embodiment of the present invention, there is provided a method for identifying dietary, chemical, or biological therapeutic strategies for the in vivo and/or ex vivo visualization of the SDAT and/or dementia biochemical pathway comprising: administering a dietary, chemical, or biological agent or combination thereof to an in vivo and/or ex vivo animal model of SDAT and/or dementia or human with SDAT and/or dementia, analyzing the entire animal or human or specific organ systems by imaging techniques such as, but not limited to structural magnetic resonance imaging (MRI), positron emission tomography (PET), computerized tomography (CT), functional magnetic resonance imaging (fMRI), electroencephalography (EEG), single positron emission tomography (SPECT), event related potentials, magnetoencephalography, multi-modal imaging; using said non-invasive imaging to obtain quantifying data on all or a subset of the metabolites listed in Table 2, or closely related entities; comparing the data obtained on said molecules to reference data obtained from a plurality of non-demented animals/humans or with reference data obtained from said test subjects; using said comparison to determine whether the pathways involved in SDAT and/or dementia can be visualized; and if any treatment or stabilization of SDAT and/or dementia or the improvement of symptoms associated SDAT and/or dementia can be visualized.

A further embodiment of the present invention provides a method for identifying dietary, chemical, or biological therapeutic strategies for the in vivo and/or ex vivo visualization of the SDAT and/or dementia biochemical pathway comprising: administering a dietary, chemical, or biological agent or combination thereof to an in vivo and/or ex vivo animal model of SDAT and/or dementia or human with SDAT and/or dementia, analyzing all or a subset of biofluids or tissue by imaging techniques such as, but not limited to structural magnetic resonance imaging (MRI), positron emission tomography (PET), computerized tomography (CT), functional magnetic resonance imaging (fMRI), electroencephalography (EEG), single positron emission tomography (SPECT), event related potentials, magnetoencephalography, multi-modal imaging; using said non-invasive imaging to obtain quantifying data on all or a subset of the metabolites listed in Table 2, or closely related entities; comparing the data obtained on said molecules to reference data obtained from a plurality of samples obtained from non-demented animals/humans or with reference data obtained from said test subjects; using said comparison to determine whether the pathways involved in SDAT and/or dementia can be visualized; and if any treatment or stabilization of SDAT and/or dementia or the improvement of symptoms associated SDAT and/or dementia can be visualized.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows the basic structure, different R groups and naming convention used herein.

FIG. 3A shows mono and di-unsaturated EtnPls and saturated PtdEt internal control. FIG. 3B shows polyunsaturated EtnPls and free DHA (22:6). EtnPls abbreviations: (fatty acid carbons:double bonds, not including the vinyl ether double bond) and position on glycerol backbone (sn-1/sn-2). D16:0/18:0 represents diacylglycerophosphatidylethanolamine with palmitic acid (16:0) at sn-1 and stearic acid (18:0) at sn-2; 22:6 represents free DHA. Values are expressed as mean±SEM (n=19-112).

FIG. 5A is compiled from ref (5-8). FIG. 5B shows experimentally determined distributions of serum DHA-EtnPls (Log(2) EtnPls 16:0/22:6 to PhtEt 16:0/18:0 ratio). Arrow indicates positive diagnosis of SDAT.

FIG. 7A shows mean±SEM (n=68-256). The panels in FIG. 7B show Log(2) distributions.

FIGS. 24A-D show the structural determination by MS and MS/MS spectral analysis of three metabolites identified in the present invention.

FIG. 25A shows the change in EtnPls content after wild type CHO cells and Plasmalogen deficient NRel-4 cells are treated with metabolic precursor 5a (20 µM). FIG. 25B shows the change in PtdEt content of CHO and NRel-4 cells following treatment with metabolic precursor 5a. Values are normalized to untreated control CHO cells, and are an average of three independent experiments. Statistical significance was determined using a two-tailed t-test.

FIG. 26A shows the change in DHA-EtnPl content after wild type CHO cells and Plasmalogen deficient NRel-4 cells are treated with metabolic precursor 5a. FIG. 26B shows the change in DHA-PtdEt content of CHO and NRel-4 cells following treatment with metabolic precursor 5a. Values are normalized to untreated control CHO cells, and are an average of three independent experiments. Statistical significance was determined using a two-tailed t-test.

DETAILED DESCRIPTION

Figure 2:
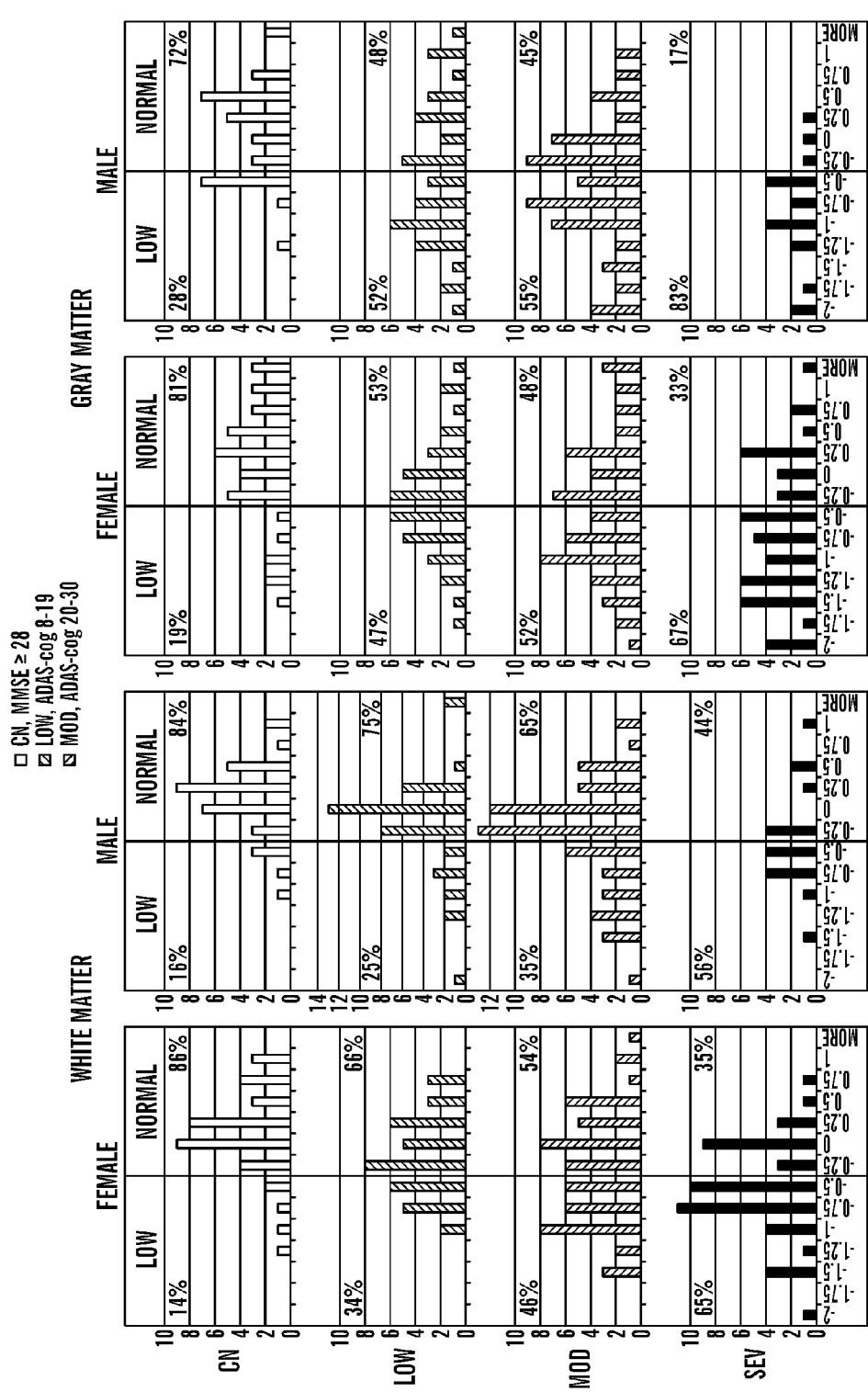
FIG. 2 is a panel of graphs showing the White Matter and Gray Matter EtnPl Score Distributions for the different dementia cohorts.

The present invention relates to small molecules or metabolites that are found to have significantly different abundances between clinically diagnosed dementia or other neurological disorders, and normal patients. The present invention also relates to methods for diagnosing dementia and other neurological disorders.

The present invention provides novel methods for diagnosing one or more diseases or particular health-states. In particular, the present invention provides methods for the diagnosis and differential diagnosis of dementia in humans by measuring the levels of specific small molecules present in a serum sample and comparing them to "normal" reference levels. The methods measure the intensities of specific small molecules, also referred to as metabolites, in the sample from patients with cognitive impairment and compare these intensities to the intensities observed in a population of non-demented healthy individuals.

The diagnosis of or the exclusion of any types of neurological disorders is contemplated by the present invention, using all or a subset of the metabolites disclosed herein. The types of dementia include, but are not limited to Senile dementia of the Alzheimer's type (SDAT), dementia with Lewy bodies (DLB), frontotemporal lobe dementia (FTD), vascular induced dementia (e.g. multi-infarct dementia), anoxic event induced dementia (e.g. cardiac arrest), trauma to the brain induced dementia (e.g. dementia pugilistica [boxer's dementia]), dementia resulting from exposure to an infectious (e.g. Creutzfeldt-Jakob Disease) or toxic agent (e.g. alcohol-induced dementia), Autism, Multiple Sclerosis, Parkinson's Disease, Bipolar Disorder, Ischemia, Huntington's Chorea, Major Depressive Disorder, Closed Head Injury, Hydrocephalus, Amnesia, Anxiety Disorder, Traumatic Brain Injury, Obsessive Compulsive Disorder, Schizophrenia, Mental Retardation, and/or Epilepsy. Of particular interest are SDAT, FTD and DLB.

The present invention provides a method of diagnosing SDAT and other types of dementia by measuring the levels of specific small molecules present in a sample obtained from a human and comparing them to "normal" reference levels. The invention further provides a method that determines whether a subject who does not show any cognitive signs of SDAT has the early neuropathological features of the disease.

In order to determine the utility of putative biochemical markers of a given health-state in a particular population, group of patients representative of the health state (i.e. a particular disease) and/or a group of "normal" counterparts are required. Biological samples taken from the patients in a particular health-state category can then be compared to the same samples taken from the normal population as well as to patients in similar health-state category in the hopes of identifying biochemical differences between the two groups. The biological samples could originate from anywhere within the body, for example but not limited to, blood (serum/plasma), CSF, urine, stool, breath, saliva, or biopsy of any solid tissue including tumor, adjacent normal, smooth and skeletal muscle, adipose tissue, liver, skin, hair, brain, kidney, pancreas, lung, colon, stomach, or other. Of particular interest are samples that are serum or CSF. While the term "serum" is used herein, those skilled in the art will recognize that plasma or whole blood or a sub-fraction of whole blood may be used.

The method of the present invention is minimally invasive and is indicative of cognitive impairment and of SDAT pathology. Translation of the method into a clinical assay compatible with current clinical chemistry laboratory hardware is commercially acceptable and effective. Furthermore, the method of the present invention does not require highly trained personnel to perform and interpret the test.

The present invention detects and measures metabolites that have statistically significant differential abundances between clinically diagnosed SDAT dementia and non-demented normal serum. Furthermore, the present invention detects and measures metabolites that have statistically significant differential abundances between post-mortem collected serum samples from pathologically confirmed SDAT subjects versus post mortem serum samples collected from subjects with minimal SDAT pathology.

Cognitive Impairment.

Cognitive impairment can be assessed by any method known in the art. For example, and without wishing to be limiting, the Alzheimer's Disease Assessment Scale (ADAS)-cognitive subset may be used. This neuropsychological test is used to test the language ability (speech and comprehension), memory, ability to copy geometric figures and orientation to current time and place. Errors on the test are recorded resulting in a reverse score impairment. (i.e. The higher the score on ADAS, the greater the cognitive impairment). A score of 0-15 is considered normal, 16-47 is considered mild-moderate impairment and a score of 48-70 is considered moderate-severe impairment [2].

Sample Processing.

When a blood sample is drawn from a patient there are several ways in which the sample can be processed. The range of processing can be as little as none (i.e. frozen whole blood) or as complex as the isolation of a particular cell type. The most common and routine procedures involve the preparation of either serum or plasma from whole blood. All blood sample processing methods, including spotting of blood samples onto solid-phase supports, such as filter paper or other immobile materials, are also contemplated by the invention.

Sample Extraction.

The processed blood sample described above is then further processed to make it compatible with the methodical analysis technique to be employed in the detection and measurement of the biochemicals contained within the processed serum sample. The types of processing can range from as little as no further processing to as complex as differential extraction and chemical derivatization. Extraction methods could include sonication, soxhlet extraction, microwave assisted extraction (MAE), supercritical fluid extraction (SFE), accelerated solvent extraction (ASE), pressurized liquid extraction (PLE), pressurized hot water extraction (PHWE) and/or surfactant assisted extraction (PHWE) in common solvents such as methanol, ethanol, mixtures of alcohols and water, or organic solvents such as ethyl acetate or hexane. The preferred method of extracting metabolites for HTS analysis is to perform a liquid/liquid extraction whereby non-polar metabolites dissolve in an organic solvent and polar metabolites dissolve in an aqueous solvent.

Selection of Metabolites

The metabolites described in the invention are listed in Table 2, where the second column names the metabolite as described in FIG. 1 and the last column describes the Parent-Fragment MS/MS transition used for quantifying the molecule as described below. In a previous application (U.S. provisional 60/804,779 filed Jun. 14, 2006), the applicant discovered specific ethanolamine plasmalogens to be decreased in the serum of SDAT subjects. Based upon these discoveries, a panel of diacyl, plasmanyl and EtnPls metabolites was developed using common fatty acid side chain constituents (16:0, 18:0, 18:1, 18:2, 20:4, 22:4, 22:6). This list is not meant to be exhaustive but to be sufficiently broad enough to determine if the entire pathway is changing or if only certain classes of ethanolamine phospholipids are changing. However, a person of skill in the art would recognize that other ethanolamine phospholipids with different fatty acid side chains or other metabolites of similar structure, which are involved in similar biochemical pathways could be used for similar purposes as described below. All such modifications of the invention are contemplated herein.

Mass Spectrometry Analysis of Extracts.

Extracts of biological samples are amenable to analysis on essentially any mass spectrometry platform, either by direct injection or following chromatographic separation. Typical mass spectrometers are comprised of a source which ionizes molecules within the sample, and a detector for detecting the ionized molecules or fragments of molecules. Examples of common sources include electron impact, electrospray ionization (ESI), atmospheric pressure chemical ionization, atmospheric pressure photo ionization (APPI), matrix assisted laser desorption ionization (MALDI), surface enhanced laser desorption ionization (SELDI), and derivations thereof. Common mass separation and detection systems can include quadrupole, quadrupole ion trap, linear ion trap, time-of-flight (TOF), magnetic sector, ion cyclotron (FTMS), Orbitrap, and derivations and combinations thereof.

LC-MS Analysis of Human Serum Samples (Chromatography).

The present invention provides a chromatographic method combined with a mass spectrometric detector for the quantitative and qualitative characterization of ethanolamine phospholipids in serum. Embodiment of the method are described in Examples 3 to 8.

LC-MS Analysis of Human Serum Samples (Flow Injection).

The present invention also provides high throughput methods for differential diagnosis of SDAT dementia and non-SDAT dementia states. The method involves fragmentation of the parent molecule; in a non-limiting example, this may be accomplished by a Q-Trap™ system. Detection of the metabolites may be performed using one of various assay platforms, including colorimetric chemical assays (UV, or other wavelength), antibody-based enzyme-linked immunosorbant assays (ELISAs), chip-based and polymerase-chain reaction for nucleic acid detection assays, bead-based nucleic-acid detection methods, dipstick chemical assays or other chemical reaction, image analysis such as magnetic resonance imaging (MRI), positron emission tomography (PET) scan, computerized tomography (CT) scan, nuclear magnetic resonance (NMR), and various mass spectrometry-based systems. One embodiment of the method is described in Example 9.

Structural Confirmation of Metabolites.

The present invention also provides the structural characteristics of the metabolites used for the differential diagnosis of SDAT dementia and non-SDAT dementia, which may include accurate mass and molecular formula determination, polarity, acid/base properties, NMR spectra, and MS/MS or MSn spectra. Techniques used to determine these characteristics include, but are not limited to reverse or normal phase LC-MS followed by analysis by MS, MS/MS fragmentation using collision induced dissociation (CID), nuclear magnetic resonance (NMR), and extraction. The characteristics of the metabolites obtained by various methods can then be used to determine the structure of the metabolites. One embodiment of the method is described in Example 10.

In humans, the oxidative by-products, and thus turn-over, of plasmalogens are dramatically increased with age in both the brain (86) and in peripheral red blood cell membranes (87). Increased oxidative stress and decreased synthesis of EtnPl s and DHA both point toward decreased peroxisomal function (39, 62, 80, 81). Catalase, the principal peroxisomal enzyme responsible for detoxifying the $H_2O_2$ created by peroxisomes, decreases in activity with age (73-75), most likely due to compromised catalase import (79). The combination of the EtnPl vinyl ether bond, which is preferentially oxidized during oxidative stress (42), the critical requirement of EtnPl for membrane fusion events (52) and the fact that over half of the neuronal membrane ethanolamine phospholipid composition is EtnPl (34), points toward decreased EtnPls as the means by which oxidative stress creates membrane dysfunction (50). Furthermore, the timing of Aβ accumulation and increased lipid peroxidation (55) closely matches the timing of decreased peroxisomal activity (70) and decreased EtnPls levels (34) in mice. Peroxisomal proliferation inhibits Aβ induced neurodegeneration (71), preserves cognition in early SDAT (72), and peroxisomal function appears to be critical for neuronal migration (69). The applicant, through the combination of these findings and the novel findings presented herein introduces the novel hypothesis that the mechanism by which PPARs exert their activity in SDAT is through the enhancement of EtnPls levels. This has significant implications in the treatment of SDAT by such molecules in that, individuals detected by the methods described in this application as deficient in EtnPls may preferentially benefit from PPAR therapy.

The fact that peripheral changes in these metabolites correlate with CNS changes of these metabolites (34) and with CNS amyloid pathology, suggests that an equilibrium between these compartments exists. Animal studies on the synthesis and transport of DHA containing phospholipids have shown that the primary site of synthesis of DHA is the liver, where this newly synthesized DHA is first incorporated into phospholipids prior to being transported to the brain via the serum (82).

However, the present inventors are the first to show that EtnPls are decreased in the periphery (i.e. serum) in subjects suffering from dementia and in subjects with CNS amyloid pathology, and to establish the utility of using serum EtnPls levels as a diagnostic method for dementia or SDAT.

Figure 23:
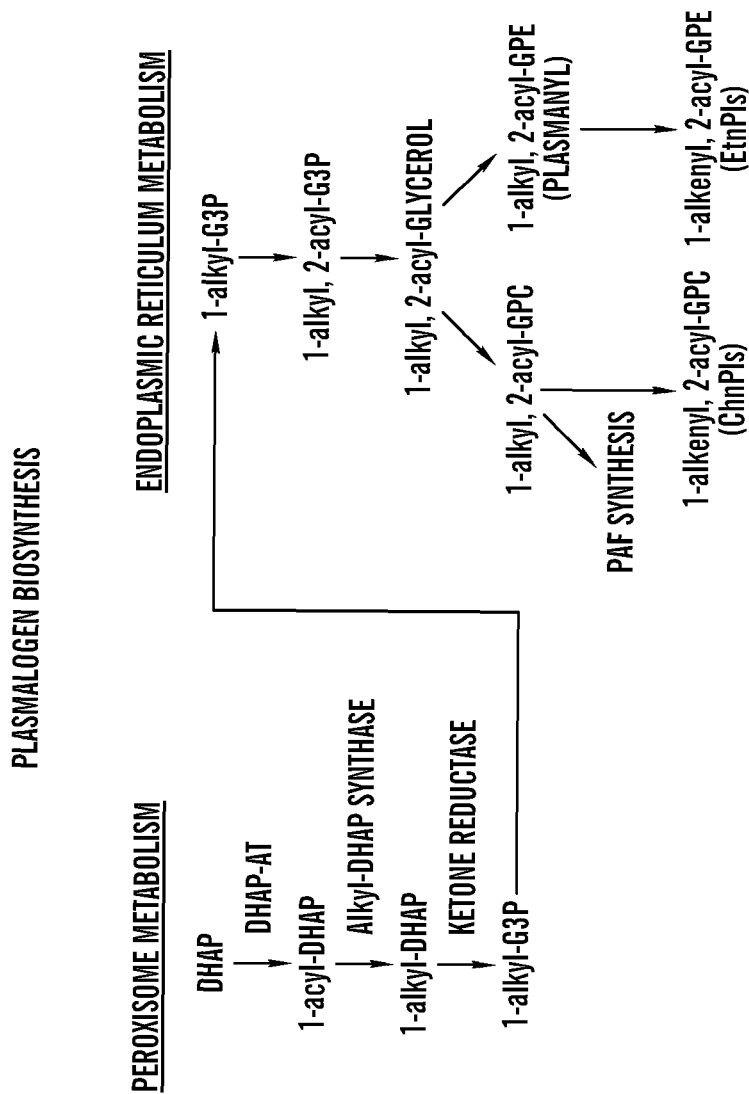
FIG. 23 shows an extracted biosynthesis pathway. DHAP—Dihydroxyacetone phosphate; DHAP-AT—Dihydroxyacetone phosphate acyltransferase; G3P—glyceraldehyde-3-phosphate; GPE—glycerylphosphatidylethanolamine; GPC—glycerylphosphatidylcholine; PAF—platelet activating factor.
Figure 24B:
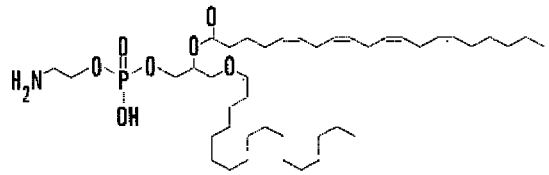

The present inventors have also shown that plasmanyl ethanolamine phospholipids are also decreased in subjects suffering from dementia and in subjects with CNS amyloid pathology. This is a critical finding in that it indicates that the decrease EtnPls is due to a decrease in ether lipid synthesis in SDAT and not due to oxidative breakdown of EtnPls (plasmanyl molecules do not contain the vinyl ether linkage and therefore are not susceptible to oxidative breakdown). Since the formation of this ether bond occurs exclusively in peroxisomes, this provides the first direct evidence of a peroxisomal impairment in SDAT. As peroxisomal function appears to be impaired, any strategy that enhances the biochemical steps in the biosynthetic pathway that culminates in EtnPls, has potential utility in treating SDAT. This biochemical pathway is illustrated in FIG. 23. Allosteric modulators (agonists) that enhance the activity of any of the enzymes described could potentially be useful therapeutics in the treatment or prevention of SDAT. In addition the administration of substrates or pro-substrates molecules that get metabolized to substrates) of any of the molecules described in this pathway are also potentially useful therapeutics in the treatment of SDAT. Finally molecules that create a general increase in peroxisomal activity (such as PPAR agonists, for example Avandia (rosiglitazone)) could also be potentially useful therapeutics in the treatment of SDAT, especially in subjects determined to be deficient in EtnPls.

In addition to the metabolic precursors listed in FIG. 23: DHAP; 1-acyl-DHAP; 1-alkyl-DHAP; 1-alkyl-G3P; 1-alkyl, 2-acyl-G3P; 1-alkyl, 2-acyl-glycerol; 1-alkyl, 2-acyl-GPE the following molecules can also be used as a therapeutic for the treatment of SDAT: 1-alkyl, diacyl glycerol (sn-1=16:0, sn-2=DHA, sn-3=DHA) (sn-1 position has an alkyl ether bond, sn-2 and sn-3 positions have acyl bonds); 1-alkyl diacyl glycerol (sn-1=16:0, sn-2=18:1, sn-3=18:1) (sn-1 position has an alkyl ether bond, sn-2 and sn-3 positions have acyl bonds); triacyl glycerol (sn-1=16:0, sn-2=DHA, sn-3=DHA) (all three positions have acyl bonds); and triacyl glycerol (sn-1=16:0, sn-2=18:1, sn-3=18:1) (all three positions have acyl bonds).

In one aspect of this embodiment of the invention, the method for the treatment of SDAT comprises the administration of a 1-alkyl, 2-acyl-glycerol.

The sidechains should include any common fatty acid and long-chain fatty acids, including those of both the saturated and unsaturated (PUFA) type. Specific examples include: 16:0, 18:0, 18:1, 18:2, 18:3 as alkyls at SN1, and 16:0, 18:0, 18:1, 18:2, 18:3, 20:4, 20:5, 20:6, 22:4, 22:5, 22:6, 24:4, 24:5, 24:6 as acyls at SN2.

In a further aspect of this embodiment the 1-alkyl, 2-acyl-glycerol is as shown below:

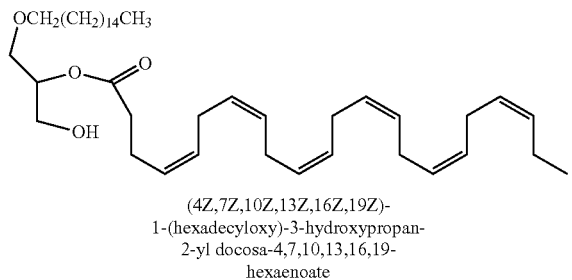

(4Z,7Z,10Z,13Z,16Z,19Z)-
1-(hexadecyloxy)-3-hydroxypropan-
2-yl docosa-4,7,10,13,16,19-
hexaenoate The present inventors have also shown that depleted serum EtnPls are a causative factor in SDAT. Aβ accumulation, the primary pathological hallmark of SDAT, results from the dysfunctional membrane processing of amyloid precursor protein (APP). The non-pathological process (>95% of total APP processing) occurs via the α-secretase pathway and the pathological process occurs via the β-secretase pathway. α-secretase is located in a phospholipid-rich membrane domain whereas β-secretase is located in cholesterol-rich lipid rafts. Both of these enzymes are sensitive to changes in membrane cholesterol in that increasing membrane cholesterol simultaneously inhibits α-secretase activity (18) and activates β-secretase (19, 20), (see (21), for review). Thus disturbances in neuronal cholesterol processing, such that there is an increase in cellular cholesterol, shifts the normal APP processing cascade from the non-pathological process to the pathological process. The relationship between membrane cholesterol and SDAT severity is compelling (22). EtnPls deficiency decreases cholesterol efflux (23) and conditions that decrease membrane plasmalogens simultaneously increase membrane cholesterol (24). Furthermore, the decrease in serum EtnPls in SDAT described herein occurs at an earlier stage of SDAT than the increase in membrane cholesterol reported above (22). In addition to the cholesterol connection, the timing of depleted EtnPls implicates decreased peroxisomal function (the exclusive site of EtnPls synthesis) as a causal factor in SDAT. In mice, genetic conditions that produce 30 times the normal amount Aβ fail to result in accumulation until after 8 months of age (25, 26). Aβ accumulation in humans also requires an age-related trigger (27, 28). A well documented age-related phenomenon is decreased peroxisomal function (29). Decreased peroxisomal function leads to decreased synthesis of EtnPls and DHA (30-32). The timing of Aβ accumulation closely matches the timing of decreased peroxisomal activity in mice (33) and the decreased levels of EtnPls reported herein closely match the timing of Aβ accumulation in humans. Finally, peroxisome proliferation inhibits Aβ induced neurodegeneration (34) and preserves cognition in early SDAT (35). However in these papers, the authors discuss attribute their results to decreased oxidative stress (34) or decreased insulin sensitivity (35) and not to restoration of EtnPls levels.

Thus, according to the present invention there is also provides a method for lowering cholesterol in a patient in need thereof, by administering to said patient a therapeutically effective amount of one or more of the molecules described above.

The present inventors also show that the depleted serum EtnPls described herein is unlikely due solely to Aβ accumulation. A possible explanation for the decreased serum EtnPls observed in this study is the oxidative breakdown of these metabolites resulting from Aβ accumulation. This may be the case in the CNS since decreased EtnPls in the CNS are co-localized with Aβ (10, 12-14) and Aβ can directly deplete neuronal EtnPls content (11). However, serum Aβ levels do not correlate with SDAT diagnosis or severity (36) and in aged humans white matter EtnPls content is equally decreased in all brain regions at all levels of dementia (10). These findings argue against Aβ accumulation as the sole cause of the systemic depletion of EtnPls described herein. These two mechanisms of EtnPls depletion are not mutually exclusive. It is entirely plausible that a systemic depletion in EtnPls, as described herein could initiate the accumulation Aβ by disrupting neuronal and glial membranes, and that once Aβ accumulates to some threshold in the CNS, it creates an oxidative environment that further contributes to the depletion of membrane EtnPls.

The present invention also addresses several key points:

1) The chemical nature of these biomarkers is such that they can be readily measured systemically. This point is of fundamental importance since the majority of research pertaining to SDAT and other neurological disorders has ignored the peripheral systems. The ability to measure neurodegenerative processes within a blood sample would make this invention unique and of substantial value.

2) The depletion of ethanolamine plasmalogen within the cell membrane of the cholinergic neurons is a viable hypothesis for the development of SDAT.

3) The EtnPls could be used as a valid biochemical marker of SDAT pathology since this molecular species' content does not change in Parkinson's disease, a disease which is often accompanied by dementia [120].

Figure 6:
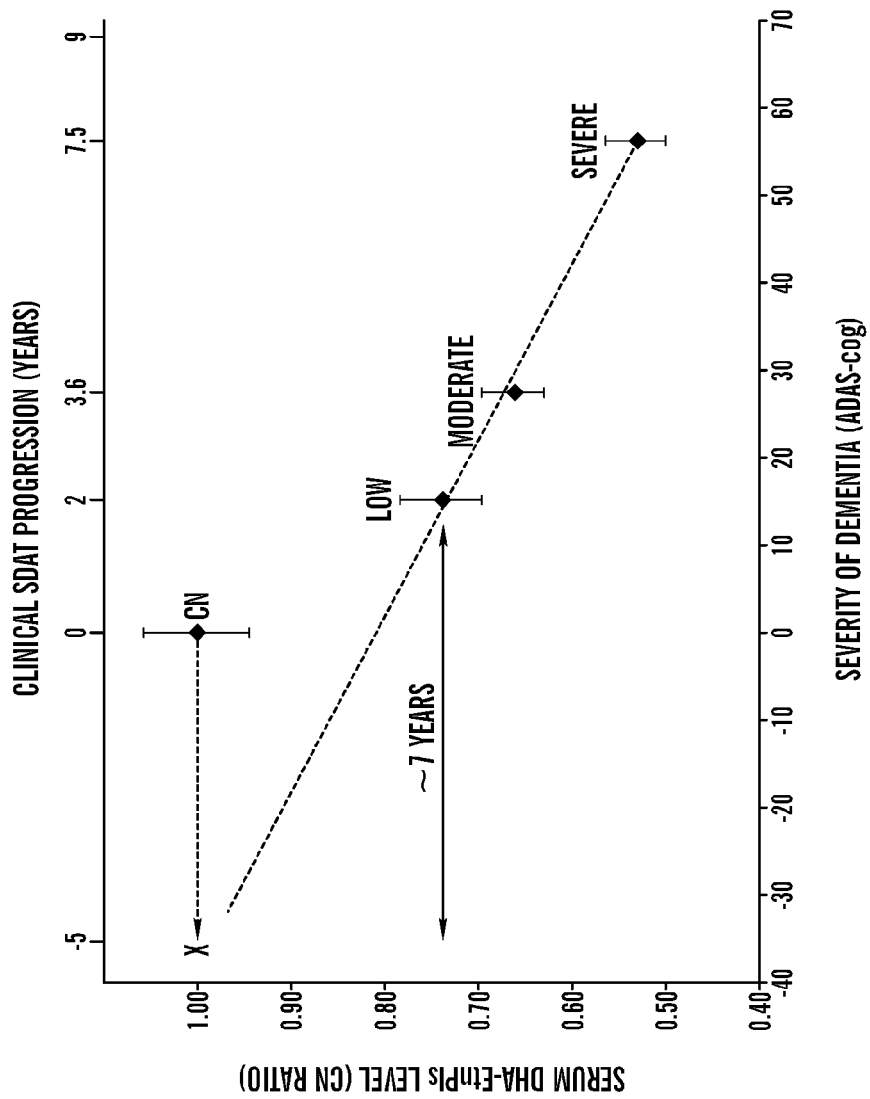
FIG. 6 is a linear regression analysis of disease severity (ADAS-cog) and serum DHA-PlsEtn (EtnPls 16:0/22:6 to PtdEt 16:0/18:0 ratio) levels in 256 SDAT subjects. X=predicted initiation of PlsEtn depletion. Values are expressed as mean±SEM (n=66-112). Clinical progression assumes 7.5 ADAS-cog points/year.

4) The specificity of plasmalogen to SDAT indicates that its content within serum could be readily measured longitudinally throughout the lifetime of an individual to assess the risk or for the early detection of SDAT prior to the emergence of clinical symptoms, as the ethanolamine plasmalogen content has been shown to be decreased in postmortem tissue of very mildly impaired SDAT patients (26) and is predicted by our analyses to occur up to seven years prior to clinical symptoms of dementia (FIG. 6)

5) Since the metabolites are decreased in SDAT and dementia, a pharmaceutical, biological or nutritional supplementation strategy that specifically targets metabolic systems that either lead into or from these metabolites with the intent of increasing these biomarkers is viable. Furthermore, the direct supplementation of these metabolites or related metabolites or derivatives of such could be used in the treatment or prevention of SDAT or dementia.

Specifically in regards to the therapeutic strategy for the restoration of EtnPls to normal levels in subjects found to be deficient, supplementing such individuals with various ether lipid molecules that can either be further modified or used "as-is" by such individual's metabolic apparatus body strategies are contemplated. Such molecules, for example, but not meant to be limiting, could include the following:

1) The predominant sn-1 moieties (R1, FIG. 1) for ether lipids in humans are derived from cetyl alcohol (1-hexadecanol, 16:0), stearyl alcohol (1-octadecanol, 18:0), and oleyl alcohol (cis-9-octadecen-1-ol, 18:1). These would be the preferred R1 substitutions of the glyceryl backbone. Since the incorporation of the vinyl ether occurs outside of the peroxisome, the formation of this vinyl bond, is not considered to be rate-limiting in the formation of EtnPls in humans. This is supported by the applicant's observation that both plasmanyl and EtnPls metabolites disclosed herein decrease in parallel in SDAT. Therefore, supplementation with the plasmanyl form should result in increased levels of EtnPls.

However, both the O-ether (plasmanyl) and the O-vinyl ether (Plasmenyl) are contemplated as viable sn1 moieties for therapeutic supplementation. It is further contemplated that a mixture of supplements containing an optimal ratio of sn-1 constituents may be necessary to fully restore the body's natural ratio of these molecules;

2) The preferred constituent at the sn-2 position is DHA. Subjects with an impaired peroxisomal system could also have impaired synthesis of DHA and the DHA containing EtnPls show the most robust and earliest decrease in SDAT. However, sn-2 moieties ranging from the simple free alcohol (R2=OH) or acetyl (R2=O—C(O)—CH3) to any common (i.e. 16:0. 16:1, 18:0, 18:1, 18:2, 18:3, 20:4, 22:4, 24:6) or modified fatty acid is a viable sn-2 constituent from a therapeutic supplementation strategy;

3) The preferred constituent at the sn-3 position is the free alcohol (R3=OH). However, sn-3 moieties ranging from the simple phosphate (R3=PO4) to fully intact phosphoethanolamine (R3=O—P(O)(OH)—O—C2H4NH2) or derivatives or other moieties that can be converted back to the free alcohol or phosphate are viable sn-3 moieties from a therapeutic supplementation strategy.

4) The administration of one or a combination of one or more molecules resulting from the combination of the sn-1, sn-2 and sn-3 positions disclosed above is contemplated as a potential therapeutic intervention aimed at increasing levels of EtnPls. The preferred route of administration of such molecule(s) would be oral. However other possible routes such as intraperitoneal or intramuscular injection, intravenous, transdermal patch, or other is contemplated. Oral administration could be in the form of a gel capsule or as a soluble or emulsified liquid or mixed with an appropriate food product.

The formulations comprising the compounds of the present invention may be manufactured in unit dosage forms and may be prepared by any of the methods well known in the art. In general the formulations can be prepared by bringing the compounds together with a pharmaceutically acceptable carrier and formulating the product into acceptable forms, as noted above.

The compounds can be used directly or as a pharmaceutically acceptable salt form. Any salt conventionally used in the formulation and administration of pharmaceutical preparations can be used according to the present invention. Suitable salts include both organic salts such as succinates, fumarates, malonates, crotonates and the like, as well as inorganic salts such as chlorides, sodium, potassium, calcium, nitrates, phosphates, sulfates and the like.

A therapeutically effective dose of the compounds of the present invention will determined empirically, depending on a number of factors including the time since onset of the condition, the progression of the condition, as well as the general health of the individual and their age. As a general guide the compounds of the present invention can be administered from about 1 mg/kg body weight to about 10 g/kg of body weight. A more suitable dose may be from about 100 mg/kg body weight to about 500 mg/kg body weight. The compounds can be administered as a single dose or in multiple daily doses, as appropriate.

Likewise, a pharmaceutical, biological or nutritional supplementation program that blocks or inhibits a part of the biochemical pathway may reduce the production of these biomarkers and induce SDAT pathology and/or demential symptoms. Therefore, these biomarkers can be used to monitor for potential dementia-related adverse reactions to a pharmaceutical, biological or nutritional therapy, regardless of the intended disease target of these therapies.

For routine analysis, a novel method that quantitates a subset of the metabolites is described. There are multiple types of cost-effective assay platform options currently available depending on the molecules being detected. These include colorimetric chemical assays (UV, or other wavelength), antibody-based enzyme-linked immunosorbant assays (ELISAs), chip-based and polymerase-chain reaction for nucleic acid detection assays, bead-based nucleic-acid detection methods, dipstick chemical assays, image analysis such as magnetic resonance imaging (MRI), positron emission tomography (PET) scan, computerized tomography (CT) scan, and various mass spectrometry-based systems.

The preferred method involves the development of a high-throughput MS/MS method that is compatible with current laboratory instrumentation and triple-quadrupole mass spectrometers which are readily in place in many labs around the world. A Q-Trap™ system is used to isolate the parent molecule, fragment it; and then the fragments are measured. Internal standards are used to correct for sample to sample variance.

The present invention will be further illustrated in the following examples.

Example 1: Effect of Aging and Severity of Dementia on Serum Levels of Ethanolamine Phospholipids The effect of aging and severity of dementia on serum levels of ethanolamine phospholipids in 752 subjects aged 40-95 with various levels of dementia was investigated. The clinical data on the subject cohorts is shown in Table 1.

The effect of age was evaluated using a set of aged 30 to 95 of untested cognitive status but who were currently not suffering from dementia. Subjects were grouped into one of five subgroups based upon their decade of life (30's, 40's, 50's, 60's, and ≥70). The 40-49 cohort was used as the pre-dementia reference group due to the low incidence of dementia at this age. A significant gender bias was observed in that only females exhibited an age-related decrease in EtnPls. Free DHA in both males and females was significantly increased in the 50-59, 60-69, and 70+ cohorts relative to the 40-49 cohorts. However, only males exhibited a concomitant increase in both 16:0/and 18:0/DHA-EtnPl. These data suggest that, in females, there may be an age-related dysfunction in the packaging of DHA into EtnPls. This gender difference may explain the increased incidence of dementia in very old females (84).

The effect of dementia severity was determined in subjects aged 56 to 95, comprised of 68 cognitively confirmed non-demented subjects (MMSE≥28); 256 subjects currently diagnosed with SDAT (ADAS-cog 6-70, MMSE 0-26); 20 post-mortem confirmed SDAT and 20 post-mortem confirmed controls. Subjects were grouped into one of four dementia subgroups based upon either their MMSE score [≥28=Cognitively Normal] or their ADAS-cog score [5-19=low cognitive impairment); 20-39=moderate; 40-70=severe]. In both males and females, the majority of EtnPls in all dementia subgroups were significantly reduced relative to cognitive controls. In both males and females, free DHA was significantly decreased only in severely demented subjects. In females, a dementia effect was observed for three EtnPls (16:0/18:2, 18:0/18:2, and 16:0/20:4) in that both 18:2/EtnPls were significantly lower in severely demented subjects versus either low or moderately demented females and 16:0/20:4 was lower in the severe group versus the low group. In males, a dementia effect was observed for DHA and 16:0/DHA in that free DHA was reduced in the moderate group versus the low group and in the severe group versus the moderate group and 16:0/DHA was reduced in the severe group versus the low group. These results suggest that there is a general underlying dysfunction in plasmalogen synthesis in SDAT, regardless of gender but that the progressive cognitive deterioration in SDAT manifests slightly differently in the two sexes. Brain white matter contains primarily 18:1 and 18:2 EtnPls with low levels of 20:4 and DHA EtnPls whereas gray matter contains significantly higher levels of 20:4 and DHA EtnPls. In females, increasing dementia appears to affect both white (18:2) and gray (20:4) matter EtnPls equally, whereas in males predominantly gray (DHA) matter EtnPls appear to be affected to a greater extent. These findings indicate that therapeutic strategies could be optimized for either males or females or individually depending upon the specific EtnPls deficiency observed.

The effect of CNS amyloid pathology was assessed in post-mortem collected serum samples from 20 pathologically confirmed SDAT subjects and 20 subjects containing minimal amyloid deposition. Both gray and white matter EtnPls were significantly decreased in post-mortem confirmed SDAT relative to age matched controls.

Example 2: The Grey and White Matter Score Distribution

Considering the differential regional (34) and gender differences in white vs. gray matter EtnPls, a white and gray matter specific EtnPl scoring system was developed whereby each EtnPl in each subject was normalized to their respective gender-specific cognitively normal mean, log 2 transformed and mean centered. Each subject's white matter score was taken as the lowest such value of plasmenyl 16:0/18:1, 16:0/18:2, 18:0/18:1, 18:0/18:2 EtnPls (M15, M16, M20 and M21) and their gray matter score as the lowest of plasmenyl 16:0/20:4, 16:0/DHA, 18:0/20:4, 18:0/DHA (M17, M19, M22 and M24) EtnPls. These simplified scores revealed that both gray and white matter EtnPls were decreased at all stages of SDAT and that the levels in post-mortem confirmed SDAT closely matched levels in severely demented subjects of both sexes. The cross-sectional white and gray matter score distributions in subjects of various levels of dementia clearly showed a dementia dependent shift in the population means. This also indicated that changes in serum levels of gray matter EtnPls may precede white matter changes and potentially be an early risk factor for SDAT. Such cross-sectional data does not account for baseline variability among subjects. Individual longitudinal trajectories of these scores may be more accurate at detecting early risk of SDAT in otherwise healthy, non-demented subjects. Based upon these scores, risk prediction can be performed on both male and female subjects (Tables 15 and 17) where a cut-off value that results in approximately 20-30% of cognitively normal subjects being classified as either intermediate or high risk is used. Using this cut-off value a subjects white and gray matter score is evaluated. If the subject tests normal on both scores, the subjects is deemed to be at low risk. If the subject tests positive on one of the scores, the subjects is deemed to be at intermediate risk and if the subject tests positive on both scores, the subject is deemed to be at high risk.

Example 3: Quantitative and Qualitative Characterization of Ethanolamine Phospholipids in Serum The present invention provides a chromatographic method combined with a mass spectrometric detector for the quantitative and qualitative characterization of ethanolamine phospholipids in serum.

For MS/MS applications and experiments involving chromatography, an Agilent 1100 HPLC system was used in combination with an Applied Biosystems QSTAR XL mass spectrometer. An Agilent Zorbax RX-SIL (4.6×150 mm, 5 µm) column was used for normal phase chromatography. Conditions included an isocratic mobile phase (55:40:5 isopropanol:hexane:H2O) at a flow rate of 1.0 mL/min for a total run time of 15 min. The column was heated to 35° C. The sample injection volume was 10 µL. Organic solvent extracts (ethyl acetate) of samples were evaporated to dryness under nitrogen gas and the residue was reconstituted in 100 µL of 55:40:5 isopropanol:hexane:H2O solution prior to injection. FIGS. 10-22 show examples of representative metabolites detected in serum.

The QSTAR XL instrument was equipped with an APCI (Heated Nebulizer) source operating in negative mode. Values of major instrument parameters were DP, −60; FP, −265; DP2, −15; GS1, 75; GS2, 15; CUR, 30; NC, −3; TEM, 400° C.; Scan range, 50-1500 amu; Accumulation time, 1 sec.

Figure 3B:
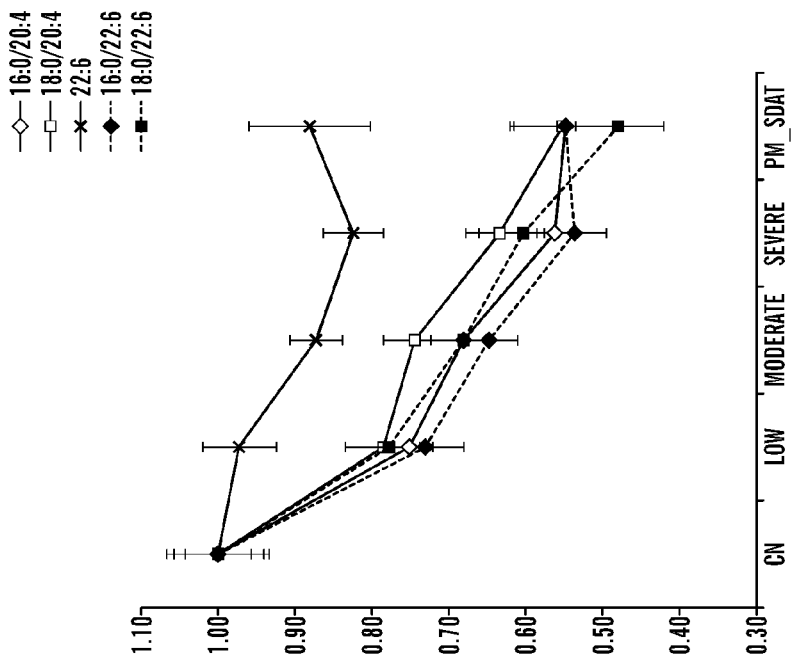
FIGS. 3A-3B show the effect of dementia severity and SDAT pathology on serum EtnPl levels (male and female subjects combined).
Figure 3A:
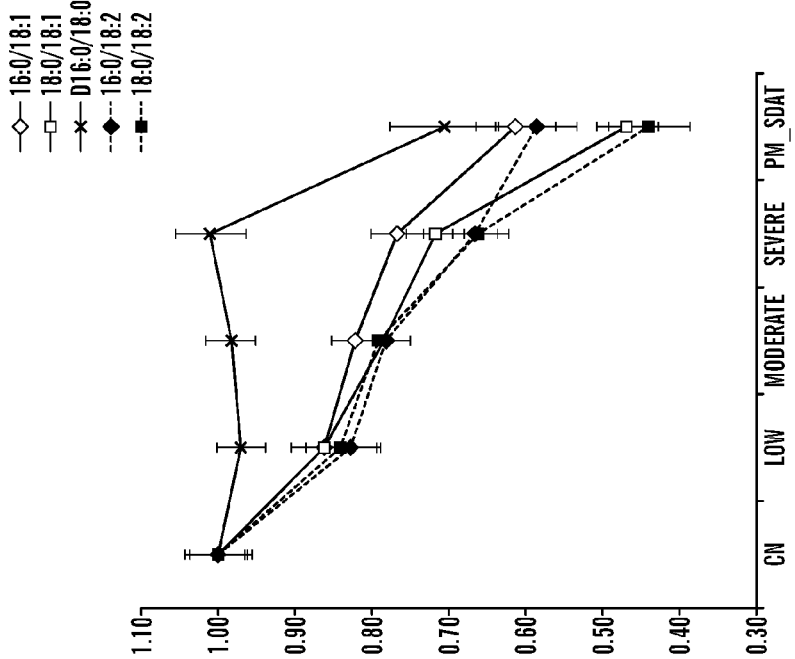
Figure 4:
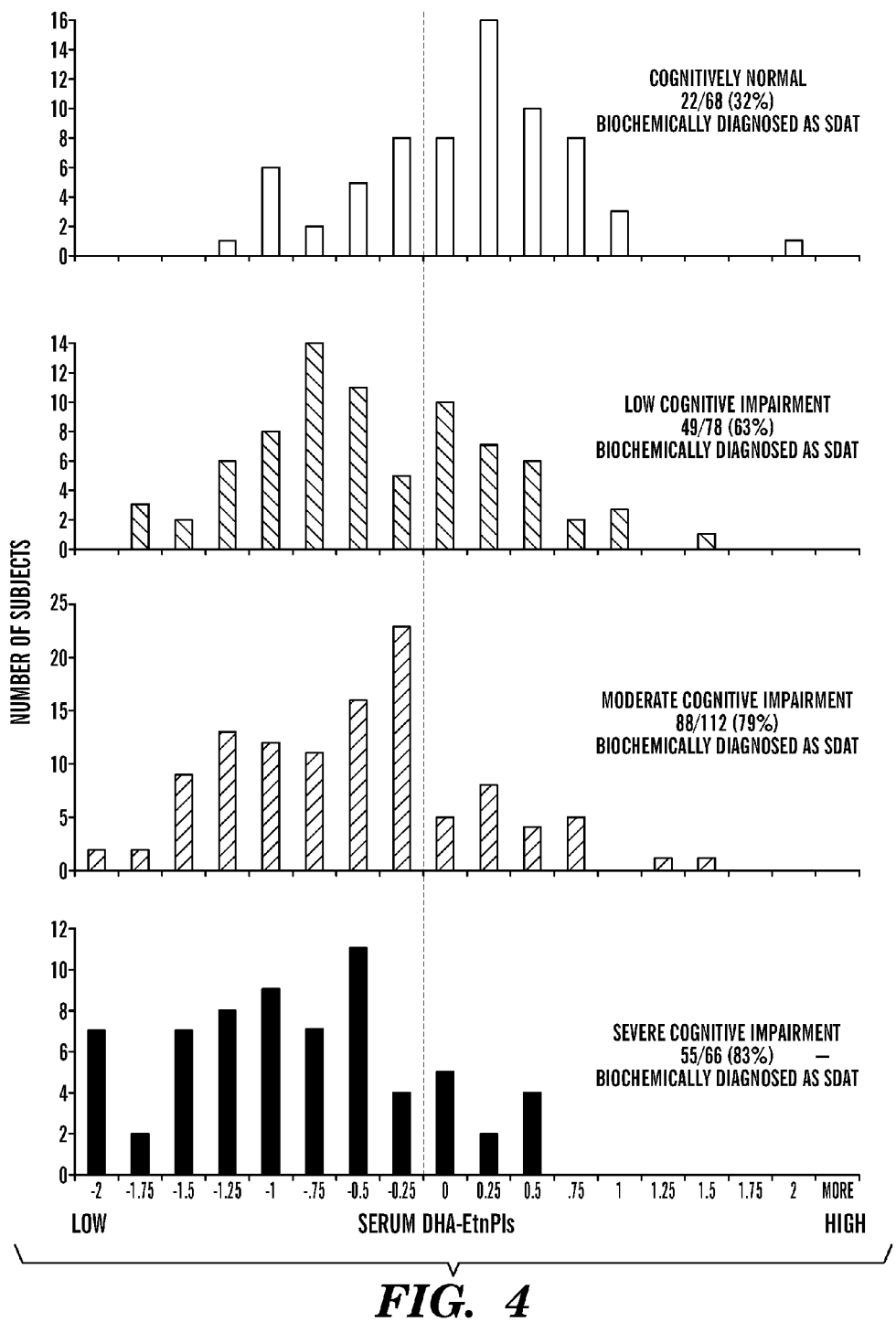
FIG. 4 is a panel of graphs showing serum DHA-EtnPls (Log(2) EtnPls 16:0/22:6 to PhtEt 16:0/18:0 ratio) distributions in subjects with different levels of dementia severity: top panel—cognitive normal; second panel—low-cognitive impairment; third panel—moderate-cognitive impairment; fourth panel—severe-cognitive impairment (male and female subjects combined).
Figure 5A:
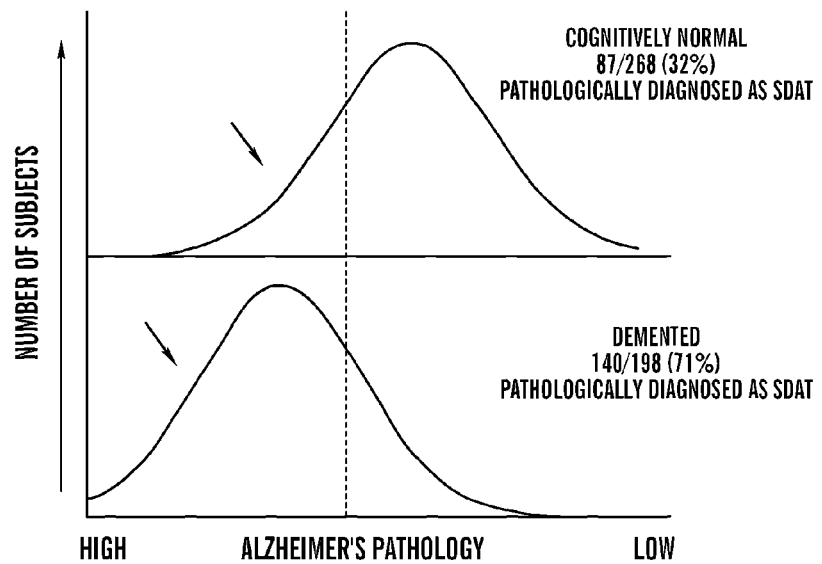
FIGS. 5A-5B give a comparison of theoretical distributions of SDAT pathology in cognitively normal and demented subjects.
Figure 5B:
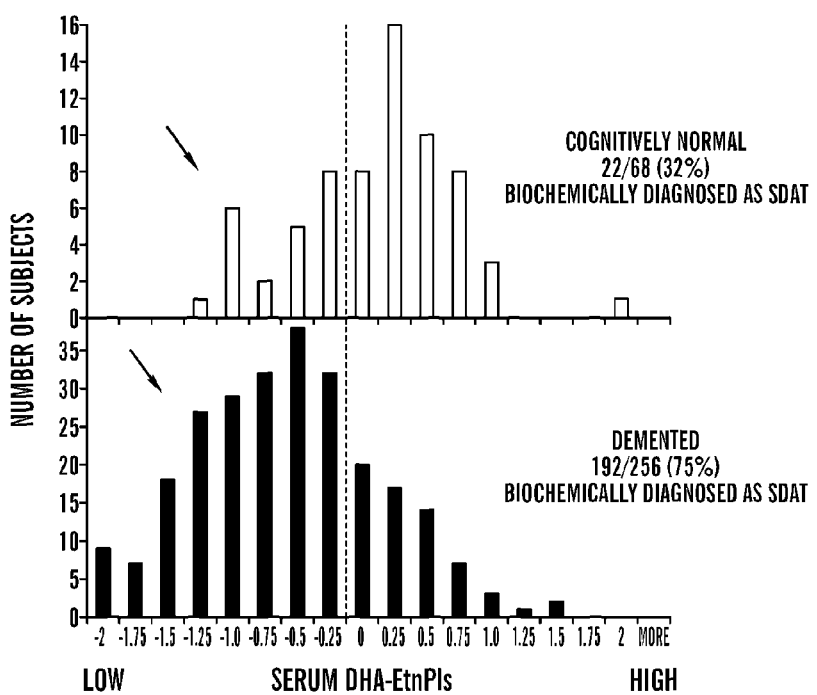

Example 4: Effect of Dementia Severity and SDAT Pathology on Serum EtnPls Levels in Combined Male and Female Subjects The effect of dementia severity was determined using 324 subjects (176 female, 148 male) aged 56 to 95, comprised of 68 cognitively confirmed non-demented subjects (MMSE≥28) and 256 subjects currently diagnosed with SDAT (ADAS-cog 6-70, MMSE 0-26). The effect of SDAT pathology was determined using serum samples collected from 20 post-mortem confirmed SDAT and 19 control subjects (Table 1). Subjects were grouped into one of four dementia severity cohorts based upon either their MMSE score [≥28=Cognitively Normal] or their ADAS-cog score [5-19=low cognitive impairment; 20-39=moderate; 40-70=severe]. Mean serum levels of eight EtnPls, free docosahexaenoic acid (DHA, 22:6), and phosphatidylethanolamine (PtdEt) 16:0/18:0 (D16:0/18:0) were determined for each group (FIGS. 3A-B). All eight EtnPls in all dementia subgroups were observed to be significantly reduced relative to cognitive controls (24 pair-wise comparisons, t-test p-values 2.6e-2 to 2.0e-10, median=3.9e-5). Free DHA was significantly decreased in both moderately and severely demented subjects (p<0.05). All eight EtnPls were also significantly decreased in post-mortem confirmed SDAT relative to age matched controls. D16:0/18:0 levels, a non-plasmalogen phosopholipid remained unchanged across the different dementia cohorts. In all further analyses, the EtnPls to D16:0/18:0 (M01) ratio was used to minimize sample to sample variability. Both the absolute EtnPls levels and the EtnPls to D16:0/18:0 ratio exhibited a significant dementia effect. The EtnPls to D16:0/18:0 ratios of all eight Etns were significantly lower in the severely demented group relative to the low group while six of the eight were significantly lower in the severe group relative to the moderate group Example 5: Population Distributions as a Function of Dementia Severity The EtnPls 16:0/22:6 to PtdEt 16:0/18:0 ratio (DHA-EtnPls) showed the strongest overall sex-independent dementia effect (Tables 21b, 24b) and was used for all subsequent population distributions and comparisons. A summary of the key comparisons using this ratio are listed in Table 30. This ratio was then log(2) transformed and used to create a population histogram for each cohort of increasing cognitive impairment (FIG. 4). A cut-off value was selected based upon the findings of Bennett et al (8), (i.e. ~30% of the CN group being detected as SDAT) (FIG. 4, dotted line). Using this cut-off, 63%, 79% and 83% of low, moderate and severely demented subjects, respectively, were subsequently classified as SDAT. To compare these distributions with the known distributions of Aβ pathology in SDAT, we combined the results of four prospective pathology studies (5-8) to generate the theoretical population distributions of Aβ pathology in demented and non-demented populations assuming that Aβ is normally distributed in each population (FIG. 5A). These studies reported that only 71% (140/198) of clinically diagnosed SDAT subjects have SDAT pathology at death and that 32% (87/268) of cognitively normal subjects meet neuropathological criteria for SDAT at death. When the data from all of our cognitively tested subjects were combined, 32% (22/68) of our non-demented population and 75% (192/256) of our demented population were classified as SDAT positive based upon their serum EtnPls level (FIG. 5B). This comparison revealed that the observed distribution of depleted DHA-EtnPls perfectly matched the theoretical distribution of SDAT pathology in demented and non-demented subjects.

Example 6: Linear Extrapolation of Disease Progression and Serum EtnPls Depletion The data in FIGS. 3A-B suggests a strong correlation between the decrease in EtnPls and increasing dementia in the clinically diagnosed SDAT population. To investigate this concept in detail, we performed a linear regression analysis using the mean DHA-EtnPls level (normalized to CN) of each of the dementia cohorts and the average ADAS-cog score for each of these three cohorts (FIG. 6). A very high correlation was observed between the mean DHA-EtnPls level and the mean ADAS-cog scores of the three dementia cohorts ($r^2$=0.99). However, this linear decrease did not extrapolate back to the CN group (X vs. CN). Assuming a clinical SDAT progression of 7.5 ADAS-cog units per year this extrapolation predicts that that DHA-EtnPls levels begin to decline approximately seven years before clinical cognitive impairment (ADAS-cog=15) is evident.

Example 7: The Effect of Chronological Age on Serum DHA-EtnPls Levels

Figure 7A:
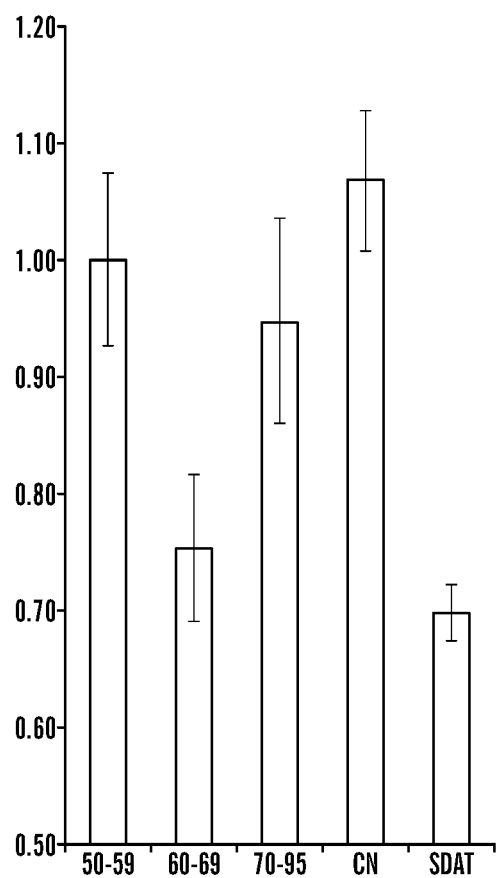
FIGS. 7A-7B show serum DHA-EtnPls (EtnPls 16:0/22:6 to PtdEt 16:0/18:0 ratio) levels in SDAT, Cognitive Normal (CN), and general population subjects.
Figure 7B:
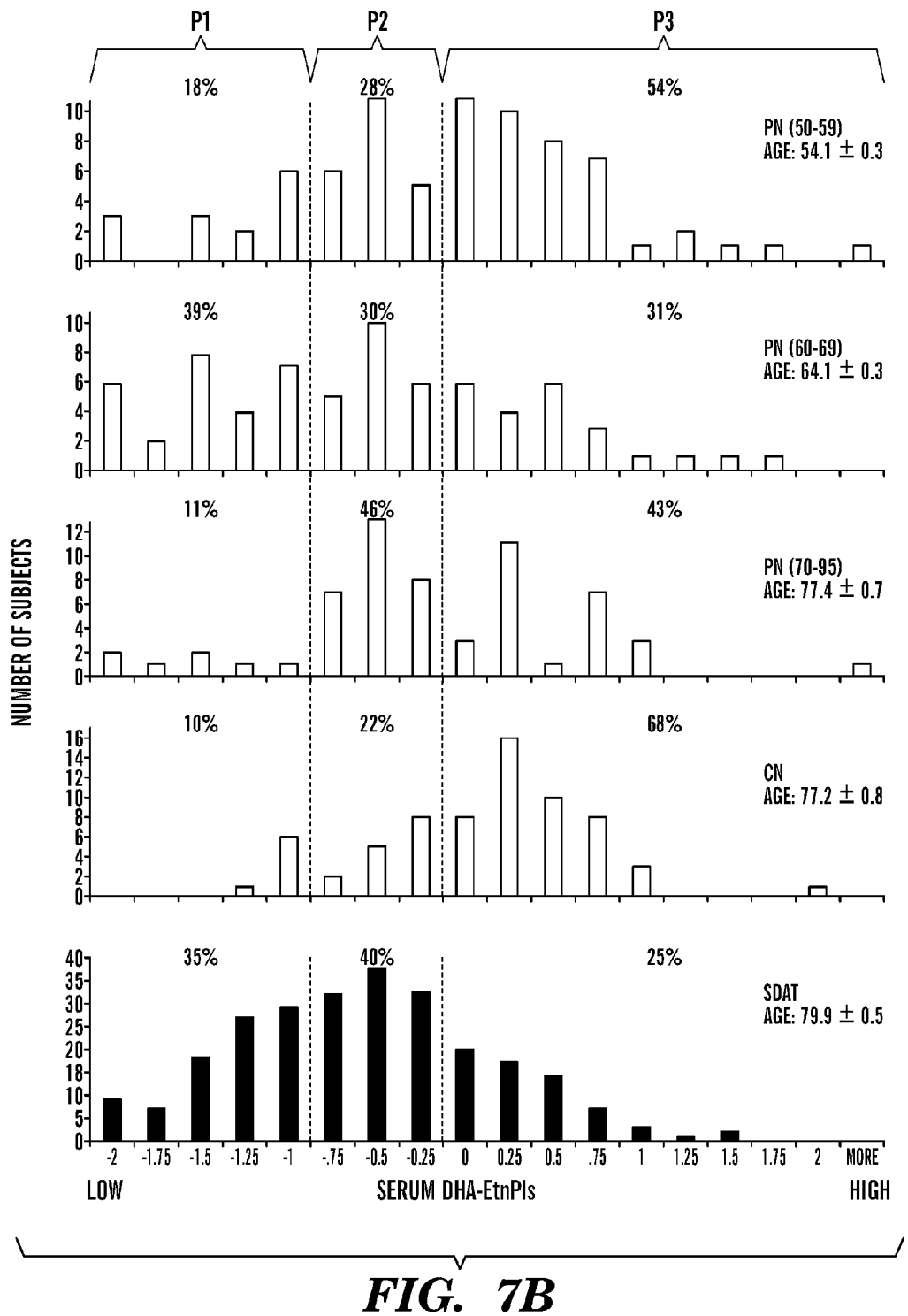

To investigate whether the above prediction could be verified experimentally, we determined the serum DHA-EtnPls levels in 209 subjects (110 male, 99 female, Table 1) of unknown cognitive status but currently not diagnosed with dementia, and compared these groups to the clinical SDAT and CN cohorts (FIGS. 7A-B). The results of this analysis revealed a significant drop in serum DHA-EtnPls in the aged 60-69 cohort versus the aged 50-59 cohort (FIG. 7A). This cohort also had significantly lower levels versus the CN group even though the CN group was, on average, 13 years older. Interestingly, the aged 70-95 cohort was not significantly different from either the aged 50-59 cohort or the CN cohort, but had significantly higher levels than the SDAT cohort.

Example 8: Sub-Populations Identified by Serum DHA-EtnPls Levels

We next examined the distribution of serum DHA-EtnPls within each age group, as shown in FIG. 7B. The population distributions of the five groups (three age groups, CN and SDAT) differentiated by age and dementia status reveal the presence of three distinct populations (P1-P3, FIG. 7B). Using the conceptual framework introduced by Katzman et al (6), who observed that cognitively normal subjects with SDAT pathology had intermediate choline acetyltransferase (ChAT) activities relative to cognitively normal subjects without SDAT pathology and demented subjects with SDAT pathology. This middle group was said to have "reserve". Therefore, we interpreted our populations as: P1—subjects with SDAT pathology and no remaining reserve capacity; P3—subjects with little or no SDAT pathology; P2—subjects that are transitioning from P3 to P1. These P2 subjects are hypothesized to have SDAT pathology and some level of reserve remaining. Since SDAT subjects have a life expectancy of less than 10 years from diagnosis (16, 17) and low DHA-EtnPls are highly associated with SDAT severity, the decreased number of P1 subjects observed in the aged 70-95 cohort is most likely due to differences in life expectancy between P1 and P2 or P3. The transitory nature of P2 is best illustrated by examining the different ratios between the percentages of subjects present in P3 compared to P2, as observed in the lower three panels of FIG. 7B. These three cohorts differ only in dementia status. The P3 to P2 ratio changes from 3:1 (68% versus 22%) in the confirmed cognitive normal group to an intermediate ratio of 1:1 (43% versus 46%) in the normal healthy elderly group of unknown cognitive status, to 0.6:1 (25% versus 40%) in the confirmed demented SDAT cohort.

Example 9: High Throughput Commercial Method Development

The present invention also provides high throughput methods for differential diagnosis of SDAT dementia and non-SDAT dementia states. The method involves fragmentation of the parent molecule; in a non-limiting example, this may be accomplished by a Q-Trap™ system. Detection of the metabolites may be performed using one of various assay platforms, including colorimetric chemical assays (UV, or other wavelength), antibody-based enzyme-linked immunosorbant assays (ELISAs), chip-based and polymerase-chain reaction for nucleic acid detection assays, bead-based nucleic-acid detection methods, dipstick chemical assays or other chemical reaction, image analysis such as magnetic resonance imaging (MRI), positron emission tomography (PET) scan, computerized tomography (CT) scan, nuclear magnetic resonance (NMR), and various mass spectrometry-based systems.

Figure 8:
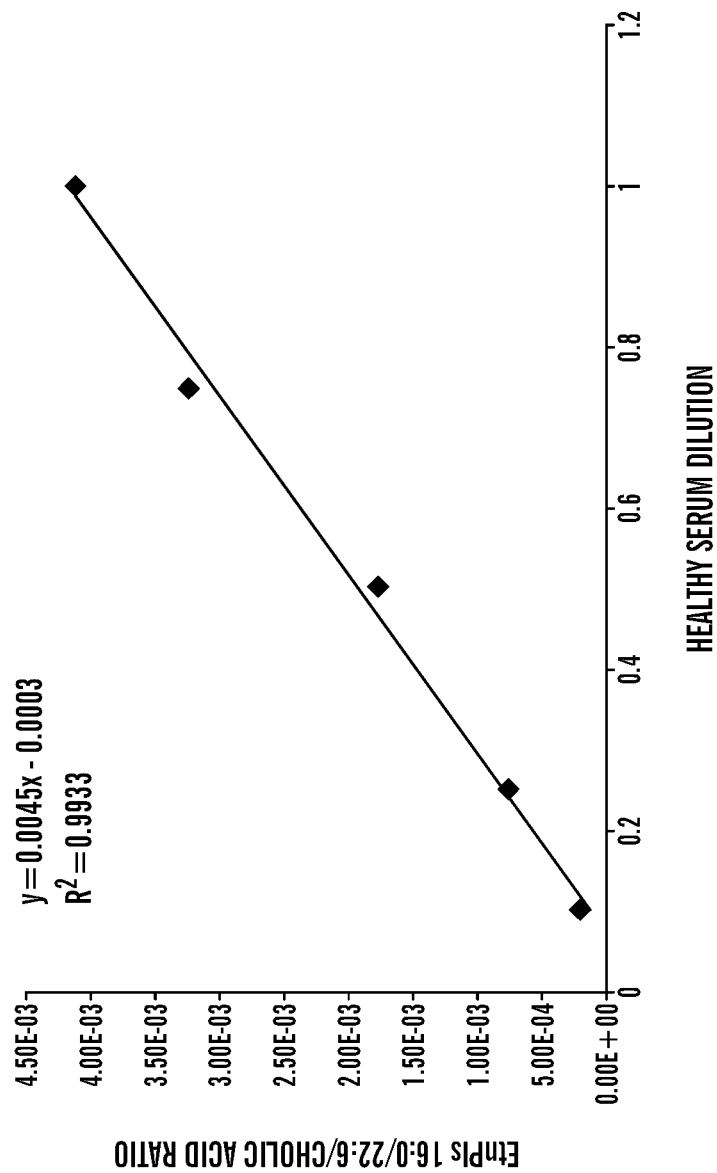
FIG. 8 is a Q-Trap flow injection analysis standard curve of EtnPls 16:0/22:6 in healthy human serum.

High throughput screening (HTS) was performed with a linear ion trap mass spectrometer (Q-trap 4000, Applied Biosystem) coupled with Agilent 1100 LC system. Sample was prepared by adding 15 uL of internal standard (5 μg/mL of (24-13C)-Cholic Acid in methanol) to 120 uL ethyl acetate fraction of each sample. 100 ul sample was injected by flow injection analysis (FIA), and monitored under negative APCI mode. The method was based on multiple reaction monitoring (MRM) scan mode of one parent/daughter transition for each metabolite and one internal standard. Each transition was scanned for 70 ms for a total cycle time of 2.475 sec. The isocratic 10% EtOAc in MeOH elution was performed with a flow rate at 360 μl/min for 1 min. The source parameters were set as follows: CUR: 10.0, CAD: 8, NC: −4.0, TEM: 400, GS1: 30, GS2: 50, interface heater on. The compound parameters were set as follows: DP: −120.0, EP: −10, NC: −4.0, CE: −40, CXP: −15. FIG. 8 illustrates a representative standard curve for this method for EtnPls 16:0/22:6 generated by diluting a normal serum sample while maintaining a constant concentration of internal standard (24-13C)-Cholic Acid).

Example 10: Structure Elucidation of the Metabolite Biomarkers

Organic extracts of human serum taken from normal and Alzheimer's disease patients were analyzed using FT-ICRMS and LC/MS techniques. Three metabolites, which were significantly higher in intensity in extracts from healthy subjects compared to those from disease subjects transition can be determined for any ethanolamine phospholipid by using a combination of the parent ion mass and the fragment mass of the moiety at either the sn-1 or sn-2 position.

Example 11: Synthesis of the Compounds of the Present Invention

Figure 9:
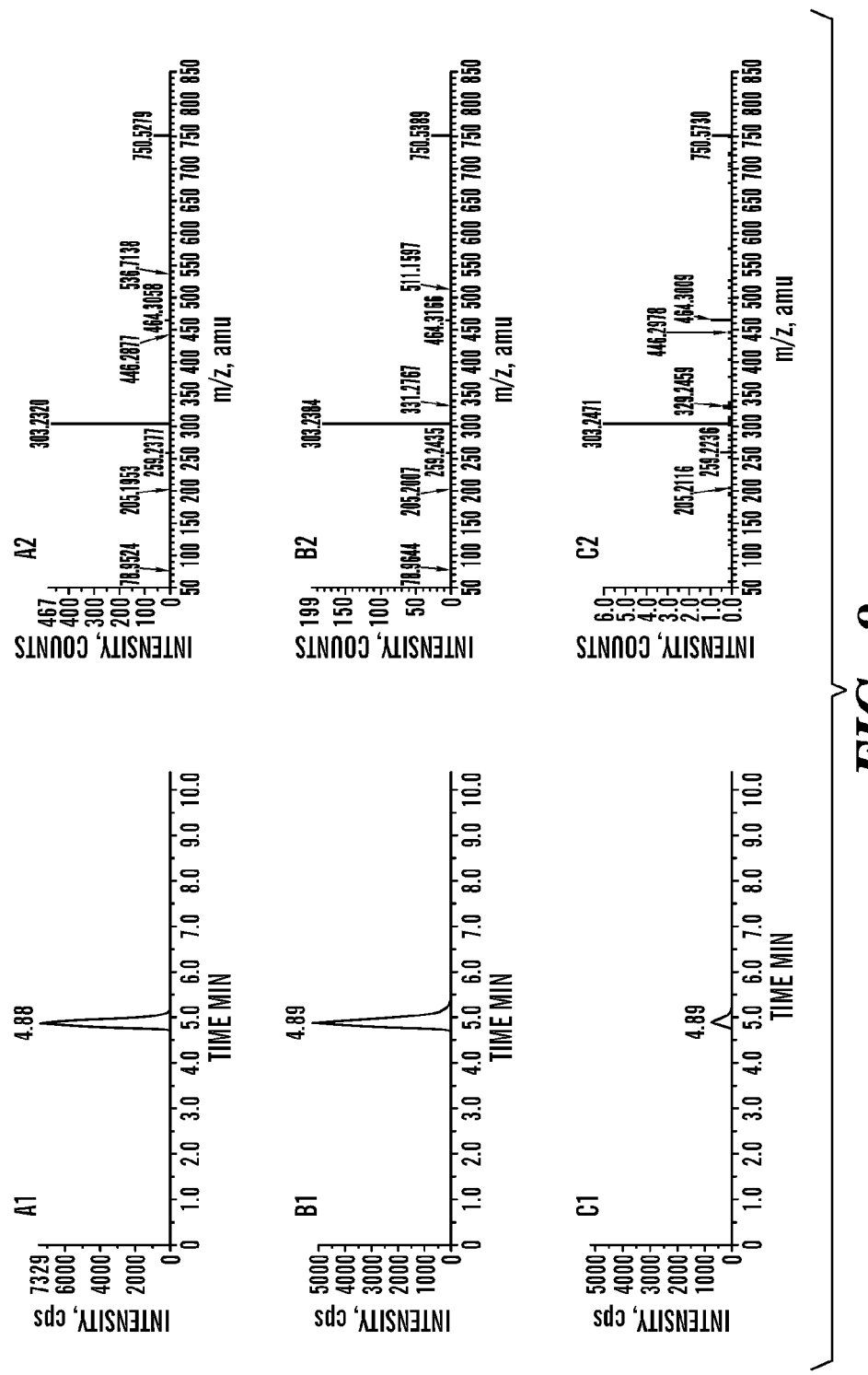
FIG. 9 is a panel of chromatograms showing LC-MS and MS/MS analysis of EtnPls 18:0/20:4. Panel A1—Extracted ion chromatogram (EIC) of mass 750 (M–H—) of a pure standard; panel A2—MS/MS spectra of parent ion M/Z 750 @ retention time 4.8-5.0 minutes. Panel B1—EIC of 750 from a cognitively normal subject; panel B2—MS/MS spectra of M/Z 750 @ 4.8-5.0 min. Panel C1—EIC of 750 from a SDAT subject; panel C2—MS/MS spectra of M/Z 750 @ 4.8-5.0 min.
Figure 10:
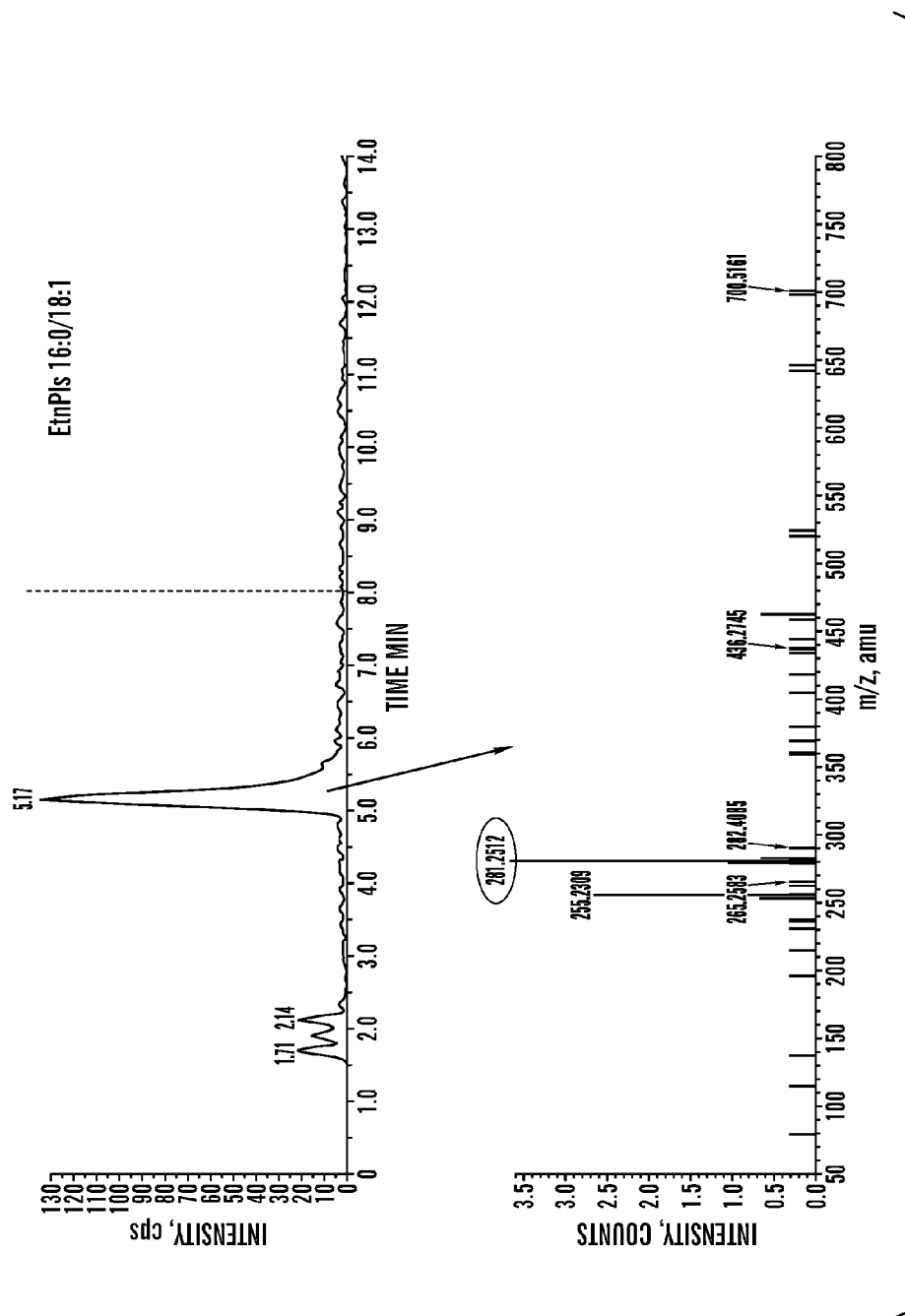
FIG. 10 shows an extracted ion chromatogram (upper panel) and MS/MS spectrum (lower panel) of EtnPls 16:0/18:1 in human serum.
Figure 11:
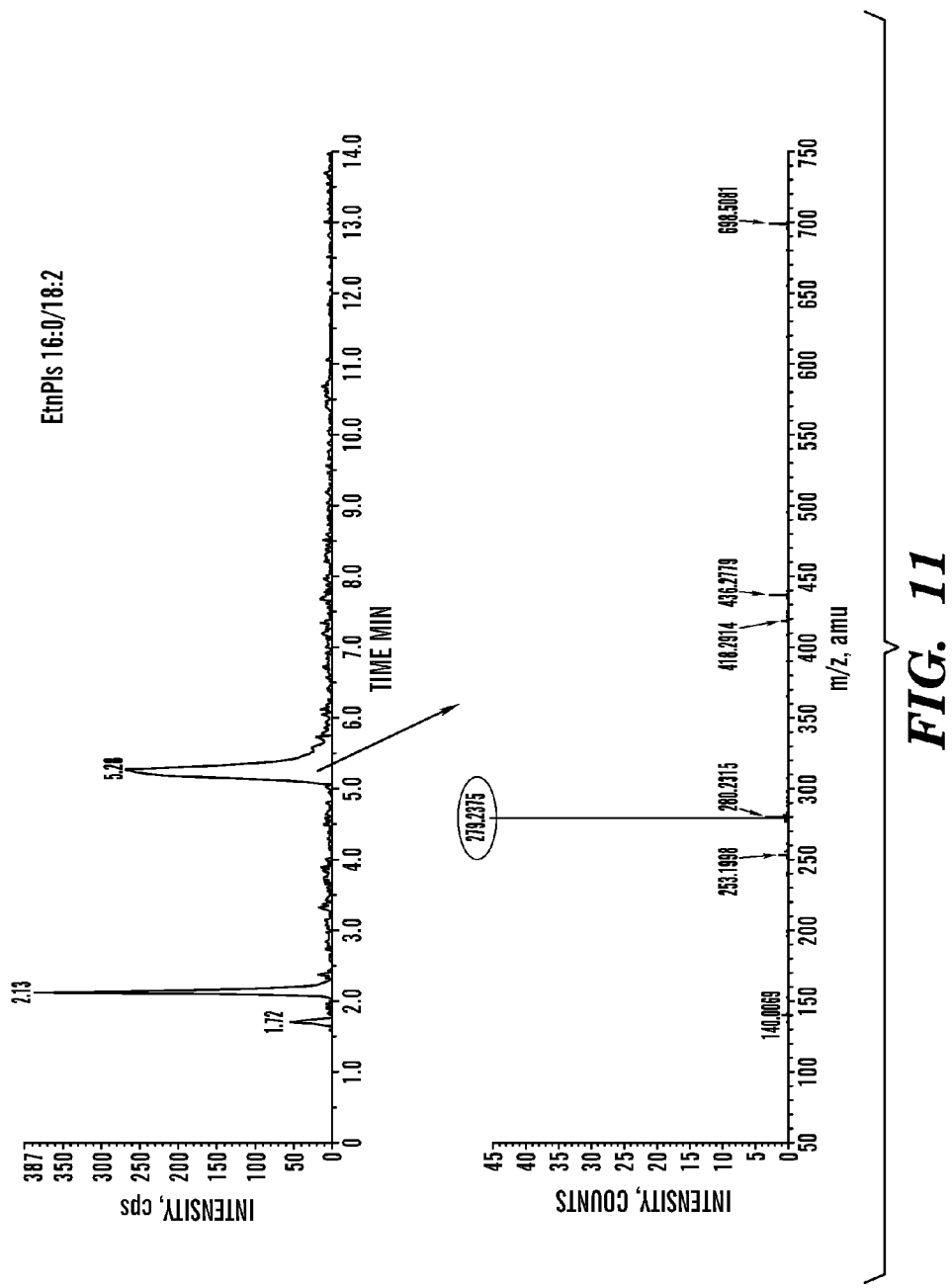
FIG. 11 shows an extracted ion chromatogram (upper panel) and MS/MS spectrum (lower panel) of EtnPls 16:0/18:2 in human serum.
Figure 12:
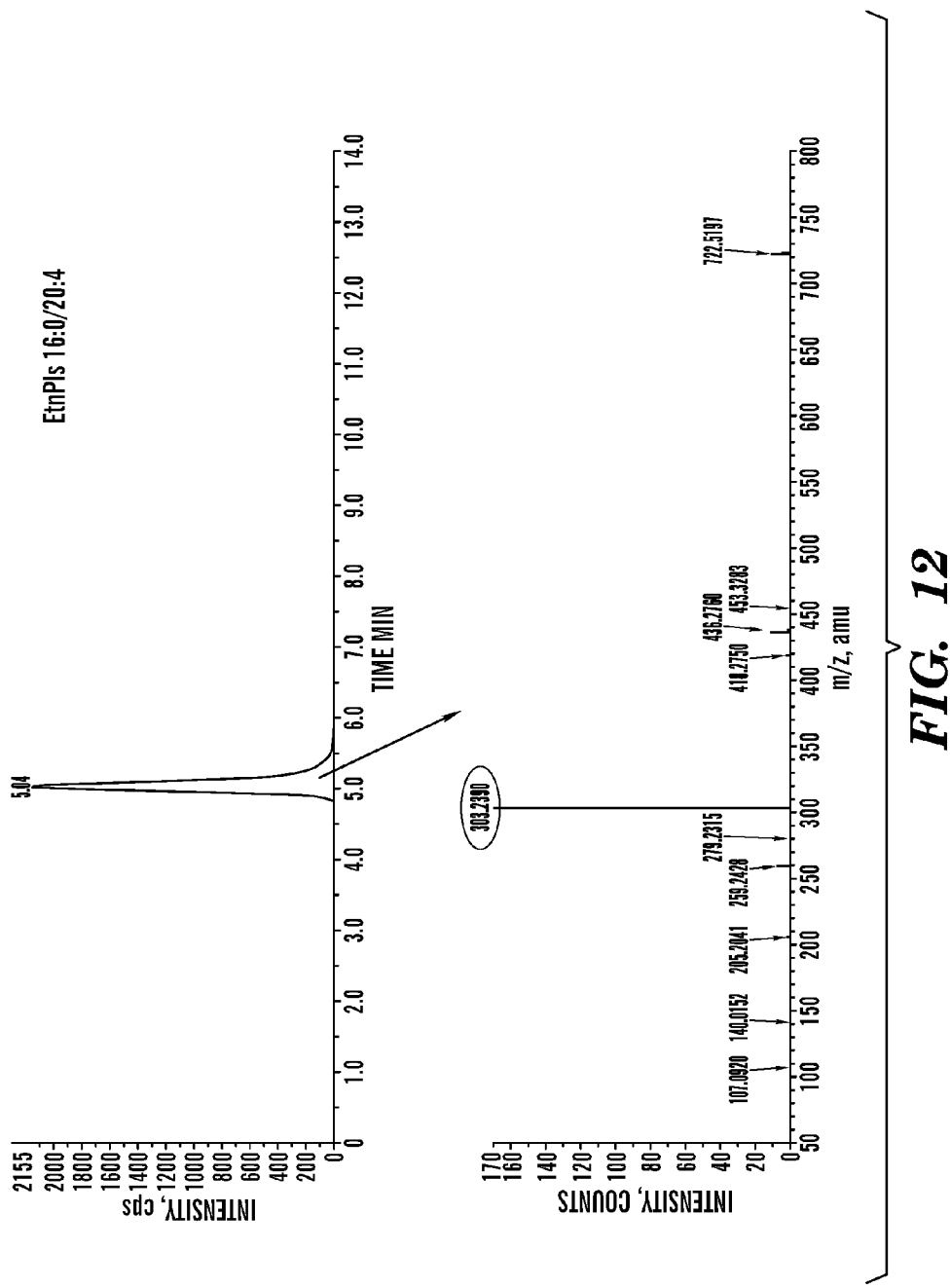
FIG. 12 shows an extracted ion chromatogram (upper panel) and MS/MS spectrum (lower panel) of EtnPls 16:0/20:4 in human serum.
Figure 13:
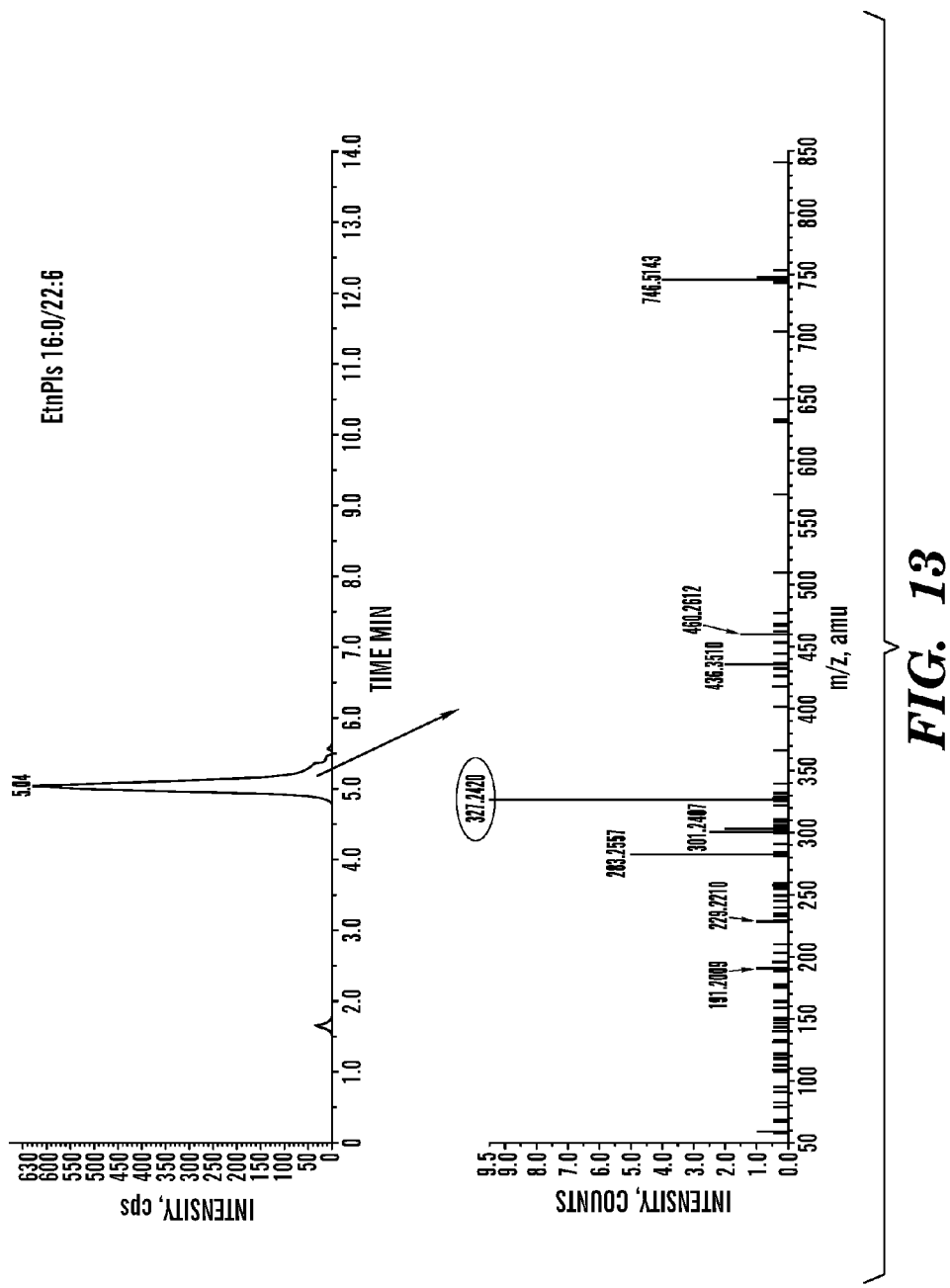
FIG. 13 shows an extracted ion chromatogram (upper panel) and MS/MS spectrum (lower panel) of EtnPls 16:0/22:6 in human serum.
Figure 14:
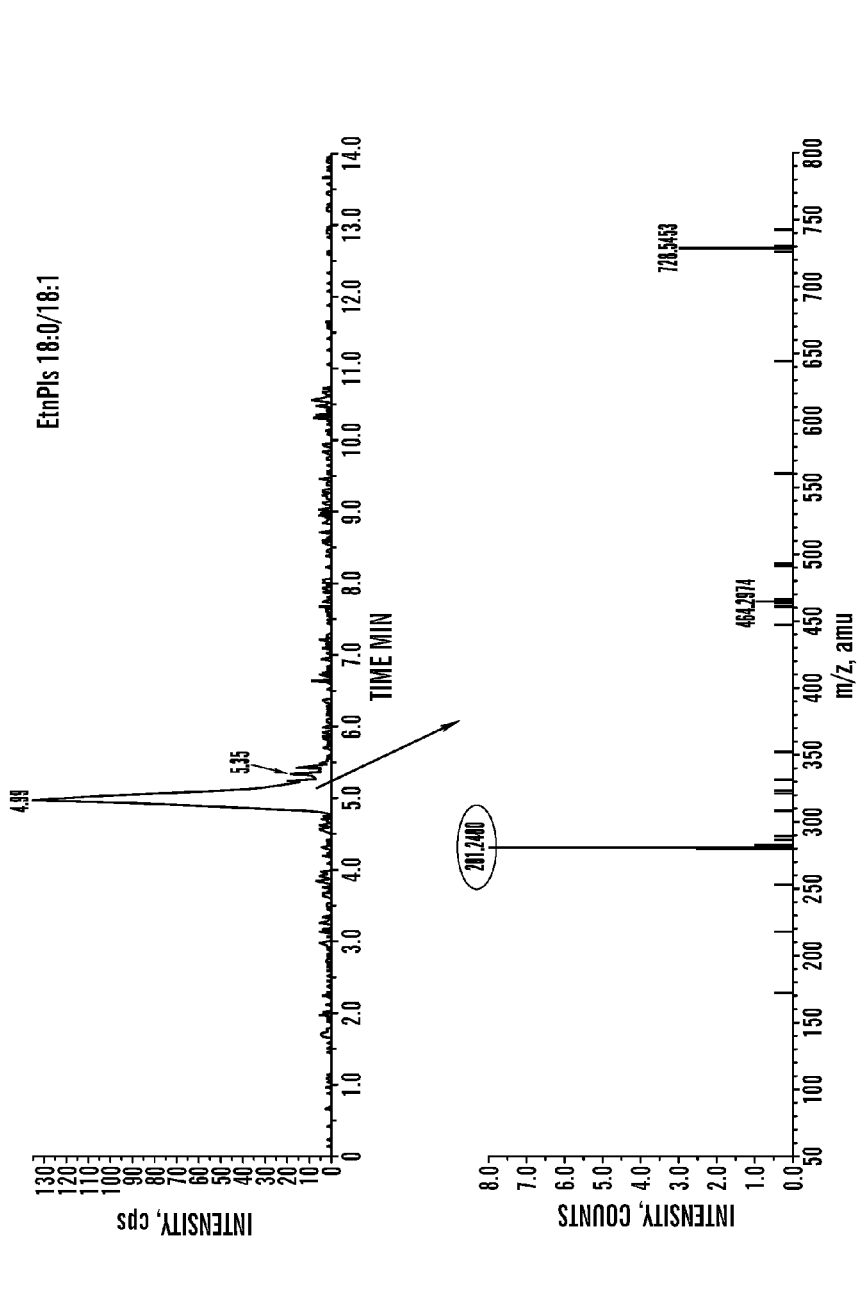
FIG. 14 shows an extracted ion chromatogram (upper panel) and MS/MS spectrum (lower panel) of EtnPls 18:0/18:1 in human serum.
Figure 15:
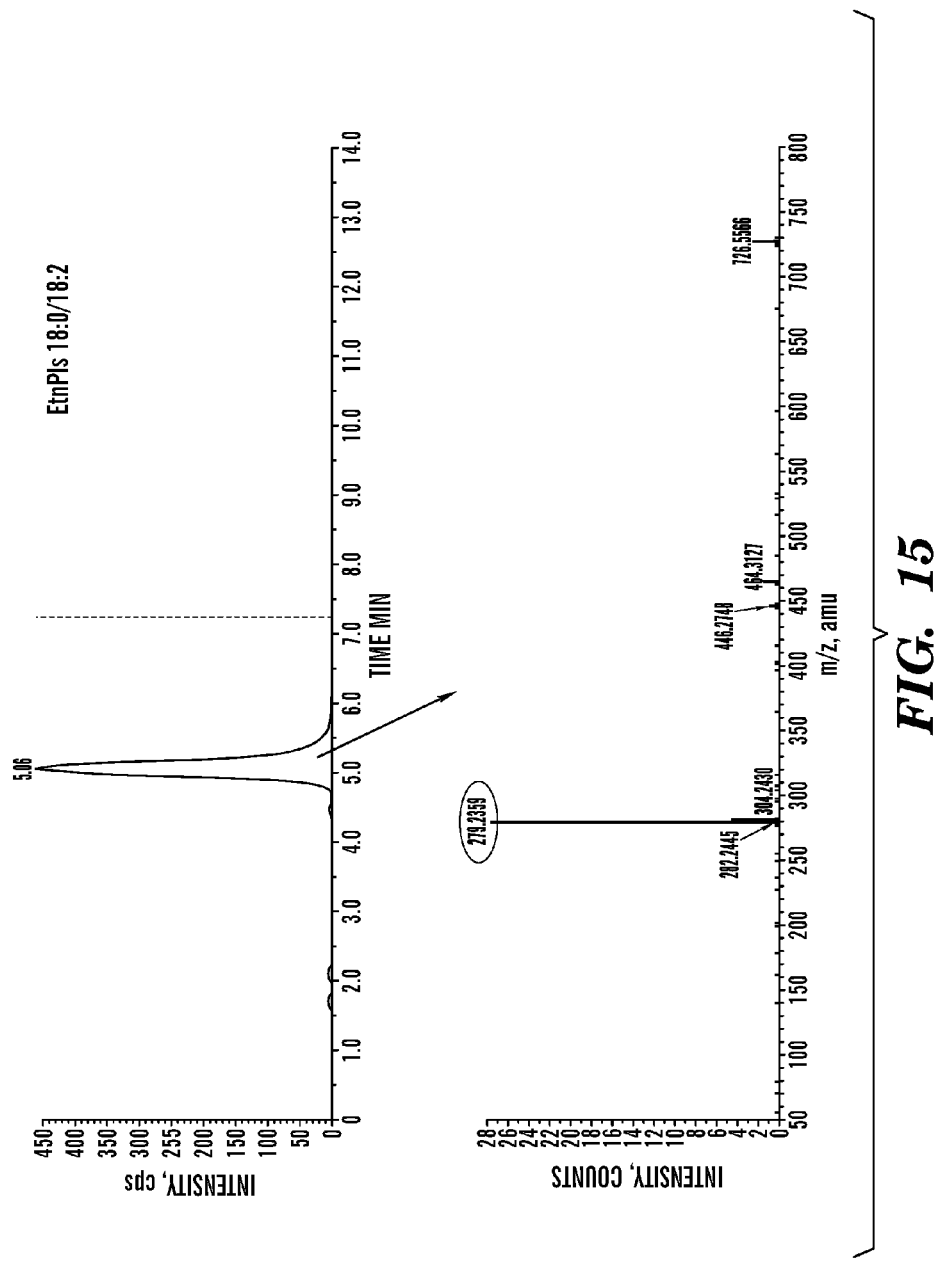
FIG. 15 shows an extracted ion chromatogram (upper panel) and MS/MS spectrum (lower panel) of EtnPls 18:0/18:2 in human serum.
Figure 16:
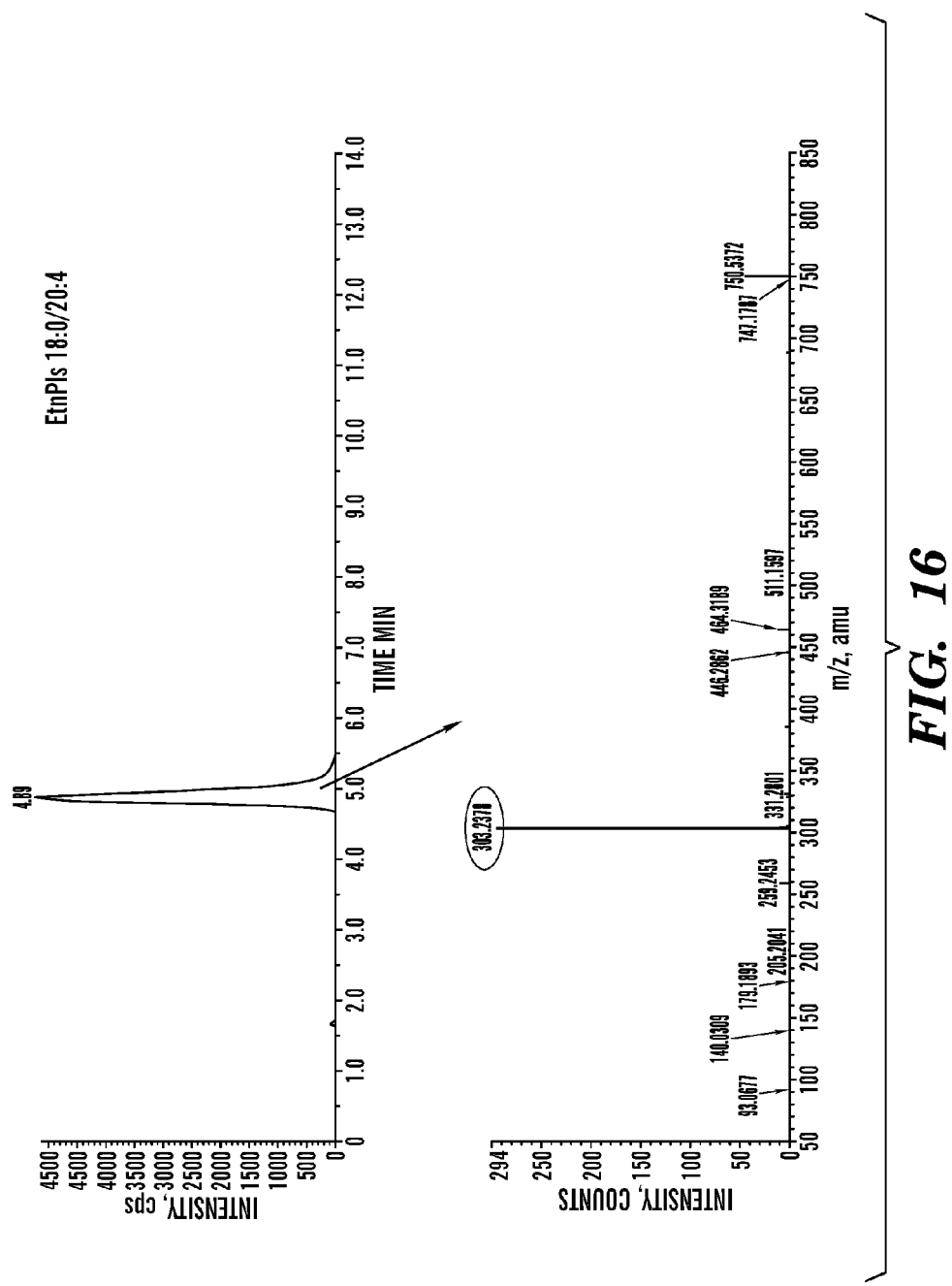
FIG. 16 shows an extracted ion chromatogram (upper panel) and MS/MS spectrum (lower panel) of EtnPls 18:0/20:4 in human serum.
Figure 17:
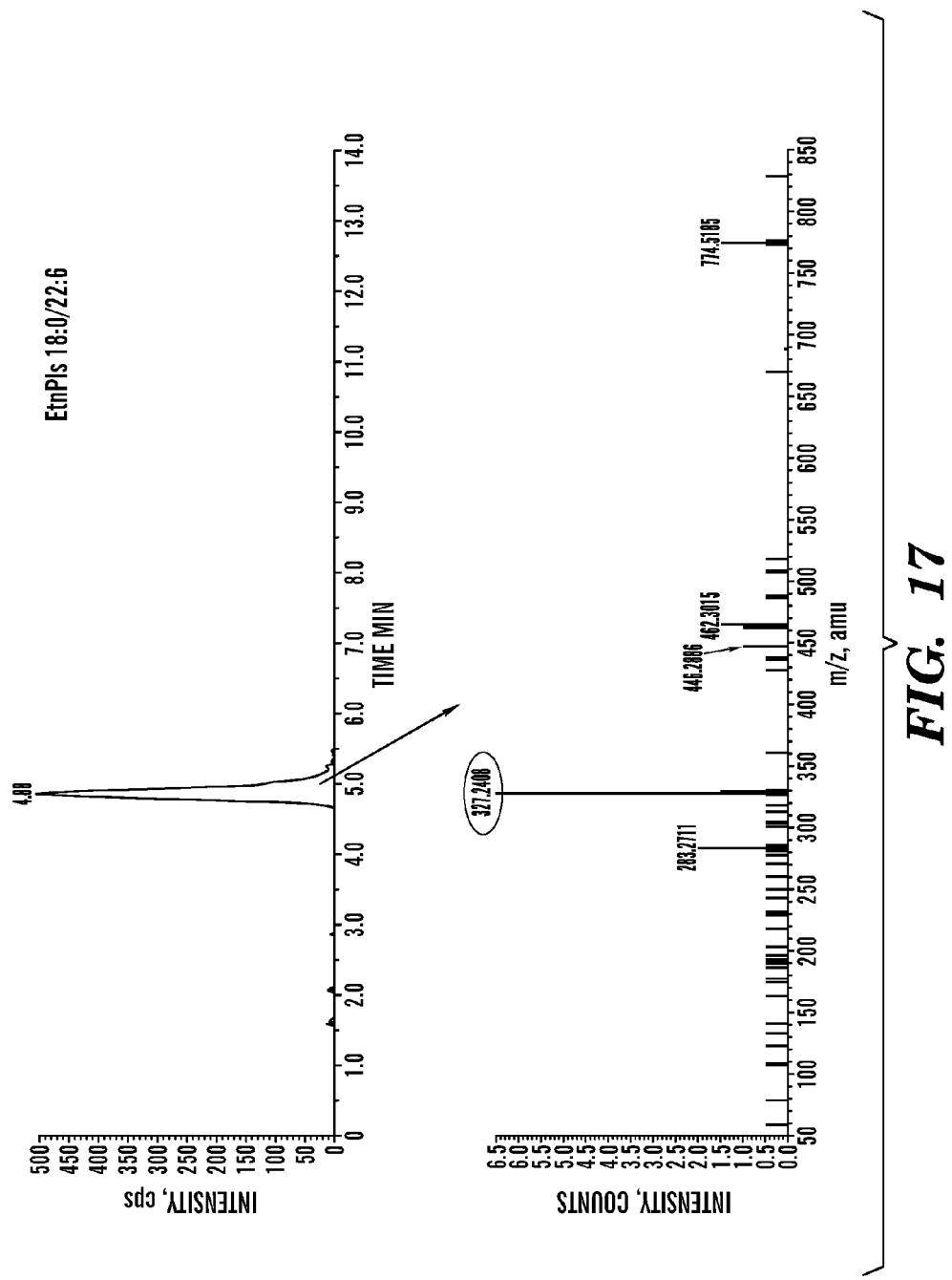
FIG. 17 shows an extracted ion chromatogram (upper panel) and MS/MS spectrum (lower panel) of EtnPls 18:0/22:6 in human serum.
Figure 18:
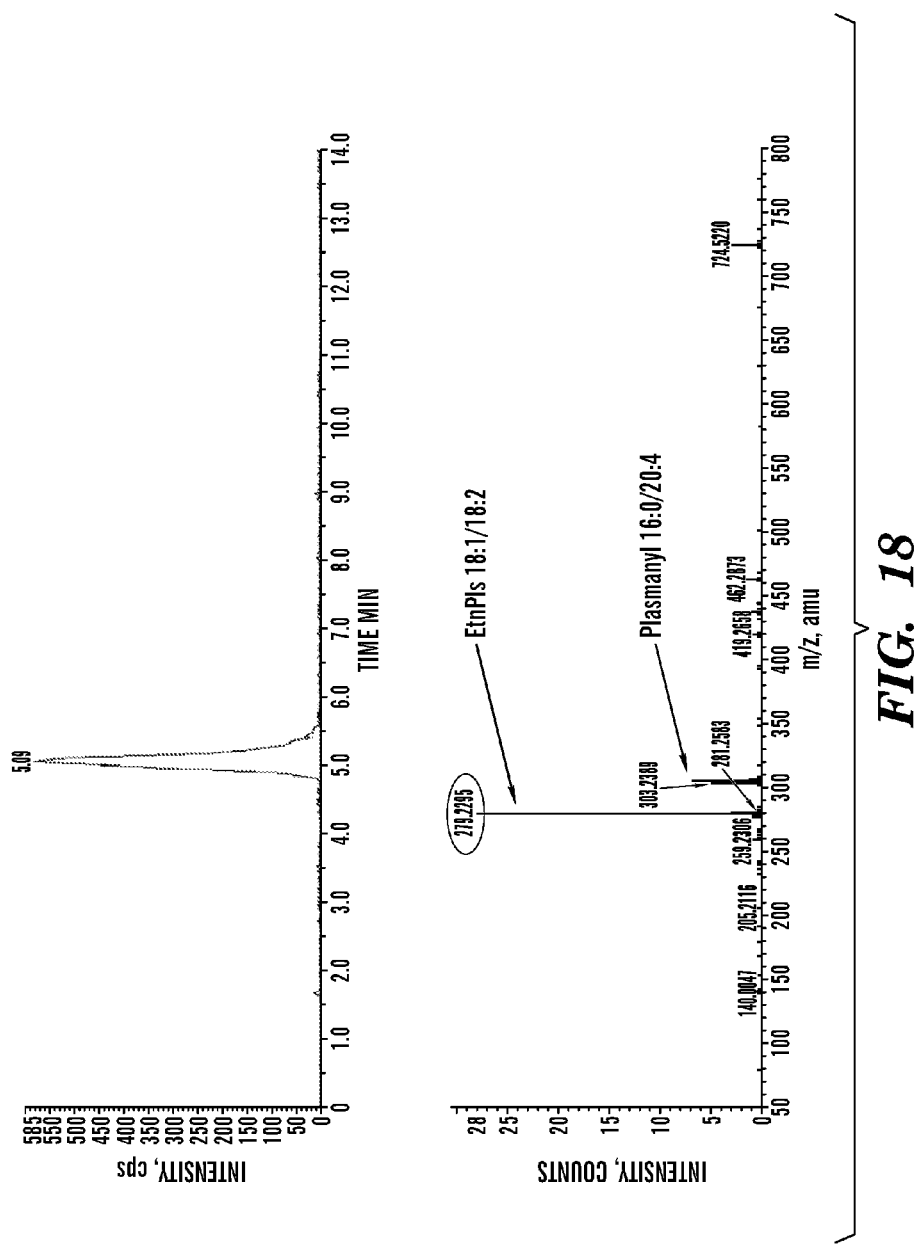
FIG. 18 shows an extracted ion chromatogram (upper panel) and MS/MS spectrum (lower panel) of EtnPls 18:1/18:2 and Plasmanyl 16:0/20:4 in human serum.
Figure 19:
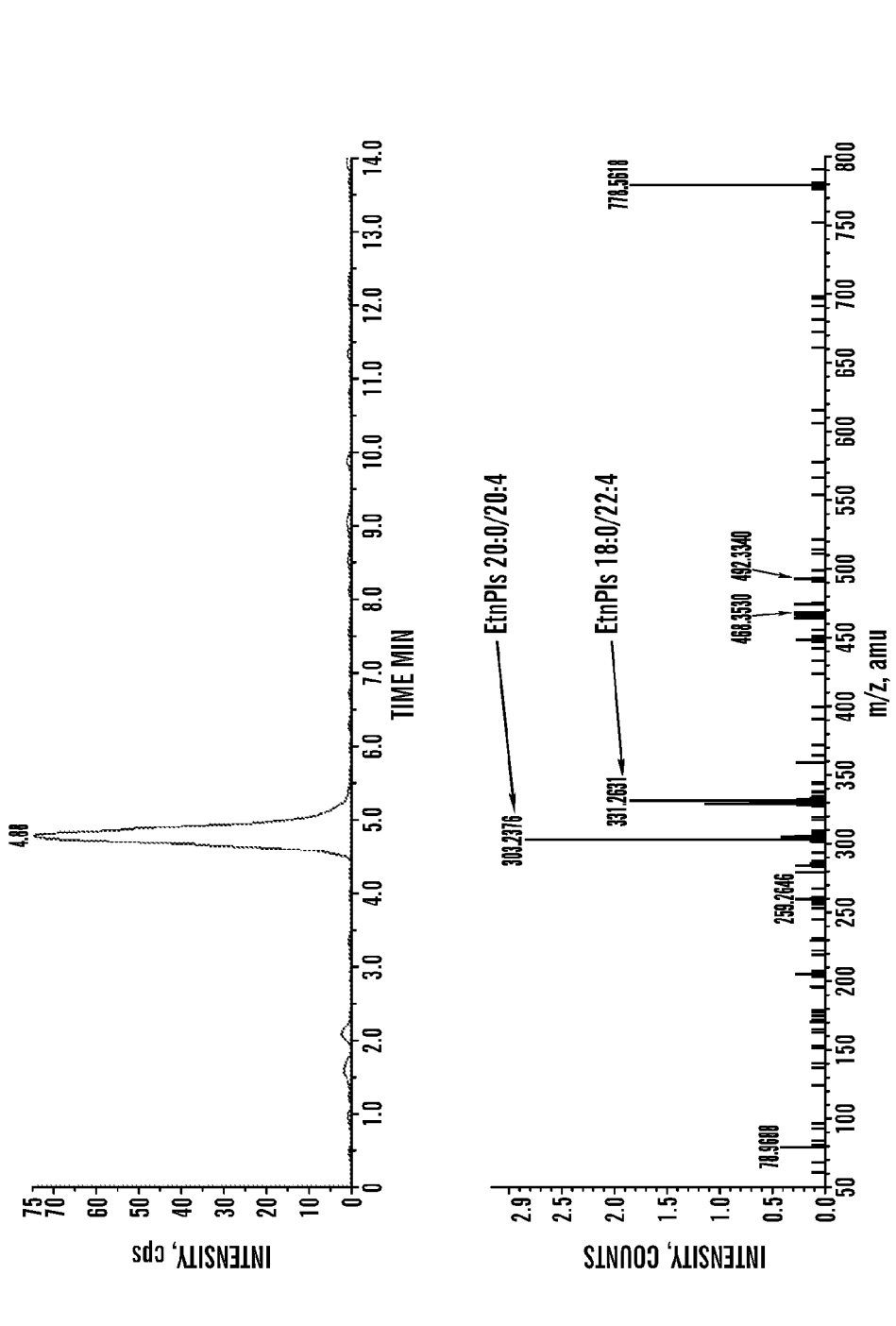
FIG. 19 shows an extracted ion chromatogram (upper panel) and MS/MS spectrum (lower panel) of EtnPls 20:0/20:4 and EtnPls 18:0/22:4 in human serum.
Figure 20:
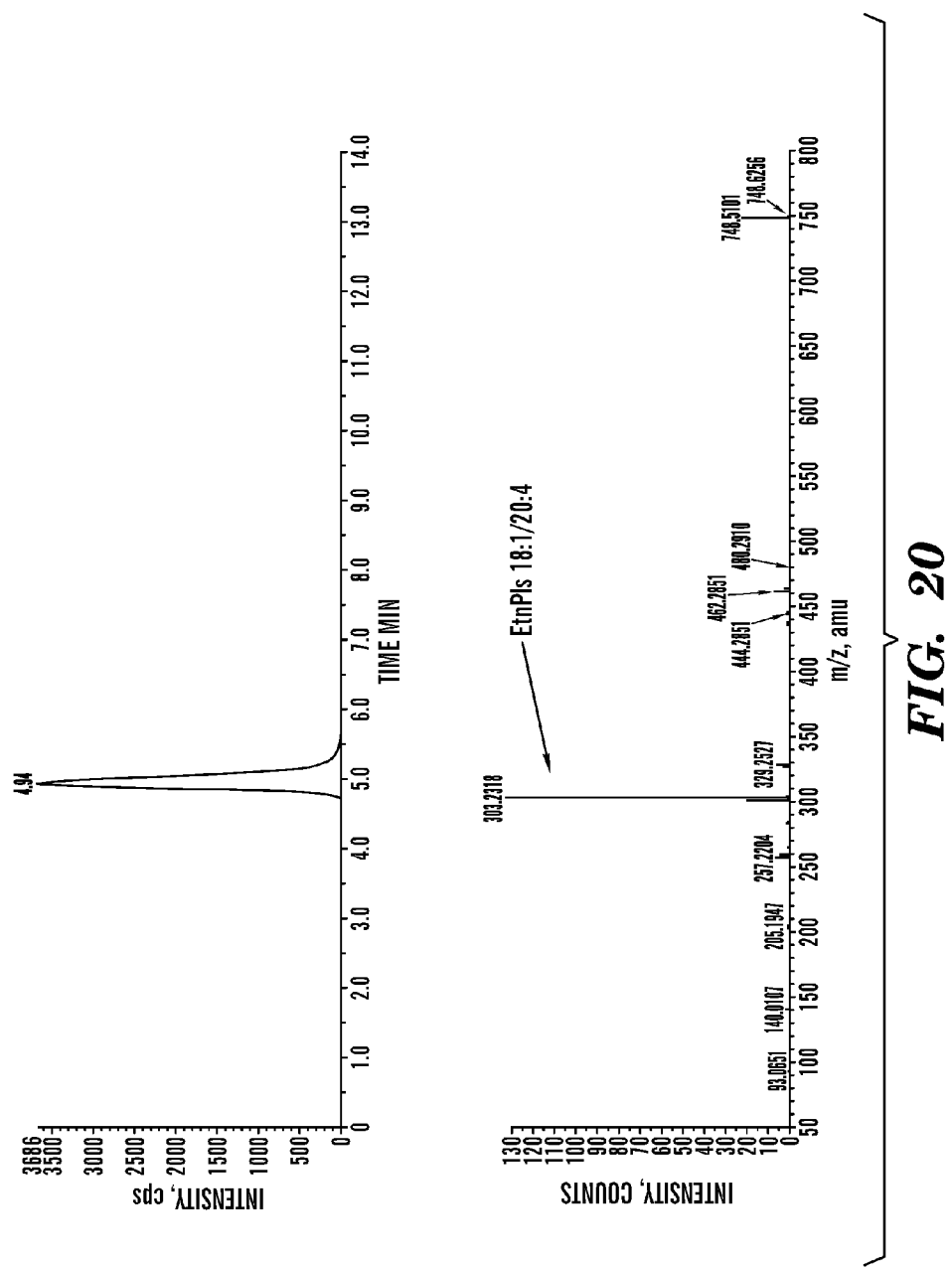
FIG. 20 shows an extracted ion chromatogram (upper panel) and MS/MS spectrum (lower panel) of EtnPls 18:1/20:4 in human serum.
Figure 21:
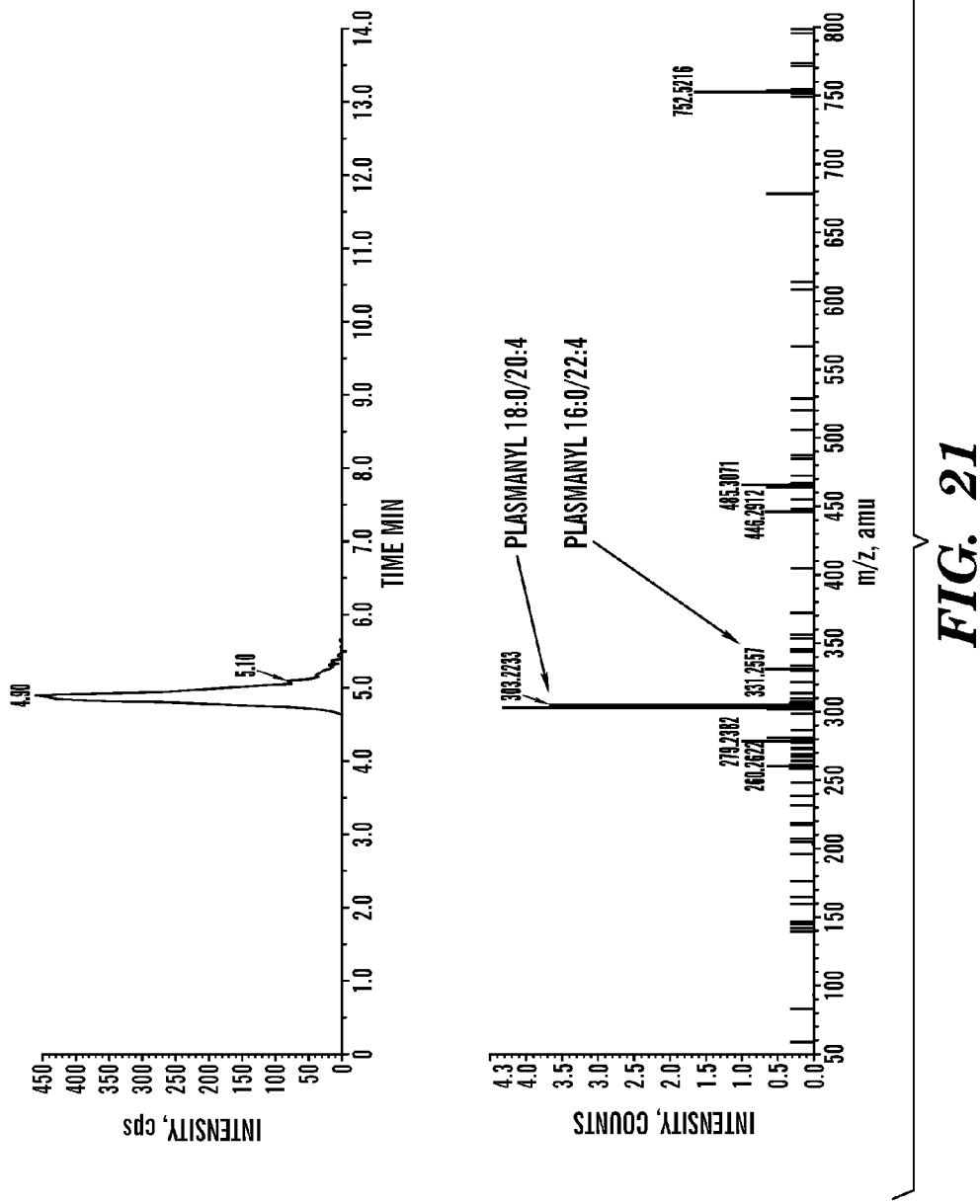
FIG. 21 shows an extracted ion chromatogram (upper panel) and MS/MS spectrum (lower panel) of Plasmanyl 18:0/20:4 and Plasmanyl 16:0/22:4 in human serum.
Figure 22:
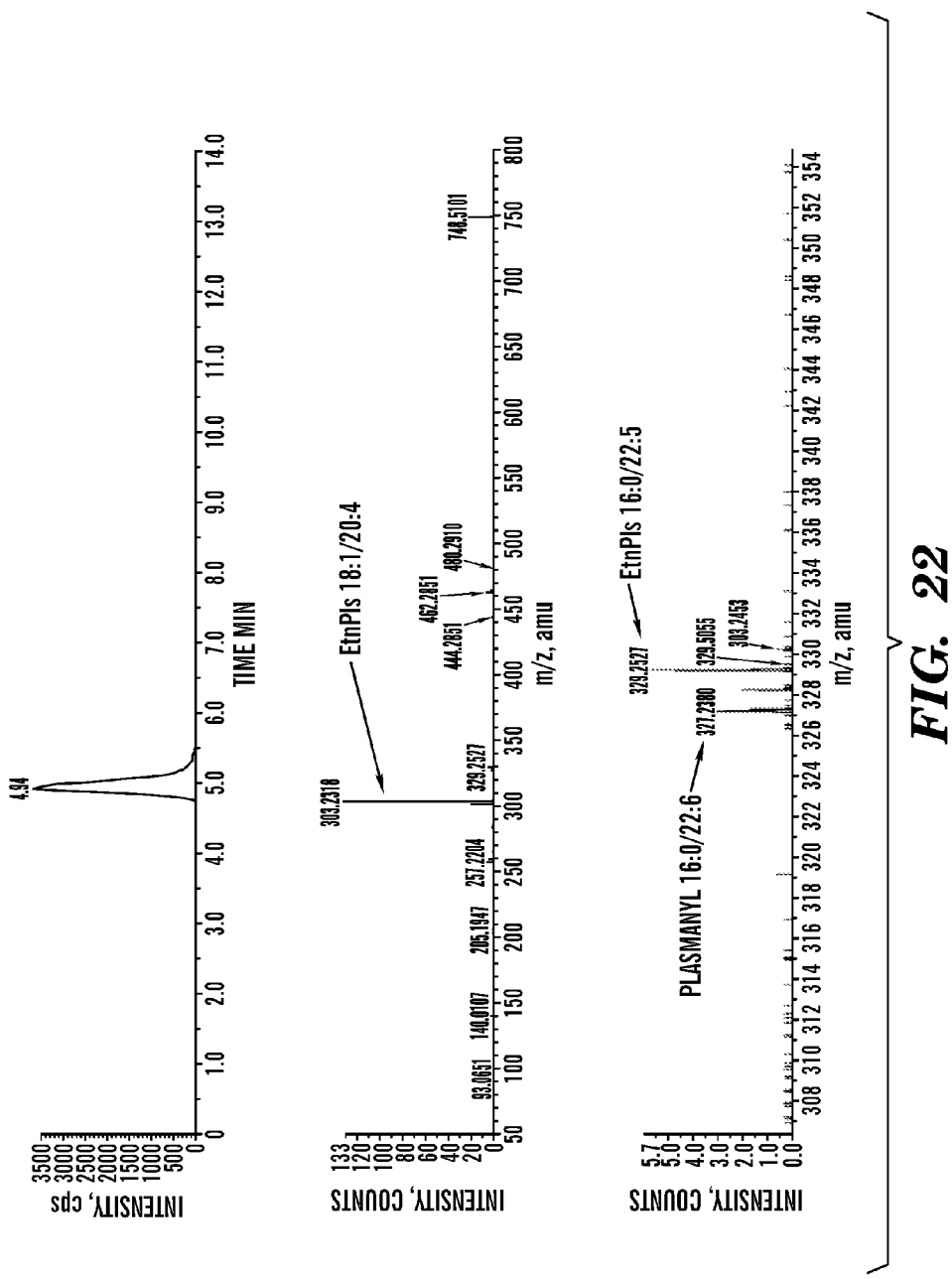
FIG. 22 shows an extracted ion chromatogram (upper panel) and MS/MS spectrum (lower panels) of EtnPls 18:1/20:4, EtnPls 16:0/22:5, Plasmanyl 16:0/22:6 in human serum.

One compound on the present invention; (4Z,7Z,10Z, 13Z,16Z,19Z)-1-(hexadecyloxy)-3-hydroxypropan-2-yl docosa-4,7,10,13,16,19-hexanenoate (Formula 5a) was prepared according to the following synthetic strategy:

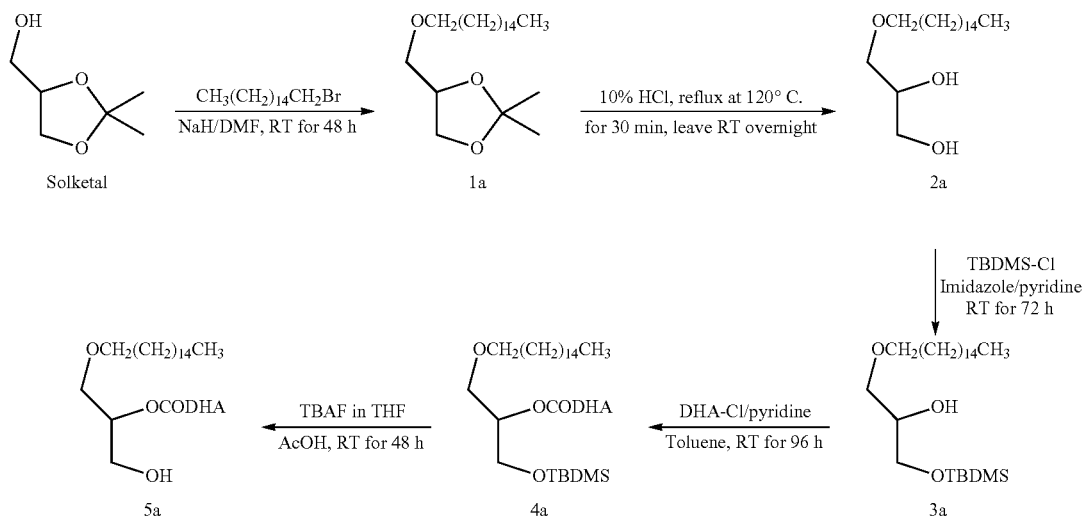

were detected and structurally elucidated. The molecular formula of metabolite 1 was determined as $C_{43}H_{78}NO_7P$ by HRAPCI-MS (FIGS. 24A-D). MS/MS spectral analysis was used to deduce the structure. The strong MS/MS fragment ion at m/z 303 and other fragment ions due to loss of sn-2 acyl group (m/z 464) as a ketone, loss of the sn-1 vinyl ether side chain (m/z 482) though small, and the fragment ion due to phosphoethanolamine (m/z 140) suggested it to be a plasmenyl phosphatidylethanolamine type molecule with arachidonic acid at the sn-2 position. Based on these deductions, the structure of metabolite 1 was elucidated as 1-O-1'-(Z)-octadecenyl-2-arachidoyl-sn-glycero-3-phosphoethanolamine. The structure of 1 was confirmed as 1-O-1'-(Z)-octadecenyl-2-arachidoyl-sn-glycero-3-phosphoethanolamine (commercial standard) by comparison of their LC/MS and MS/MS spectral data (FIG. 9)

The two remaining metabolites with molecular formulae $C_{39}H_{74}NO_7P$ and $C_{41}H_{74}NO_7P$ determined by HRAPCI-MS, found to co-elute with 1 in LC/MS, and analyzed using MS/MS showed fragment ions and fragmentation patterns similar to those of 1. These metabolites were thought to be very similar in structure to 1 and thus their structures were proposed as 1-O-1'-(Z)-hexadecenyl-2-linoleyl-sn-glycero-3-phosphoethanolamine (2) and 1-O-1'-(Z)-hexadecenyl-2-arachidoyl-sn-glycero-3-phosphoethanolamine (3) respectively.

FIGS. 10-22 illustrate the retention time, MS/MS fragmentation patterns, and putative structures for selected molecules. Due to the conserved MS/MS fragmentation mechanism between these molecules, the theoretical MS/MS All chemicals and solvents were purchased from Sigma-Aldrich Canada Ltd., Oakville, ON., Canada, VWR Canada and Nu-Chek Prep., Elysian, Minn. All solvents used were anhydrous. Analytical thin layer chromatography (TLC) was carried out on precoated silica gel TLC aluminum sheets (EM science, Kieselgel 60 $F_{254}$, 5×2 cm×0.2 mm). Compounds were visualized under UV light (254/366 nm) or placed in iodine vapor tank and by dipping the plates in a 5% aqueous (w/v) phosphmolybdic acid solution containing 1% (w/v) ceric sulfate and 4% (v/v) $H_2SO_4$, followed by heating. Flash column chromatography was carried out using silica gel, Merck grade 60, mesh size 230-400, 60 A°. NMR spectra were recorded on a Bruker Avance spectrometers; for $^1H$ (500 MHz), δ values were referenced to $CDCl_3$ ($CHCl_3$ at 7.24 ppm) and for $^{13}C$ NMR (125.8 MHz) referenced to $CDCl_3$ (77.23 ppm). Coupling constants (J) are reported to the nearest 0.5 Hz. High resolution mass spectral data were obtained on Bruker Apex 7T Fourier transform ion cyclotron resonance mass spectrometer (FT-ICRMS) with atmospheric pressure chemical ionization in the positive mode (HRAPCI-MS). Fourier transform infra-red (FTIR) spectra were recorded on Bio-Rad FTS-40 spectrometer using the diffuse reflectance method on samples dispersed in KBr.

Synthesis of cis-(±)-2-O-Docosahexaenoyl-1-O-hexadecylglycerol (5a) (±)-2,2-Dimethyl-4-(hexadecyloxymethyl)-1,3-dioxolane (1a)

To NaH (1.85 g, 60% dispersed in mineral oil) under argon was added anhydrous N, N-dimethylformamide (DMF, 30 mL) at RT. Solketal (2.20 g, 16.7 mol) in 10 mL anhydrous DMF was then added dropwise with constant stirring. 1-Bromohexadecane (5.10 g, 16.7 mol), dissolved in anhydrous DMF (20 mL) was then added to the reaction mixture dropwise and stirred for 72 hours. The reaction was quenched by adding about 5 mL of methanol. It was then poured into cold ice water (100 mL) and extracted with hexane (100 mL, 3×). The solvent was removed under reduced pressure and the residue chromatographed on silica gel using hexane-dichloromethane to obtain 1a (3.363 g, 57% yield); $^1$H NMR (in CDCl$_3$): δ in ppm 0.83-0.86 (3H, t, J=6.5 Hz), 1.22 (26H, m), 1.33 (3H, s), 1.39 (3H, s), 1.52-1.55 (2H, m), 3.37-3.48 (4H, m), 3.68-3.71 (1H, t, J=6.5 Hz), 4.01-4.03 (1H, t, J=6.5 Hz), 4.20-4.25 (1H, quintet, J=6.0 Hz); $^{13}$C NMR (in CDCl$_3$): δ in ppm 14.3, 22.9, 25.6, 26.2, 27.0, 29.6, 29.7, 29.8, 29.9, 32.1, 67.1, 72.0, 72.1, 74.9, 109.5.

(±)-1-O-Hexadecylglycerol (2a)

To compound 1a (3.363 g) was added 10% HCl solution (40 mL) and refluxed at 120° C. for 30 min. The reaction mixture was then kept at RT for 24 hours. The white lumps formed were filtered. The filtrate was extracted with hexane (50 mL, 2×) and the extracts added to the white lumps after removal of solvent. It was dried in a vacuum dessicator for 24 hours to obtain 2a which was quantitative. $^1$H NMR (in CDCl$_3$): δ in ppm 0.83-0.87 (3H, m), 1.23 (26H, m), 1.52-1.55 (2H, m), 2.67 (1H, D$_2$O exchangeable), 3.42-3.51 (4H, m), 3.60-3.70 (2H, m), 3.84-3.85 (1H, m), 6.63-6.70 (1H, D$_2$O exchangeable); $^{13}$C NMR (in CDCl$_3$): δ in ppm 14.6, 23.1, 26.5, 29.8, 29.9, 30.0, 30.1, 30.2, 32.4, 64.5, 71.0, 72.3, 72.9.

(±)-1-O-(tert-Butyldimethylsilyl)-3-O-hexadecylglycerol (3a)

Compound 2a (2.297 g, 7.26 mol) was dissolved in anhydrous pyridine (20 mL) at RT under argon. Imidazole (1.02 g, 14.52 mol) in anhydrous pyridine (10 mL) was then added followed by tert-butyl dimethylsilyl chloride (TB-DMS-Cl, 2.25 g, 14.52 mol) in anhydrous pyridine (20 mL). The reaction mixture was stirred at RT for 72 hours, poured into 0.5 M H$_2$SO$_4$ (150 mL) and extracted with diethyl ether (100 mL, 3×). The extract was washed successively with saturated aqueous NaHCO$_3$ (100 mL) and water (100 mL), dried over anhydrous Na$_2$SO$_4$ and the solvent removed under reduced pressure to obtain 3a, an oily material which was dried in a vacuum dessicator for 2 days (3.164 g, 100% yield). $^1$H NMR (in CDCl$_3$): δ in ppm 0.83-0.89 (15H, m), 1.22 (29H, m), 1.52-1.53 (2H, m), 2.60 (1H, s, D$_2$O exchangeable), 3.40-3.42 (4H, m), 3.59-3.61 (2H, m), 3.64 (1H, m); $^{13}$C NMR (in CDCl$_3$): δ in ppm 14.3, 18.2, 18.5, 22.9, 25.8, 26.0, 26.1, 26.3, 29.6, 29.8, 29.9, 32.1, 33.0, 64.2, 70.8, 71.6, 71.9.

(±)-1-O-(tert-Butyldimethylsilyl)-2-O-docosahexaenoyl-3-O-hexadecylglycerol (4a)

Anhydrous pyridine (0.15 mL) and toluene (10 mL) were added to 3a (249.0 mg, 0.578 mol) and stirred at RT under dry argon. Docosahexaenoyl chloride (200.0 mg, 0.578 mol) in toluene (5 mL) was then added dropwise to the reaction mixture over a period of 20 min and stirred at RT for 96 hours. The reaction mixture was poured into water (100 mL), extracted with diethyl ether (100 mL, 3×), washed successively with 0.25 M H$_2$SO$_4$ solution (100 mL), saturated aqueous NaHCO$_3$ (100 mL) and water (100 mL), and dried over anhydrous Na$_2$SO$_4$. After removal of solvent, the crude product was chromatographed on silica gel using hexane-dichloromethane to obtain product 4a (348.4 mg, 81.4% yield). $^1$H NMR (in CDCl$_3$): δ in ppm 0.89 (18H, m), 1.24 (29H, m), 1.53 (2H, m), 2.06 (2H, m), 2.40 (4H, m), 2.83 (10H, m), 3.40 (3H, m), 3.55 (2H, m), 3.71 (2H, m), 5.36 (12H, m); $^{13}$C NMR (in CDCl$_3$): δ in ppm 14.2, 14.4, 20.7, 22.2, 25.7 (2), 25.8, 26.0, 26.1, 26.3, 29.5, 29.7, 29.8, 29.9, 32.0, 35.3, 65.4, 71.7, 72.9 (2), 127.1, 127.9, 128.0, 128.1, 128.2, 128.4, 128.5, 128.7, 129.2, 129.3, 130.1, 132.1, 168.8.

cis-(±)-2-O-Docosahexaenoyl-1-O-hexadecylglycerol (5a)

To a mixture of 4a (348.4 mg, 0.4704 mol) and glacial acetic acid (120 μL) was added 1.0 M TBAF in 2 mL THF over a period of 15 min at 5-10° C. (ice-water bath) with constant stirring. The reaction mixture was stirred at RT for 48 hours. It was then poured into water (100 mL), extracted with diethyl ether (100 mL, 2×), washed successively with saturated aqueous NaHCO$_3$ (100 mL) and water (100 mL), and dried over anhydrous Na$_2$SO$_4$. After removal of solvent, the crude product was chromatographed on silica gel using dichloromethane-methanol to obtain 5a (140.8 mg, 48% yield). TLC: R$_F$=0.65 (CH$_2$Cl$_2$:MeOH, 95:5 v/v); $^1$H NMR (in CDCl$_3$): δ in ppm 0.85 (3H, t, J=7.5 Hz), 0.95 (3H, t, J=7.0 Hz), 1.23 (26H, m), 1.54 (2H, m), 2.05 (2H, m), 2.38 (4H, m), 2.80 (10H, m), 3.44-3.50 (5H, m), 3.62-3.68 (2H, m), 3.85 (1H, br s, D$_2$O exchangeable), 5.29-5.35 (12H, m); $^{13}$C NMR (in CDCl$_3$): δ in ppm 14.3, 18.3, 22.7, 22.9, 25.7, 25.8 (2), 26.3, 29.6, 29.7 (2), 29.8 (2), 29.9 (2), 32.1, 64.4, 70.7, 72.1, 72.7, 127.2, 127.8, 128.1, 128.2, 128.3 (2), 128.4, 128.5, 128.8, 129.7 (2), 132.2, 177.9; FT-IR (cm$^{-1}$) 3370 (br), 3013, 2954, 2918, 2850, 1712, 1470, 1397, 1382, 1326, 1239, 1123, 1060, 719; HRAPCI-MS m/z: measured 627.5349 ([M+H]$^+$, calcd. 627.5352 for C$_{41}$H$_{71}$O$_4$).

Example 12: Use of Metabolic Precursors for Restoration of PtdEt and EtnPl Pools In Vitro To investigate whether exogenous metabolic precursors can restore the ethanolamine phospholipids deficiency in vitro, a CHO cell line deficient in plasmalogen synthesis (NRel-4) was treated with the metabolic precursors 5a (sn-1-alkyl,sn-2-DHA glycerol) for 72 hours at a concentration of 20 μM, and its lipid profile was compared with the wild type cell line.

(A) Change in Total Ethanolamine Phospholipids

Figure 25A:
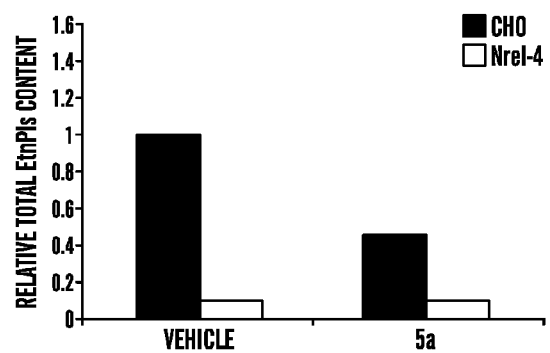
FIGS. 25A-B show the relative change in the total EtnPls and PtdEt content.
Figure 25B:
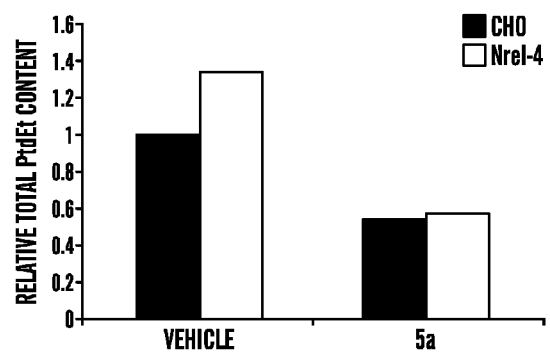

FIGS. 25A-B show the relative changes in total EtnPls and total PtdEt content when wild type CHO cells and plasmalogen-deficient NRel-4 cells are treated with metabolic precursor 5a (sn-1-alkyl,sn-2-DHA glycerol). The NRel-4 cell line treated with ethanol alone (vehicle to administer the compound) has significantly lower levels of total EtnPls (10.8%; P=0.0001) when compared with the CHO cell line treated with the vehicle alone (FIG. 25A). Treatment with 5a does not significantly alter the total EtnPls content in the CHO cell line (86.9%; P=0.083), but does elevate the relative total EtnPls content from 10.8% to 44.2%. FIG. 25B shows that the total PtdEt content in the NRel-4 cell line is not significantly greater than the control CHO cells (P=0.062). Treatment with 5a significantly reduced the total PtdEt content in the CHO cell line to 54.9% (P=0.0008) of untreated control, while that of the NRel-4 cell line was found to be at 55.9% (P=0.12) of the control.

(B) Change in Total DHA-Containing Phospholipids

Figure 26A:
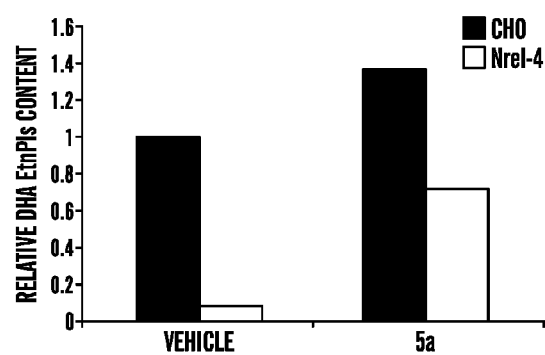
FIGS. 26A-B show the relative change in the DHA-EtnPls and DHA-PtdEt content.
Figure 26B:
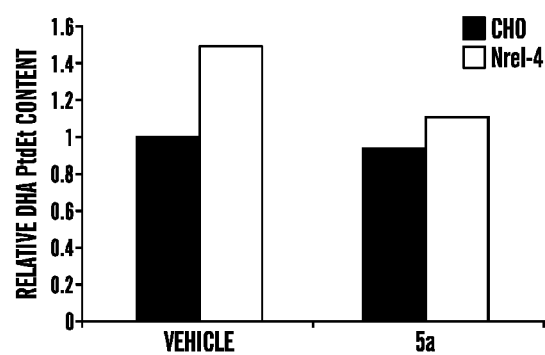

FIGS. 26A-B show the relative changes in total DHA-EtnPls and total DHA-PtdEt when wild type CHO cells and plasmalogen-deficient NRel-4 cells are treated with metabolic precursor 5a (sn-1-alkyl,sn-2-DHA glycerol). The NRel-4 cell line treated with ethanol alone has significantly lower levels of DHA-EtnPls (8.7%; P=0.000017) compared with the CHO cell line treated with the vehicle (FIG. 26A). Treatment with compound 5a significantly elevates the total DHA-EtnPls pool in CHO cells to 136.8% (P=0.004) of CHO levels, and simultaneously restores the NRel-4 deficient cell line to 72.3% of CHO levels (P=0.39).

FIG. 26B shows that treatment with compound 5a does not significantly alter the DHA-PtdEt pool in both cell lines tested (CHO: 93.5%, P=0.18; NRel-4: 110.6%, P=0.85) when compared with the untreated control CHO cell line.

Figure 27:
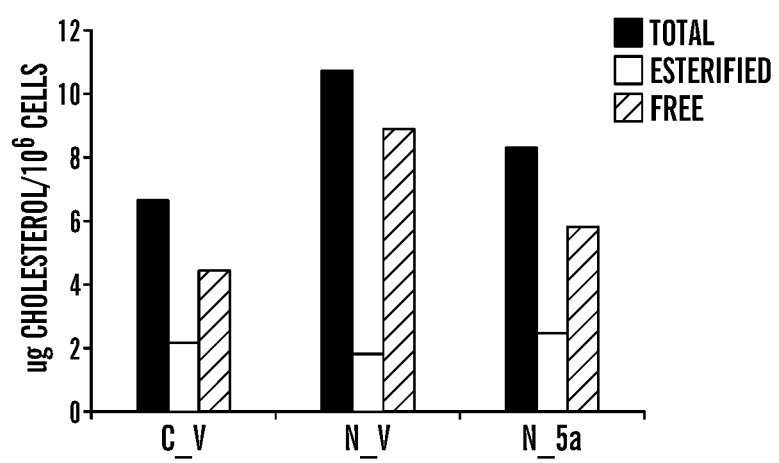
FIG. 27 shows the cholesterol content from total cell lysate. Total cholesterol (solid bars), esterified cholesterol (hatched bars), and free cholesterol (dotted) content is represented as µg per million cells. C_V: control CHO cells treated with ethanol carrier; N_V: NRel4 cells treated with ethanol carrier; N_5a: Nrel-4 cells treated with metabolic precursor 5a (20 µM).

Example 13: Effect of Metabolic Precursors on Total and Esterified Cholesterol Levels in Cultured Cells To test the effect of metabolite precursors on total and esterified cholesterol in vitro, the CHO/NRel-4 cell line model was used. Total cell lipid was extracted, and cholesterol was quantified using the Cholesterol Quantification kit (BioVision, Mountain View, Calif.) as suggested by the manufacturer. CHO cell line cultured in the presence of the ethanol vehicle (C_V) has 6.66 µg total cholesterol/million cells. This reflects the wild type phenotype, and was used for normalization. The NRel-4 cell line deficient in plasmalogen synthesis cultured in the presence of ethanol vehicle (N_V) had 10.75 µg total colesterol/million cells (61% higher than control). Culturing the deficient cells with the metabolic precursor 5a (sn-1-alkyl, sn-2-DHA glycerol) for 72 hours at a concentration of 20□M (N_5a) reduced the total cholesterol content to 8.28 µg/million cells (24% higher than control). A similar trend was seen with respect to the free cholesterol which increased from 4.5 µg/million cells (CHO) to 8.9 µg/million cells (NRel-4). Treatment with 5a reduced the free cholesterol content to 5.8 µg/million cells. A reciprocal trend was observed when assaying the fraction of cholesterol that was esterified in the cell lines. Plasmalogen deficient Nrel-4 cells when treated with the ethanol carrier (N_V) showed 16% lower basal level of esterified cholesterol (1.84 µg/million cells in NRel-4 compared to the control CHO cells which was at 2.19 µg/million cells). Treatment with compound 5a brought about a modest increase (34%) in the esterified fraction of cholesterol in the NRel-4 cell line (1.84 µg to 2.49 µg/million cells). These results, shown in FIG. 27, put together indicate a possible therapeutic effect of the metabolite precursors.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

1. Canadian study of health and aging: study methods and prevalence of dementia. *Cmaj* 150, 899-913 (1994).
2. Breitner, J. C. Dementia—epidemiological considerations, nomenclature, and a tacit consensus definition. *J Geriatr Psychiatry Neurol* 19, 129-36 (2006).
3. Khachaturian, A. S., Corcoran, C. D., Mayer, L. S., Zandi, P. P. & Breitner, J. C. Apolipoprotein E epsilon4 count affects age at onset of Alzheimer disease, but not lifetime susceptibility: The Cache County Study. *Arch Gen Psychiatry* 61, 518-24 (2004).
4. Cummings, J. L. & Benson, D. F. Dementia: A clinical approach. *Butterworth-Heineman, Stoneham, MA* (1992).
5. Polvikoski, T. et al. Prevalence of Alzheimer's disease in very elderly people: a prospective neuropathological study. *Neurology* 56, 1690-6 (2001).
6. Katzman, R. et al. Clinical, pathological, and neurochemical changes in dementia: a subgroup with preserved mental status and numerous neocortical plaques. *Ann Neurol.* 23, 138-144 (1988).
7. Galvin, J. E. et al. Predictors of preclinical Alzheimer disease and dementia: a clinicopathologic study. *Arch Neurol.* 62, 758-65 (2005).
8. Bennett, D. A. et al. Neuropathology of older persons without cognitive impairment from two community-based studies. *Neurology* 66, 1837-44 (2006).
9. Perry, E. K. et al. Correlation of cholinergic abnormalities with senile plaques and mental test scores in senile dementia. *Br Med J* 2, 1457-9 (1978).
10. Bowen, D. M., Benton, J. S., Spillane, J. A., Smith, C. C. & Allen, S. J. Choline acetyltransferase activity and histopathology of frontal neocortex from biopsies of demented patients. *J Neurol Sci* 57, 191-202 (1982).
11. Henke, H. & Lang, W. Cholinergic enzymes in neocortex, hippocampus and basal forebrain of non-neurological and senile dementia of Alzheimer-type patients. *Brain Res* 267, 281-91 (1983).
12. McGeer, P. L., McGeer, E. G., Suzuki, J., Dolman, C. E. & Nagai, T. Aging, Alzheimer's disease, and the cholinergic system of the basal forebrain. *Neurology* 34, 741-5 (1984).
13. Etienne, P. et al. Nucleus basalis neuronal loss, neuritic plaques and choline acetyltransferase activity in advanced Alzheimer's disease. *Neuroscience* 19, 1279-91 (1986).
14. Wilcock, G. K., Esiri, M. M., Bowen, D. M. & Smith, C. C. Alzheimer's disease. Correlation of cortical choline acetyltransferase activity with the severity of dementia and histological abnormalities. *J Neurol Sci* 57, 407-17 (1982).
15. DeKosky, S. T. et al. Cortical biopsy in Alzheimer's disease: diagnostic accuracy and neurochemical, neuropathological, and cognitive correlations. Intraventricular Bethanecol Study Group. *Ann Neurol* 32, 625-32 (1992).
16. Behl, P., Lanctot, K. L., Streiner, D. L., Guimont, I. & Black, S. E. Cholinesterase inhibitors slow decline in executive functions, rather than memory, in Alzheimer's disease: a 1-year observational study in the Sunnybrook dementia cohort. *Curr Alzheimer Res* 3, 147-56 (2006).
17. Whitehouse, P. J. et al. Alzheimer's disease and senile dementia: loss of neurons in the basal forebrain. *Science* 215, 1237-9 (1982).
18. Perry, R. H. et al. Extensive loss of choline acetyltransferase activity is not reflected by neuronal loss in the nucleus of Meynert in Alzheimer's disease. *Neurosci Lett* 33, 311-5 (1982).
19. Pearson, R. C. et al. Persistence of cholinergic neurons in the basal nucleus in a brain with senile dementia of the Alzheimer's type demonstrated by immunohistochemical staining for choline acetyltransferase. *Brain Res* 289, 375-9 (1983).
20. Vogels, O. J. et al. Cell loss and shrinkage in the nucleus basalis Meynert complex in Alzheimer's disease. *Neurobiol Aging* 11, 3-13 (1990).

21. Lehericy, S. et al. Heterogeneity and selectivity of the degeneration of cholinergic neurons in the basal forebrain of patients with Alzheimer's disease. *J Comp Neurol* 330, 15-31 (1993).
22. Gilmor, M. L. et al. Preservation of nucleus basalis neurons containing choline acetyltransferase and the vesicular acetylcholine transporter in the elderly with mild cognitive impairment and early Alzheimer's disease. *J Comp Neurol* 411, 693-704 (1999).
23. Mufson, E. J. et al. Loss of basal forebrain P75(NTR) immunoreactivity in subjects with mild cognitive impairment and Alzheimer's disease. *J Comp Neurol* 443, 136-53 (2002).
24. Kobayashi, K. et al. Apoptosis of astrocytes with enhanced lysosomal activity and oligodendrocytes in white matter lesions in Alzheimer's disease. *Neuropathol Appl Neurobiol* 28, 238-51 (2002).
25. Meguro, K. et al. Corpus callosum atrophy, white matter lesions, and frontal executive dysfunction in normal aging and Alzheimer's disease. A community-based study: the Tajiri Project. *Int Psychogeriatr* 15, 9-25 (2003).
26. de Leeuw, F. E., Korf, E., Barkhof, F. & Scheltens, P. White matter lesions are associated with progression of medial temporal lobe atrophy in Alzheimer disease. *Stroke* 37, 2248-52 (2006).
27. de Leeuw, F. E., Barkhof, F. & Scheltens, P. Progression of cerebral white matter lesions in Alzheimer's disease: a new window for therapy? *J Neurol Neurosurg Psychiatry* 76, 1286-8 (2005).
28. de la Monte, S. M. Quantitation of cerebral atrophy in preclinical and end-stage Alzheimer's disease. *Ann Neurol* 25, 450-9 (1989).
29. Burns, J. M. et al. White matter lesions are prevalent but differentially related with cognition in aging and early Alzheimer disease. *Arch Neurol* 62, 1870-6 (2005).
30. Medina, D. et al. White matter changes in mild cognitive impairment and AD: A diffusion tensor imaging study. *Neurobiol Aging* 27, 663-72 (2006).
31. Morris, J. C. et al. Mild cognitive impairment represents early-stage Alzheimer disease. *Arch Neurol* 58, 397-405 (2001).
32. Boyle, P. A., Wilson, R. S., Aggarwal, N. T., Tang, Y. & Bennett, D. A. Mild cognitive impairment: risk of Alzheimer disease and rate of cognitive decline. *Neurology* 67, 441-5 (2006).
33. Ginsberg, L., Rafique, S., Xuereb, J. H., Rapoport, S. I. & Gershfeld, N. L. Disease and anatomic specificity of ethanolamine plasmalogen deficiency in Alzheimer's disease brain. *Brain Res* 698, 223-6 (1995).
34. Han, X., Holtzman, D. M. & McKeel, D. W., Jr. Plasmalogen deficiency in early Alzheimer's disease subjects and in animal models: molecular characterization using electrospray ionization mass spectrometry. *J Neurochem* 77, 1168-80 (2001).
35. Han, X. Lipid alterations in the earliest clinically recognizable stage of Alzheimer's disease: implication of the role of lipids in the pathogenesis of Alzheimer's disease. *Curr Alzheimer Res* 2, 65-77 (2005).
36. Kitajka, K. et al. The role of n-3 polyunsaturated fatty acids in brain: modulation of rat brain gene expression by dietary n-3 fatty acids. *Proc Natl Acad Sci USA* 99, 2619-24 (2002).
37. Horrocks, L. A. & Sharma, M. in Phospholipids (eds. Hawthorne, J. N. & Ansell, G. B.) 51-93 (Elsevier, Amsterdam, 1982).
38. Farooqui, A. A. & Horrocks, L. A. Plasmalogens: workhorse lipids of membranes in normal and injured neurons and glia. *Neuroscientist* 7, 232-45 (2001).
39. Nagan, N. & Zoeller, R. A. Plasmalogens: biosynthesis and functions. *Prog Lipid Res* 40, 199-229 (2001).
40. Han, X. L. & Gross, R. W. Plasmenylcholine and phosphatidylcholine membrane bilayers possess distinct conformational motifs. *Biochemistry* 29, 4992-6 (1990).
41. Han, X. L. & Gross, R. W. Proton nuclear magnetic resonance studies on the molecular dynamics of plasmenylcholine/cholesterol and phosphatidylcholine/cholesterol bilayers. *Biochim Biophys Acta* 1063, 129-36 (1991).
42. Reiss, D., Beyer, K. & Engelmann, B. Delayed oxidative degradation of polyunsaturated diacyl phospholipids in the presence of plasmalogen phospholipids in vitro. *Biochem J* 323 (Pt 3), 807-14 (1997).
43. Tiraboschi, P. et al. The decline in synapses and cholinergic activity is asynchronous in Alzheimer's disease. *Neurology* 55, 1278-83 (2000).
44. Cutler, R. G. et al. Involvement of oxidative stress-induced abnormalities in ceramide and cholesterol metabolism in brain aging and Alzheimer's disease. *Proc Natl Acad Sci USA* 101, 2070-5 (2004).
45. Cheng, H., Xu, J., McKeel, D. W., Jr. & Han, X. Specificity and potential mechanism of sulfatide deficiency in Alzheimer's disease: an electrospray ionization mass spectrometric study. *Cell Mol Biol* (Noisy-le-grand) 49, 809-18 (2003).
46. Ginsberg, L., Xuereb, J. H. & Gershfeld, N. L. Membrane instability, plasmalogen content, and Alzheimer's disease. *J Neurochem* 70, 2533-8 (1998).
47. Davis, J. B. Oxidative mechanisms in beta-amyloid cytotoxicity. *Neurodegeneration* 5, 441-4 (1996).
48. Christen, Y. Oxidative stress and Alzheimer disease. *Am J Clin Nutr* 71, 621S-629S (2000).
49. Butterfield, D. A. & Lauderback, C. M. Lipid peroxidation and protein oxidation in Alzheimer's disease brain: potential causes and consequences involving amyloid beta-peptide-associated free radical oxidative stress. *Free Radic Biol Med* 32, 1050-60 (2002).
50. Urano, S. et al. Oxidative injury of synapse and alteration of antioxidative defense systems in rats, and its prevention by vitamin E. *Eur J Biochem* 245, 64-70 (1997).
51. Zoeller, R. A. et al. Increasing plasmalogen levels protects human endothelial cells during hypoxia. *Am J Physiol Heart Circ Physiol* 283, H671-9 (2002).
52. Glaser, P. E. & Gross, R. W. Rapid plasmenylethanolamine-selective fusion of membrane bilayers catalyzed by an isoform of glyceraldehyde-3-phosphate dehydrogenase: discrimination between glycolytic and fusogenic roles of individual isoforms. *Biochemistry* 34, 12193-203 (1995).
53. Sugihara, S., Ogawa, A., Nakazato, Y. & Yamaguchi, H. Cerebral beta amyloid deposition in patients with malignant neoplasms: its prevalence with aging and effects of radiation therapy on vascular amyloid. *Acta Neuropathol (Berl)* 90, 135-41 (1995).
54. Esiri, M. M., Biddolph, S. C. & Morris, C. S. Prevalence of Alzheimer plaques in AIDS. *J Neurol Neurosurg Psychiatry* 65, 29-33 (1998).
55. Pratico, D., Uryu, K., Leight, S., Trojanoswki, J. Q. & Lee, V. M. Increased lipid peroxidation precedes amyloid plaque formation in an animal model of Alzheimer amyloidosis. *J Neurosci* 21, 4183-7 (2001).

56. Holtzman, D. M. et al. Apolipoprotein E isoform-dependent amyloid deposition and neuritic degeneration in a mouse model of Alzheimer's disease. *Proc Natl Acad Sci USA* 97, 2892-7 (2000).
57. Puglielli, L., Tanzi, R. E. & Kovacs, D. M. Alzheimer's disease: the cholesterol connection. *Nat Neurosci* 6, 345-51 (2003).
58. Hegner, D. Age-dependence of molecular and functional changes in biological membrane properties. *Mech Ageing Dev* 14, 101-18 (1980).
59. Refolo, L. M. et al. Hypercholesterolemia accelerates the Alzheimer's amyloid pathology in a transgenic mouse model. *Neurobiol Dis* 7, 321-31 (2000).
60. Poirier, J. Apolipoprotein E and Alzheimer's disease. A role in amyloid catabolism. *Ann NY Acad Sci* 924, 81-90 (2000).
61. Harman, D. Role of free radicals in aging and disease. *Ann NY Acad Sci* 673, 126-41 (1992).
62. Masters, C. J. & Crane, D. I. On the role of the peroxisome in ontogeny, ageing and degenerative disease. *Mech Ageing Dev* 80, 69-83 (1995).
63. Yu, B. P. & Yang, R. Critical evaluation of the free radical theory of aging. A proposal for the oxidative stress hypothesis. *Ann NY Acad Sci* 786, 1-11 (1996).
64. Markesbery, W. R. & Carney, J. M. Oxidative alterations in Alzheimer's disease. *Brain Pathol* 9, 133-46 (1999).
65. Sun, G. Y. & Sun, A. Y. Effect of chronic ethanol administration on phospholipid acyl groups of synaptic plasma membrane fraction isolated from guinea pig brain. *Res Commun Chem Pathol Pharmacol* 24, 405-8 (1979).
66. Zs-Nagy, I. The role of membrane structure and function in cellular aging: a review. *Mech Ageing Dev* 9, 237-46 (1979).
67. Roth, G. S., Joseph, J. A. & Mason, R. P. Membrane alterations as causes of impaired signal transduction in Alzheimer's disease and aging. *Trends Neurosci* 18, 203-6 (1995).
68. Perichon, R., Bourre, J. M., Kelly, J. F. & Roth, G. S. The role of peroxisomes in aging. *Cell Mol Life Sci* 54, 641-52 (1998).
69. Janssen, A. et al. Neuronal migration depends on intact peroxisomal function in brain and in extraneuronal tissues. *J Neurosci* 23, 9732-41 (2003).
70. Bourre, J. M. & Piciotti, M. Delta-6 desaturation of alpha-linolenic acid in brain and liver during development and aging in the mouse. *Neurosci Lett* 141, 65-8 (1992).
71. Santos, M. J. et al. Peroxisomal proliferation protects from beta-amyloid neurodegeneration. *J Biol Chem* 280, 41057-68 (2005).
72. Watson, G. S. et al. Preserved cognition in patients with early Alzheimer disease and amnestic mild cognitive impairment during treatment with rosiglitazone: a preliminary study. *Am J Geriatr Psychiatry* 13, 950-8 (2005).
73. Haining, J. L. & Legan, J. S. Catalase turnover in rat liver and kidney as a function of age. *Exp Gerontol* 8, 85-91 (1973).
74. Rao, G., Xia, E. & Richardson, A. Effect of age on the expression of antioxidant enzymes in male Fischer F344 rats. *Mech Ageing Dev* 53, 49-60 (1990).
75. Perichon, R. & Bourre, J. M. Peroxisomal beta-oxidation activity and catalase activity during development and aging in mouse liver. *Biochimie* 77, 288-93 (1995).
76. Voss, A., Reinhart, M., Sankarappa, S. & Sprecher, H. The metabolism of 7,10,13,16,19-docosapentaenoic acid to 4,7,10,13,16,19-docosahexaenoic acid in rat liver is independent of a 4-desaturase. *J Biol Chem* 266, 19995-20000 (1991).
77. Andre, A., Juaneda, P., Sebedio, J. L. & Chardigny, J. M. Plasmalogen metabolism-related enzymes in rat brain during aging: influence of n-3 fatty acid intake. *Biochimie* 88, 103-11 (2006).
78. Favreliere, S. et al. Age-related changes in ethanolamine glycerophospholipid fatty acid levels in rat frontal cortex and hippocampus. *Neurobiol Aging* 21, 653-60 (2000).
79. Legakis, J. E. et al. Peroxisome senescence in human fibroblasts. *Mol Biol Cell* 13, 4243-55 (2002).
80. Zoeller, R. A. & Raetz, C. R. Isolation of animal cell mutants deficient in plasmalogen biosynthesis and peroxisome assembly. *Proc Natl Acad Sci USA* 83, 5170-4 (1986).
81. Martinez, M. Severe deficiency of docosahexaenoic acid in peroxisomal disorders: a defect of delta 4 desaturation? *Neurology* 40, 1292-8 (1990).
82. Scott, B. L. & Bazan, N. G. Membrane docosahexaenoate is supplied to the developing brain and retina by the liver. *Proc Natl Acad Sci USA* 86, 2903-7 (1989).
83. Gaposchkin, D. P. & Zoeller, R. A. Plasmalogen status influences docosahexaenoic acid levels in a macrophage cell line. Insights using ether lipid-deficient variants. *J Lipid Res* 40, 495-503 (1999).
84. Fratiglioni, L. et al. Very old women at highest risk of dementia and Alzheimer's disease: incidence data from the Kungsholmen Project, Stockholm. *Neurology* 48, 132-8 (1997).
85. Wells, K., Farooqui, A. A., Liss, L. & Horrocks, L. A. Neural membrane phospholipids in Alzheimer disease. *Neurochem Res* 20, 1329-33 (1995).
86. Weisser, M. et al. Dramatic increase of alpha-hydroxyaldehydes derived from plasmalogens in the aged human brain. *Chem Phys Lipids* 90, 135-42 (1997).
87. Brosche, T., Summa, J. D. & Platt, D. Erythrocyte membrane changes associated with nutrition and aging—the role of plasmalogens. *Arch Gerontol Geriatr* 9, 291-6 (1989).

TABLE 1

Clinical Data on Subject Cohorts

| Population | n | Age | | MMSE | | ADAS-cog | |
|---|---|---|---|---|---|---|---|
| | | Mean | SEM | Mean | SEM | Mean | SEM |
| Age Ctl, 30-39, Female | 14 | 36.4 | 0.9 | | | 5 | |
| Age Ctl, 30-39, Male | 11 | 35.2 | 1.0 | | | | |
| Age Ctl, 40-49, Female | 44 | 44.8 | 0.5 | | | | |
| Age Ctl, 40-49, Male | 27 | 44.7 | 0.6 | | | | |
| Age Ctl, 50-59, Female | 107 | 54.2 | 0.3 | | | | |
| Age Ctl, 50-59, Male | 59 | 54.1 | 0.4 | | | | |
| Age Ctl, 60-69, Female | 55 | 63.4 | 0.3 | | | | |
| Age Ctl, 60-69, Male | 34 | 64.4 | 0.5 | | | | |

TABLE 1-continued

Clinical Data on Subject Cohorts

| Population | n | Age Mean | Age SEM | MMSE Mean | MMSE SEM | ADAS-cog Mean | ADAS-cog SEM |
|---|---|---|---|---|---|---|---|
| Age Ctl, 70+_Female | 27 | 79.7 | 1.2 | | | | |
| Age Ctl, 70+_Male | 35 | 75.5 | 0.7 | | | | |
| Cognitive Normal, Female | 36 | 77.6 | 1.1 | 29.6 | 0.1 | | |
| Cognitive Normal, Male | 32 | 76.8 | 1.1 | 29.3 | 0.1 | | |
| SDAT_all, Female | 140 | 80.0 | 0.6 | 12.6 | 0.7 | 34.2 | 1.6 |
| SDAT_all, Male | 117 | 79.8 | 0.7 | 15.3 | 0.5 | 27.4 | 1.3 |
| SDAT, ADAS 5-19, Female | 38 | 79.6 | 1.2 | 17.6 | 0.7 | 15.2 | 0.6 |
| SDAT, ADAS 20-39, Female | 54 | 78.6 | 1.0 | 16.6 | 0.7 | 27.0 | 0.8 |
| SDAT, ADAS 40-70, Female | 48 | 81.9 | 1.1 | 4.2 | 0.7 | 57.3 | 1.5 |
| SDAT, ADAS 5-19, Male | 40 | 79.0 | 1.1 | 17.3 | 0.7 | 15.3 | 0.5 |
| SDAT, ADAS 20-39, Male | 58 | 79.6 | 0.9 | 16.8 | 0.6 | 27.5 | 0.7 |
| SDAT, ADAS 40-70, Male | 18 | 82.6 | 2.1 | 6.2 | 1.1 | 53.2 | 2.2 |
| Post Mortem SDAT Male | 10 | 80.1 | 1.4 | | | | |
| Post Mortem SDAT Female | 10 | 77.6 | 1.5 | | | | |
| Post Mortem Ctl, Female | 9 | 84.4 | 1.8 | | | | |
| Post Mortem Ctl, Male | 10 | 77.9 | 1.4 | | | | |

TABLE 2

List of Preferred List of Metabolites

| Metabolite Code | Metabolite Name | Molecular Formula | Parent Mass | M − H Mass | Diagnostic Fragment Mass | MS/MS Transition |
|---|---|---|---|---|---|---|
| M01 | PtdEt 16:0/18:0 | C39H78N1O8P1 | 719.54648 | 718.5 | R1 (C16H31O2) − 255 | 718.0/255.0 |
| M02 | PtdEt 16:0/18:1 | C39H76N1O8P1 | 717.53083 | 716.5 | R1 (C16H31O2) − 255 | 716.0/255.0 |
| M03 | PtdEt 18:0/18:0 | C41H82N1O8P1 | 747.57777 | 746.5 | R1 (C18H35O2) − 283 | 746.0/283.0 |
| M04 | PtdEt 18:0/18:1 | C41H80N1O8P1 | 745.56213 | 744.5 | R1 (C18H35O2) − 283 | 744.0/283.0 |
| M05 | Plasmanyl 16:0/18:1 | C39H78N1O7P1 | 703.55156 | 702.5 | R2 (C18H31O2) − 281 | 702.0/281.0 |
| M06 | Plasmanyl 16:0/18:2 | C39H76N1O7P1 | 701.53591 | 700.5 | R2 (C18H31O2) − 279 | 700.0/279.0 |
| M07 | Plasmanyl 16:0/20:4 | C41H76N1O7P1 | 725.53591 | 724.5 | R2 (C20H31O2) − 303 | 724.0/303.0 |
| M08 | Plasmanyl 16:0/22:4 | C43H80N1O7P1 | 753.56721 | 752.5 | R2 (C22H35O2) − 331 | 752.0/331.0 |
| M09 | Plasmanyl 16:0/22:6 | C43H76N1O7P1 | 749.53591 | 748.5 | R2 (C22H31O2) − 327 | 748.0/327.0 |
| M10 | Plasmanyl 18:0/18:1 | C41H82N1O7P1 | 731.58286 | 730.5 | R2 (C18H33O2) − 281 | 730.0/281.0 |
| M11 | Plasmanyl 18:0/18:2 | C41H80N1O7P1 | 729.56721 | 728.5 | R2 (C18H31O2) − 279 | 728.0/279.0 |
| M12 | Plasmanyl 18:0/20:4 | C43H80N1O7P1 | 753.56721 | 752.5 | R2 (C20H31O2) − 303 | 752.0/303.0 |
| M13 | Plasmanyl 18:0/22:4 | C45H84N1O7P1 | 781.59851 | 780.5 | R2 (C22H35O2) − 331 | 780.0/331.0 |
| M14 | Plasmanyl 18:0/22:6 | C45H80N1O7P1 | 777.56721 | 776.5 | R2 (C22H31O2) − 327 | 776.0/327.0 |
| M15 | Plasmenyl 16:0/18:1 | C39H76N1O7P1 | 701.53591 | 700.5 | R2 (C18H33O2) − 281 | 700.0/281.0 |
| M16 | Plasmenyl 16:0/18:2 | C39H74N1O7P1 | 699.52026 | 698.5 | R2 (C18H31O2) − 279 | 698.0/279.0 |
| M17 | Plasmenyl 16:0/20:4 | C41H74N1O7P1 | 723.52026 | 722.5 | R2 (C20H31O2) − 303 | 722.0/303.0 |
| M18 | Plasmenyl 16:0/22:4 | C43H78N1O7P1 | 751.55156 | 750.5 | R2 (C22H35O2) − 331 | 750.0/331.0 |
| M19 | Plasmenyl 16:0/22:6 | C43H74N1O7P1 | 747.52026 | 746.5 | R2 (C22H31O2) − 327 | 746.0/327.0 |
| M20 | Plasmenyl 18:0/18:1 | C41H80N1O7P1 | 729.56721 | 728.5 | R2 (C18H33O2) − 281 | 728.0/281.0 |
| M21 | Plasmenyl 18:0/18:2 | C41H78N1O7P1 | 727.55156 | 726.5 | R2 (C18H31O2) − 279 | 726.0/279.0 |
| M22 | Plasmenyl 18:0/20:4 | C43H78N1O7P1 | 751.55156 | 750.5 | R2 (C20H31O2) − 303 | 750.6/303.2 |
| M23 | Plasmenyl 18:0/22:4 | C45H82N1O7P1 | 779.58286 | 778.5 | R2 (C22H35O2) − 331 | 778.0/331.0 |
| M24 | Plasmenyl 18:0/22:6 | C45H78N1O7P1 | 775.55156 | 774.5 | R2 (C22H31O2) − 327 | 774.0/327.0 |
| M25 | Free 22:6 | C22H32O2 | 328.24022 | 327.2 | (C21H31) − 283 | 327.2/283.0 |
| M26 | Free 20:4 | C20H32O2 | 304.24022 | 303.2 | (C19H31) − 259 | 303.2/259.5 |

TABLE 3

Average Serum Ethanolamine Phospholipid Levels in Males of Different Levels of Dementia Severity

| Metabolite Code | Cognitive Normal, Male Mean | Cognitive Normal, Male SEM | SDAT_all, Male Mean | SDAT_all, Male SEM | SDAT, ADAS 5-19, Male Mean | SDAT, ADAS 5-19, Male SEM | SDAT, ADAS 20-39, Male Mean | SDAT, ADAS 20-39, Male SEM | SDAT, ADAS 40-70, Male Mean | SDAT, ADAS 40-70, Male SEM |
|---|---|---|---|---|---|---|---|---|---|---|
| M01 | 0.116 | 0.006 | 0.119 | 0.004 | 0.117 | 0.006 | 0.117 | 0.006 | 0.117 | 0.011 |
| M02 | 0.066 | 0.006 | 0.056 | 0.004 | 0.060 | 0.009 | 0.054 | 0.004 | 0.046 | 0.006 |
| M03 | 0.109 | 0.007 | 0.084 | 0.004 | 0.091 | 0.006 | 0.080 | 0.005 | 0.072 | 0.007 |
| M04 | 0.030 | 0.002 | 0.026 | 0.002 | 0.025 | 0.004 | 0.027 | 0.002 | 0.022 | 0.003 |
| M05 | 0.012 | 0.001 | 0.010 | 0.000 | 0.011 | 0.001 | 0.010 | 0.001 | 0.010 | 0.001 |
| M06 | 0.028 | 0.002 | 0.025 | 0.001 | 0.024 | 0.002 | 0.025 | 0.002 | 0.024 | 0.002 |
| M07 | 0.062 | 0.005 | 0.044 | 0.002 | 0.047 | 0.004 | 0.044 | 0.003 | 0.036 | 0.004 |

TABLE 3-continued

Average Serum Ethanolamine Phospholipid Levels in Males of Different Levels of Dementia Severity

| Metabolite Code | Cognitive Normal, Male | | SDAT_all, Male | | SDAT, ADAS 5-19, Male | | SDAT, ADAS 20-39, Male | | SDAT, ADAS 40-70, Male | |
|---|---|---|---|---|---|---|---|---|---|---|
| | Mean | SEM | Mean | SEM | Mean | SEM | Mean | SEM | Mean | SEM |
| M08 | 0.007 | 0.001 | 0.005 | 0.000 | 0.006 | 0.001 | 0.005 | 0.000 | 0.004 | 0.001 |
| M09 | 0.022 | 0.002 | 0.015 | 0.001 | 0.016 | 0.002 | 0.015 | 0.001 | 0.011 | 0.001 |
| M10 | 0.054 | 0.002 | 0.052 | 0.002 | 0.053 | 0.003 | 0.051 | 0.002 | 0.047 | 0.005 |
| M11 | 0.110 | 0.005 | 0.095 | 0.004 | 0.095 | 0.007 | 0.095 | 0.006 | 0.088 | 0.009 |
| M12 | 0.205 | 0.011 | 0.162 | 0.006 | 0.170 | 0.011 | 0.160 | 0.008 | 0.141 | 0.013 |
| M13 | 0.013 | 0.001 | 0.011 | 0.000 | 0.011 | 0.001 | 0.010 | 0.001 | 0.010 | 0.001 |
| M14 | 0.051 | 0.004 | 0.036 | 0.002 | 0.041 | 0.004 | 0.034 | 0.002 | 0.028 | 0.003 |
| M15 | 0.076 | 0.004 | 0.064 | 0.002 | 0.067 | 0.005 | 0.062 | 0.003 | 0.060 | 0.006 |
| M16 | 0.266 | 0.015 | 0.207 | 0.009 | 0.213 | 0.015 | 0.202 | 0.012 | 0.191 | 0.018 |
| M17 | 0.470 | 0.038 | 0.302 | 0.015 | 0.338 | 0.031 | 0.292 | 0.020 | 0.242 | 0.026 |
| M18 | 0.026 | 0.003 | 0.019 | 0.001 | 0.020 | 0.002 | 0.018 | 0.001 | 0.016 | 0.002 |
| M19 | 0.127 | 0.013 | 0.078 | 0.004 | 0.088 | 0.009 | 0.076 | 0.006 | 0.056 | 0.006 |
| M20 | 0.078 | 0.005 | 0.064 | 0.003 | 0.069 | 0.005 | 0.061 | 0.003 | 0.059 | 0.007 |
| M21 | 0.265 | 0.017 | 0.217 | 0.010 | 0.226 | 0.019 | 0.211 | 0.014 | 0.201 | 0.023 |
| M22 | 1.040 | 0.087 | 0.736 | 0.037 | 0.789 | 0.071 | 0.723 | 0.052 | 0.624 | 0.067 |
| M23 | 0.018 | 0.001 | 0.015 | 0.001 | 0.016 | 0.001 | 0.014 | 0.001 | 0.013 | 0.001 |
| M24 | 0.116 | 0.012 | 0.079 | 0.005 | 0.090 | 0.010 | 0.075 | 0.006 | 0.061 | 0.008 |
| M25 | 0.240 | 0.017 | 0.218 | 0.009 | 0.249 | 0.018 | 0.208 | 0.010 | 0.183 | 0.017 |
| M26 | 0.072 | 0.003 | 0.070 | 0.002 | 0.074 | 0.004 | 0.070 | 0.003 | 0.065 | 0.006 |

TABLE 4a

Ratio and T-test Values Between Males of Various Levels of Dementia

| Metabolite Code | AD, All to CN, Male | | ADAS 5-19 to CN, Male | | ADAS 20-39 to CN, Male | | ADAS 40-70 to CN, Male | |
|---|---|---|---|---|---|---|---|---|
| | Ratio | ttest | Ratio | ttest | Ratio | ttest | Ratio | ttest |
| M01 | 1.028 | 7.1E−01 | 1.011 | 8.9E−01 | 1.016 | 8.3E−01 | 1.014 | 8.9E−01 |
| M02 | 0.845 | 2.1E−01 | 0.898 | 5.5E−01 | 0.816 | 7.5E−02 | 0.690 | 2.4E−02 |
| M03 | 0.769 | 1.6E−03 | 0.836 | 6.9E−02 | 0.735 | 6.4E−04 | 0.655 | 1.4E−03 |
| M04 | 0.882 | 3.9E−01 | 0.836 | 2.9E−01 | 0.896 | 4.1E−01 | 0.726 | 2.7E−01 |
| M05 | 0.882 | 1.3E−01 | 0.896 | 2.7E−01 | 0.865 | 9.1E−02 | 0.836 | 1.5E−01 |
| M06 | 0.877 | 1.3E−01 | 0.855 | 9.1E−02 | 0.876 | 1.6E−01 | 0.856 | 1.4E−01 |
| M07 | 0.709 | 3.9E−04 | 0.753 | 1.8E−02 | 0.704 | 1.6E−03 | 0.589 | 1.1E−03 |
| M08 | 0.759 | 1.9E−02 | 0.806 | 1.8E−01 | 0.755 | 2.1E−02 | 0.629 | 1.5E−02 |
| M09 | 0.658 | 2.7E−04 | 0.731 | 2.7E−02 | 0.654 | 1.4E−03 | 0.472 | 2.2E−04 |
| M10 | 0.960 | 6.0E−01 | 0.978 | 7.9E−01 | 0.942 | 4.0E−01 | 0.877 | 1.7E−01 |
| M11 | 0.866 | 9.3E−02 | 0.861 | 1.1E−01 | 0.861 | 8.1E−02 | 0.798 | 2.6E−02 |
| M12 | 0.793 | 1.8E−03 | 0.831 | 3.9E−02 | 0.783 | 2.2E−03 | 0.686 | 8.3E−04 |
| M13 | 0.850 | 2.7E−02 | 0.890 | 1.8E−01 | 0.827 | 1.3E−02 | 0.786 | 1.8E−02 |
| M14 | 0.704 | 3.7E−04 | 0.800 | 6.9E−02 | 0.666 | 1.1E−04 | 0.553 | 2.3E−04 |
| M15 | 0.842 | 2.2E−02 | 0.883 | 1.8E−01 | 0.810 | 3.0E−03 | 0.784 | 1.9E−02 |
| M16 | 0.778 | 1.6E−03 | 0.802 | 1.7E−02 | 0.759 | 1.2E−03 | 0.718 | 3.2E−03 |
| M17 | 0.644 | 4.5E−06 | 0.718 | 7.5E−03 | 0.621 | 1.3E−05 | 0.515 | 1.0E−04 |
| M18 | 0.708 | 1.6E−03 | 0.758 | 6.0E−02 | 0.689 | 2.0E−03 | 0.613 | 7.7E−03 |
| M19 | 0.611 | 1.0E−05 | 0.688 | 1.1E−02 | 0.596 | 6.1E−05 | 0.442 | 2.0E−04 |
| M20 | 0.826 | 2.3E−02 | 0.892 | 2.7E−01 | 0.786 | 6.1E−03 | 0.762 | 3.9E−02 |
| M21 | 0.818 | 2.7E−02 | 0.852 | 1.3E−01 | 0.796 | 2.0E−02 | 0.757 | 2.9E−02 |
| M22 | 0.708 | 4.4E−04 | 0.758 | 2.7E−02 | 0.695 | 1.3E−03 | 0.600 | 1.9E−03 |
| M23 | 0.801 | 1.1E−02 | 0.857 | 1.6E−01 | 0.776 | 4.0E−03 | 0.723 | 8.6E−03 |
| M24 | 0.680 | 1.1E−03 | 0.777 | 9.8E−02 | 0.647 | 1.3E−03 | 0.524 | 2.8E−03 |
| M25 | 0.909 | 2.4E−01 | 1.035 | 7.4E−01 | 0.865 | 8.0E−02 | 0.760 | 3.0E−02 |
| M26 | 0.978 | 7.4E−01 | 1.023 | 7.5E−01 | 0.968 | 6.5E−01 | 0.907 | 2.9E−01 |

TABLE 4b

Ratio and T-test Values Between Males of Various Levels of Dementia

| Metabolite Code | ADAS 20-39 to 5-19, Male | | ADAS 40-70 to 5-19, Male | | ADAS 40-70 to 20-39, Male | |
|---|---|---|---|---|---|---|
| | Ratio | ttest | Ratio | ttest | Ratio | ttest |
| M01 | 1.005 | 9.4E−01 | 1.003 | 9.8E−01 | 0.998 | 9.8E−01 |
| M02 | 0.908 | 5.3E−01 | 0.768 | 3.2E−01 | 0.846 | 2.8E−01 |

TABLE 4b-continued

Ratio and T-test Values Between Males of Various Levels of Dementia

| | ADAS 20-39 to 5-19, Male | | ADAS 40-70 to 5-19, Male | | ADAS 40-70 to 20-39, Male | |
|---|---|---|---|---|---|---|
| Metabolite Code | Ratio | ttest | Ratio | ttest | Ratio | ttest |
| M03 | 0.880 | 1.5E−01 | 0.784 | 7.0E−02 | 0.891 | 3.4E−01 |
| M04 | 1.072 | 6.8E−01 | 0.868 | 5.8E−01 | 0.810 | 2.8E−01 |
| M05 | 0.966 | 7.0E−01 | 0.933 | 6.1E−01 | 0.966 | 7.7E−01 |
| M06 | 1.024 | 8.1E−01 | 1.001 | 9.9E−01 | 0.978 | 8.6E−01 |
| M07 | 0.935 | 5.5E−01 | 0.783 | 1.3E−01 | 0.837 | 2.5E−01 |
| M08 | 0.936 | 6.3E−01 | 0.780 | 2.7E−01 | 0.833 | 2.4E−01 |
| M09 | 0.895 | 4.2E−01 | 0.646 | 3.3E−02 | 0.721 | 1.0E−01 |
| M10 | 0.963 | 6.3E−01 | 0.897 | 3.7E−01 | 0.932 | 5.0E−01 |
| M11 | 1.000 | 1.0E+00 | 0.927 | 5.7E−01 | 0.927 | 5.4E−01 |
| M12 | 0.942 | 4.8E−01 | 0.826 | 1.3E−01 | 0.877 | 2.4E−01 |
| M13 | 0.930 | 3.8E−01 | 0.883 | 3.2E−01 | 0.950 | 6.3E−01 |
| M14 | 0.832 | 1.1E−01 | 0.691 | 4.5E−02 | 0.830 | 2.0E−01 |
| M15 | 0.917 | 3.0E−01 | 0.888 | 3.7E−01 | 0.968 | 7.4E−01 |
| M16 | 0.947 | 5.4E−01 | 0.895 | 3.9E−01 | 0.946 | 6.4E−01 |
| M17 | 0.865 | 1.9E−01 | 0.716 | 5.6E−02 | 0.828 | 1.9E−01 |
| M18 | 0.909 | 4.5E−01 | 0.809 | 2.8E−01 | 0.890 | 4.4E−01 |
| M19 | 0.866 | 2.5E−01 | 0.642 | 3.1E−02 | 0.741 | 7.4E−02 |
| M20 | 0.880 | 1.6E−01 | 0.854 | 2.7E−01 | 0.970 | 8.0E−01 |
| M21 | 0.934 | 5.2E−01 | 0.889 | 4.4E−01 | 0.952 | 7.2E−01 |
| M22 | 0.917 | 4.5E−01 | 0.791 | 1.6E−01 | 0.863 | 3.3E−01 |
| M23 | 0.906 | 3.3E−01 | 0.844 | 2.8E−01 | 0.931 | 5.6E−01 |
| M24 | 0.833 | 1.7E−01 | 0.674 | 5.9E−02 | 0.810 | 2.3E−01 |
| M25 | 0.836 | 3.7E−02 | 0.735 | 2.8E−02 | 0.879 | 2.1E−01 |
| M26 | 0.946 | 4.3E−01 | 0.887 | 2.3E−01 | 0.937 | 5.2E−01 |

TABLE 4

Effect of Pathology State on Serum Ethanolamine Phospholipid Levels in Males

| | Post Mortem Ctl, Male | | Post Mortem SDAT Male | | SDAT vs Control | |
|---|---|---|---|---|---|---|
| Metabolite Code | Mean | SEM | Mean | SEM | Ratio | ttest |
| M01 | 0.127 | 0.017 | 0.089 | 0.013 | 0.702 | 0.091 |
| M02 | 0.046 | 0.006 | 0.026 | 0.005 | 0.568 | 0.022 |
| M03 | 0.059 | 0.006 | 0.036 | 0.006 | 0.610 | 0.014 |
| M04 | 0.017 | 0.004 | 0.007 | 0.002 | 0.420 | 0.024 |
| M05 | 0.006 | 0.001 | 0.004 | 0.000 | 0.479 | 0.019 |
| M06 | 0.009 | 0.001 | 0.006 | 0.001 | 0.475 | 0.005 |
| M07 | 0.012 | 0.003 | 0.009 | 0.001 | 0.451 | 0.033 |
| M08 | 0.003 | 0.001 | 0.002 | 0.000 | 0.410 | 0.015 |
| M09 | 0.006 | 0.002 | 0.003 | 0.001 | 0.269 | 0.048 |
| M10 | 0.041 | 0.005 | 0.036 | 0.006 | 0.608 | 0.019 |
| M11 | 0.052 | 0.006 | 0.041 | 0.006 | 0.474 | 0.001 |
| M12 | 0.094 | 0.013 | 0.084 | 0.012 | 0.587 | 0.024 |
| M13 | 0.009 | 0.001 | 0.008 | 0.001 | 0.576 | 0.008 |
| M14 | 0.025 | 0.005 | 0.021 | 0.007 | 0.429 | 0.009 |
| M15 | 0.045 | 0.005 | 0.029 | 0.004 | 0.648 | 0.026 |
| M16 | 0.092 | 0.012 | 0.053 | 0.007 | 0.570 | 0.012 |
| M17 | 0.097 | 0.021 | 0.047 | 0.007 | 0.489 | 0.036 |
| M18 | 0.010 | 0.001 | 0.005 | 0.001 | 0.521 | 0.004 |
| M19 | 0.032 | 0.006 | 0.014 | 0.002 | 0.452 | 0.011 |
| M20 | 0.031 | 0.004 | 0.017 | 0.002 | 0.542 | 0.006 |
| M21 | 0.072 | 0.011 | 0.033 | 0.006 | 0.464 | 0.006 |
| M22 | 0.217 | 0.040 | 0.106 | 0.017 | 0.486 | 0.020 |
| M23 | 0.009 | 0.001 | 0.005 | 0.001 | 0.565 | 0.005 |
| M24 | 0.029 | 0.004 | 0.013 | 0.003 | 0.448 | 0.007 |
| M25 | 0.238 | 0.023 | 0.180 | 0.026 | 0.757 | 0.114 |
| M26 | 0.073 | 0.008 | 0.050 | 0.006 | 0.684 | 0.034 |

TABLE 5

Effect of Dementia State on Serum Ethanolamine Phospholipid Levels in Females

| Metabolite Code | Cognitive Normal, Female | | SDAT_all, Female | | SDAT, ADAS 5-19, Female | | SDAT, ADAS 20-39, Female | | SDAT, ADAS 40-70, Female | |
|---|---|---|---|---|---|---|---|---|---|---|
| | Mean | SEM | Mean | SEM | Mean | SEM | Mean | SEM | Mean | SEM |
| M01 | 0.118 | 0.005 | 0.113 | 0.003 | 0.109 | 0.004 | 0.112 | 0.005 | 0.118 | 0.006 |
| M02 | 0.062 | 0.005 | 0.053 | 0.002 | 0.050 | 0.003 | 0.057 | 0.004 | 0.052 | 0.004 |
| M03 | 0.099 | 0.005 | 0.076 | 0.002 | 0.080 | 0.004 | 0.076 | 0.004 | 0.073 | 0.004 |
| M04 | 0.026 | 0.002 | 0.025 | 0.001 | 0.024 | 0.002 | 0.027 | 0.002 | 0.024 | 0.003 |
| M05 | 0.011 | 0.001 | 0.009 | 0.000 | 0.010 | 0.001 | 0.009 | 0.001 | 0.009 | 0.001 |
| M06 | 0.027 | 0.001 | 0.022 | 0.001 | 0.024 | 0.001 | 0.023 | 0.001 | 0.020 | 0.001 |
| M07 | 0.056 | 0.005 | 0.041 | 0.002 | 0.044 | 0.004 | 0.042 | 0.004 | 0.036 | 0.003 |
| M08 | 0.006 | 0.001 | 0.005 | 0.000 | 0.005 | 0.000 | 0.006 | 0.001 | 0.005 | 0.000 |
| M09 | 0.019 | 0.002 | 0.013 | 0.001 | 0.015 | 0.001 | 0.014 | 0.001 | 0.012 | 0.001 |
| M10 | 0.054 | 0.003 | 0.048 | 0.001 | 0.049 | 0.002 | 0.047 | 0.002 | 0.048 | 0.003 |
| M11 | 0.105 | 0.004 | 0.088 | 0.003 | 0.094 | 0.004 | 0.090 | 0.005 | 0.080 | 0.004 |
| M12 | 0.196 | 0.012 | 0.153 | 0.005 | 0.166 | 0.009 | 0.152 | 0.010 | 0.142 | 0.010 |
| M13 | 0.013 | 0.001 | 0.010 | 0.000 | 0.011 | 0.000 | 0.010 | 0.001 | 0.010 | 0.001 |
| M14 | 0.046 | 0.003 | 0.035 | 0.002 | 0.040 | 0.003 | 0.034 | 0.002 | 0.033 | 0.003 |
| M15 | 0.073 | 0.004 | 0.059 | 0.002 | 0.061 | 0.003 | 0.061 | 0.003 | 0.056 | 0.003 |
| M16 | 0.250 | 0.013 | 0.192 | 0.007 | 0.214 | 0.013 | 0.201 | 0.012 | 0.164 | 0.008 |
| M17 | 0.408 | 0.033 | 0.288 | 0.015 | 0.317 | 0.026 | 0.304 | 0.026 | 0.247 | 0.021 |
| M18 | 0.024 | 0.002 | 0.018 | 0.001 | 0.019 | 0.001 | 0.019 | 0.002 | 0.016 | 0.001 |
| M19 | 0.103 | 0.008 | 0.071 | 0.004 | 0.079 | 0.007 | 0.072 | 0.006 | 0.063 | 0.006 |
| M20 | 0.077 | 0.004 | 0.059 | 0.002 | 0.064 | 0.004 | 0.060 | 0.004 | 0.054 | 0.003 |
| M21 | 0.265 | 0.015 | 0.195 | 0.008 | 0.219 | 0.015 | 0.205 | 0.015 | 0.165 | 0.011 |
| M22 | 0.933 | 0.077 | 0.702 | 0.036 | 0.753 | 0.061 | 0.738 | 0.066 | 0.620 | 0.057 |
| M23 | 0.018 | 0.001 | 0.014 | 0.001 | 0.015 | 0.001 | 0.014 | 0.001 | 0.013 | 0.001 |
| M24 | 0.103 | 0.009 | 0.073 | 0.004 | 0.079 | 0.008 | 0.073 | 0.007 | 0.067 | 0.008 |
| M25 | 0.241 | 0.013 | 0.211 | 0.007 | 0.218 | 0.013 | 0.212 | 0.014 | 0.204 | 0.011 |
| M26 | 0.069 | 0.003 | 0.073 | 0.002 | 0.076 | 0.003 | 0.072 | 0.004 | 0.072 | 0.003 |

TABLE 6a

Ratio and T-test values between females of various levels of dementia

| Metabolite Code | AD, All to CN, Female | | ADAS 5-19 to CN, Female | | ADAS 20-39 to CN, Female | | ADAS 40-70 to CN, Female | |
|---|---|---|---|---|---|---|---|---|
| | Ratio | ttest | Ratio | ttest | Ratio | ttest | Ratio | ttest |
| M01 | 0.963 | 5.2E-01 | 0.929 | 2.1E-01 | 0.951 | 4.4E-01 | 1.004 | 9.6E-01 |
| M02 | 0.856 | 9.0E-02 | 0.806 | 4.5E-02 | 0.912 | 3.9E-01 | 0.833 | 1.2E-01 |
| M03 | 0.772 | 5.2E-05 | 0.814 | 6.0E-03 | 0.775 | 8.0E-04 | 0.737 | 1.8E-04 |
| M04 | 0.963 | 7.5E-01 | 0.912 | 3.8E-01 | 1.027 | 8.3E-01 | 0.932 | 6.2E-01 |
| M05 | 0.893 | 1.1E-01 | 0.925 | 3.4E-01 | 0.895 | 2.1E-01 | 0.867 | 8.4E-02 |
| M06 | 0.843 | 1.4E-02 | 0.910 | 2.2E-01 | 0.869 | 9.8E-02 | 0.761 | 5.1E-04 |
| M07 | 0.732 | 1.8E-03 | 0.798 | 5.9E-02 | 0.753 | 2.0E-02 | 0.656 | 1.1E-03 |
| M08 | 0.821 | 5.0E-02 | 0.849 | 1.4E-01 | 0.889 | 3.7E-01 | 0.722 | 4.7E-03 |
| M09 | 0.696 | 2.6E-04 | 0.777 | 3.9E-02 | 0.702 | 2.9E-03 | 0.624 | 4.3E-04 |
| M10 | 0.877 | 3.1E-02 | 0.895 | 8.6E-02 | 0.860 | 4.1E-02 | 0.883 | 9.8E-02 |
| M11 | 0.832 | 2.5E-03 | 0.894 | 7.5E-02 | 0.850 | 2.7E-02 | 0.762 | 1.4E-04 |
| M12 | 0.778 | 5.3E-04 | 0.847 | 4.2E-02 | 0.776 | 4.7E-03 | 0.726 | 5.8E-04 |
| M13 | 0.800 | 8.5E-04 | 0.834 | 2.5E-02 | 0.794 | 8.6E-03 | 0.780 | 3.2E-03 |
| M14 | 0.772 | 4.8E-03 | 0.869 | 1.9E-01 | 0.746 | 3.0E-03 | 0.724 | 5.6E-03 |
| M15 | 0.811 | 8.5E-04 | 0.835 | 1.5E-02 | 0.831 | 2.3E-02 | 0.770 | 4.4E-04 |
| M16 | 0.765 | 7.5E-05 | 0.853 | 4.3E-02 | 0.801 | 6.9E-03 | 0.656 | 6.4E-08 |
| M17 | 0.705 | 3.5E-04 | 0.776 | 3.2E-02 | 0.745 | 1.4E-02 | 0.605 | 4.3E-05 |
| M18 | 0.754 | 3.4E-03 | 0.804 | 5.9E-02 | 0.792 | 6.8E-02 | 0.673 | 7.9E-04 |
| M19 | 0.688 | 1.8E-04 | 0.768 | 2.5E-02 | 0.699 | 2.9E-03 | 0.612 | 7.0E-05 |
| M20 | 0.768 | 4.9E-04 | 0.828 | 3.0E-02 | 0.782 | 1.1E-02 | 0.703 | 4.8E-05 |
| M21 | 0.737 | 1.9E-04 | 0.826 | 3.7E-02 | 0.776 | 1.1E-02 | 0.624 | 6.8E-07 |
| M22 | 0.752 | 5.2E-03 | 0.807 | 7.0E-02 | 0.790 | 6.1E-02 | 0.665 | 1.3E-03 |
| M23 | 0.764 | 2.5E-03 | 0.809 | 3.2E-02 | 0.789 | 4.1E-02 | 0.699 | 7.8E-04 |
| M24 | 0.708 | 2.5E-03 | 0.768 | 4.5E-02 | 0.713 | 9.3E-03 | 0.654 | 4.2E-03 |
| M25 | 0.876 | 6.6E-02 | 0.907 | 2.3E-01 | 0.880 | 1.5E-01 | 0.847 | 3.5E-02 |
| M26 | 1.056 | 3.8E-01 | 1.092 | 1.8E-01 | 1.043 | 5.8E-01 | 1.041 | 5.5E-01 |

TABLE 6b

Ratio and T-test values between females of various levels of dementia

| | ADAS 20-39 to 5-19, Female | | ADAS 40-70 to 5-19, Female | | ADAS 40-70 to 20-39, Female | |
|---|---|---|---|---|---|---|
| Metabolite Code | Ratio | ttest | Ratio | ttest | Ratio | ttest |
| M01 | 1.023 | 7.2E−01 | 1.080 | 2.8E−01 | 1.056 | 4.4E−01 |
| M02 | 1.132 | 2.3E−01 | 1.034 | 7.6E−01 | 0.914 | 4.1E−01 |
| M03 | 0.951 | 5.1E−01 | 0.906 | 2.2E−01 | 0.952 | 5.3E−01 |
| M04 | 1.126 | 3.6E−01 | 1.022 | 8.8E−01 | 0.907 | 5.0E−01 |
| M05 | 0.967 | 7.0E−01 | 0.936 | 4.2E−01 | 0.968 | 7.1E−01 |
| M06 | 0.955 | 5.9E−01 | 0.837 | 2.5E−02 | 0.876 | 1.2E−01 |
| M07 | 0.944 | 6.4E−01 | 0.822 | 1.2E−01 | 0.871 | 2.8E−01 |
| M08 | 1.046 | 7.2E−01 | 0.850 | 1.1E−01 | 0.812 | 1.1E−01 |
| M09 | 0.903 | 3.9E−01 | 0.802 | 9.5E−02 | 0.889 | 3.5E−01 |
| M10 | 0.961 | 5.8E−01 | 0.987 | 8.6E−01 | 1.027 | 7.2E−01 |
| M11 | 0.951 | 5.1E−01 | 0.853 | 2.8E−02 | 0.896 | 1.6E−01 |
| M12 | 0.917 | 3.1E−01 | 0.858 | 7.7E−02 | 0.935 | 4.7E−01 |
| M13 | 0.953 | 5.4E−01 | 0.936 | 3.6E−01 | 0.982 | 8.2E−01 |
| M14 | 0.858 | 1.6E−01 | 0.833 | 1.5E−01 | 0.971 | 8.0E−01 |
| M15 | 0.996 | 9.6E−01 | 0.922 | 2.3E−01 | 0.926 | 3.1E−01 |
| M16 | 0.940 | 4.7E−01 | 0.769 | 9.7E−04 | 0.819 | 1.6E−02 |
| M17 | 0.960 | 7.4E−01 | 0.779 | 4.0E−02 | 0.812 | 9.8E−02 |
| M18 | 0.985 | 9.0E−01 | 0.837 | 7.6E−02 | 0.850 | 1.8E−01 |
| M19 | 0.911 | 4.7E−01 | 0.798 | 8.5E−02 | 0.875 | 3.1E−01 |
| M20 | 0.945 | 5.7E−01 | 0.849 | 5.8E−02 | 0.898 | 2.7E−01 |
| M21 | 0.939 | 5.5E−01 | 0.755 | 4.6E−03 | 0.804 | 4.1E−02 |
| M22 | 0.979 | 8.7E−01 | 0.824 | 1.2E−01 | 0.841 | 1.9E−01 |
| M23 | 0.975 | 8.3E−01 | 0.864 | 1.4E−01 | 0.886 | 3.0E−01 |
| M24 | 0.928 | 6.0E−01 | 0.852 | 3.2E−01 | 0.918 | 5.8E−01 |
| M25 | 0.971 | 7.5E−01 | 0.934 | 4.0E−01 | 0.962 | 6.6E−01 |
| M26 | 0.955 | 5.2E−01 | 0.954 | 4.5E−01 | 0.998 | 9.8E−01 |

TABLE 7

Effect of Pathology State on Serum Ethanolamine Phospholipid Levels in Females

| | Post Mortem Ctl, Female | | Post Mortem SDAT Female | | Autopsy AD vs. Control, Female | |
|---|---|---|---|---|---|---|
| Metabolite Code | Mean | SEM | Mean | SEM | Ratio | ttest |
| M01 | 0.179 | 0.050 | 0.124 | 0.016 | 0.697 | 0.300 |
| M02 | 0.062 | 0.022 | 0.048 | 0.011 | 0.773 | 0.557 |
| M03 | 0.070 | 0.019 | 0.043 | 0.005 | 0.619 | 0.178 |
| M04 | 0.016 | 0.005 | 0.012 | 0.004 | 0.775 | 0.563 |
| M05 | 0.007 | 0.002 | 0.003 | 0.001 | 0.508 | 0.095 |
| M06 | 0.011 | 0.003 | 0.004 | 0.001 | 0.531 | 0.060 |
| M07 | 0.016 | 0.003 | 0.005 | 0.001 | 0.530 | 0.037 |
| M08 | 0.003 | 0.001 | 0.001 | 0.000 | 0.684 | 0.258 |
| M09 | 0.005 | 0.001 | 0.002 | 0.000 | 0.566 | 0.047 |
| M10 | 0.053 | 0.015 | 0.025 | 0.004 | 0.672 | 0.293 |
| M11 | 0.064 | 0.013 | 0.025 | 0.004 | 0.650 | 0.132 |
| M12 | 0.114 | 0.021 | 0.055 | 0.008 | 0.742 | 0.241 |
| M13 | 0.010 | 0.002 | 0.005 | 0.001 | 0.865 | 0.537 |
| M14 | 0.023 | 0.004 | 0.011 | 0.002 | 0.904 | 0.792 |
| M15 | 0.060 | 0.017 | 0.034 | 0.004 | 0.577 | 0.151 |
| M16 | 0.107 | 0.021 | 0.064 | 0.008 | 0.594 | 0.061 |
| M17 | 0.113 | 0.024 | 0.067 | 0.009 | 0.592 | 0.079 |
| M18 | 0.014 | 0.004 | 0.008 | 0.001 | 0.579 | 0.186 |
| M19 | 0.035 | 0.007 | 0.022 | 0.004 | 0.635 | 0.132 |
| M20 | 0.050 | 0.014 | 0.021 | 0.002 | 0.410 | 0.042 |
| M21 | 0.100 | 0.020 | 0.041 | 0.007 | 0.414 | 0.010 |
| M22 | 0.283 | 0.058 | 0.168 | 0.024 | 0.593 | 0.071 |
| M23 | 0.012 | 0.003 | 0.007 | 0.001 | 0.560 | 0.112 |
| M24 | 0.035 | 0.007 | 0.018 | 0.002 | 0.496 | 0.025 |
| M25 | 0.189 | 0.015 | 0.198 | 0.022 | 1.051 | 0.727 |
| M26 | 0.054 | 0.008 | 0.061 | 0.006 | 1.123 | 0.496 |

TABLE 8

Effect of Age on Serum Ethanolamine Phospholipid Levels in Males

| Metabolite Code | Age Ctl, 30-39, Male | | Age Ctl, 40-49, Male | | Age Ctl, 50-59, Male | | Age Ctl, 60-69, Male | | Age Ctl, 70+, Male | |
|---|---|---|---|---|---|---|---|---|---|---|
| | Mean | SEM | Mean | SEM | Mean | SEM | Mean | SEM | Mean | SEM |
| M01 | 0.122 | 0.017 | 0.119 | 0.008 | 0.113 | 0.006 | 0.132 | 0.007 | 0.130 | 0.006 |
| M02 | 0.056 | 0.008 | 0.058 | 0.006 | 0.058 | 0.004 | 0.059 | 0.007 | 0.056 | 0.005 |
| M03 | 0.102 | 0.014 | 0.085 | 0.006 | 0.095 | 0.005 | 0.103 | 0.008 | 0.110 | 0.010 |
| M04 | 0.026 | 0.004 | 0.027 | 0.003 | 0.025 | 0.002 | 0.027 | 0.003 | 0.027 | 0.003 |
| M05 | 0.014 | 0.002 | 0.012 | 0.001 | 0.011 | 0.001 | 0.012 | 0.001 | 0.011 | 0.001 |
| M06 | 0.032 | 0.005 | 0.026 | 0.002 | 0.026 | 0.001 | 0.025 | 0.002 | 0.027 | 0.002 |
| M07 | 0.078 | 0.015 | 0.053 | 0.007 | 0.063 | 0.005 | 0.061 | 0.007 | 0.060 | 0.006 |
| M08 | 0.010 | 0.002 | 0.007 | 0.001 | 0.007 | 0.001 | 0.007 | 0.001 | 0.006 | 0.001 |
| M09 | 0.019 | 0.004 | 0.013 | 0.002 | 0.019 | 0.002 | 0.019 | 0.002 | 0.022 | 0.003 |
| M10 | 0.058 | 0.009 | 0.052 | 0.004 | 0.049 | 0.003 | 0.055 | 0.004 | 0.053 | 0.003 |
| M11 | 0.131 | 0.021 | 0.099 | 0.007 | 0.098 | 0.005 | 0.099 | 0.007 | 0.104 | 0.007 |
| M12 | 0.244 | 0.037 | 0.186 | 0.015 | 0.210 | 0.012 | 0.213 | 0.017 | 0.202 | 0.016 |
| M13 | 0.015 | 0.002 | 0.013 | 0.001 | 0.013 | 0.001 | 0.013 | 0.001 | 0.012 | 0.001 |
| M14 | 0.034 | 0.005 | 0.026 | 0.003 | 0.036 | 0.002 | 0.040 | 0.004 | 0.047 | 0.006 |
| M15 | 0.085 | 0.012 | 0.075 | 0.005 | 0.074 | 0.004 | 0.074 | 0.006 | 0.076 | 0.005 |
| M16 | 0.291 | 0.043 | 0.220 | 0.016 | 0.244 | 0.013 | 0.223 | 0.018 | 0.246 | 0.018 |
| M17 | 0.489 | 0.102 | 0.332 | 0.035 | 0.429 | 0.029 | 0.412 | 0.048 | 0.410 | 0.044 |
| M18 | 0.032 | 0.005 | 0.025 | 0.003 | 0.027 | 0.002 | 0.026 | 0.004 | 0.023 | 0.002 |
| M19 | 0.086 | 0.014 | 0.063 | 0.008 | 0.094 | 0.008 | 0.098 | 0.012 | 0.114 | 0.017 |
| M20 | 0.086 | 0.013 | 0.070 | 0.006 | 0.068 | 0.004 | 0.069 | 0.006 | 0.071 | 0.006 |
| M21 | 0.294 | 0.044 | 0.236 | 0.017 | 0.247 | 0.014 | 0.222 | 0.018 | 0.236 | 0.018 |
| M22 | 1.054 | 0.220 | 0.788 | 0.079 | 0.930 | 0.067 | 0.933 | 0.102 | 0.906 | 0.104 |
| M23 | 0.022 | 0.003 | 0.019 | 0.001 | 0.019 | 0.001 | 0.020 | 0.003 | 0.017 | 0.001 |
| M24 | 0.077 | 0.014 | 0.063 | 0.008 | 0.086 | 0.007 | 0.088 | 0.010 | 0.103 | 0.016 |
| M25 | 0.205 | 0.014 | 0.195 | 0.017 | 0.274 | 0.018 | 0.310 | 0.025 | 0.374 | 0.031 |
| M26 | 0.091 | 0.011 | 0.082 | 0.005 | 0.096 | 0.003 | 0.109 | 0.009 | 0.114 | 0.009 |

TABLE 9

Ratio and T-test values between males of different ages

| Metabolite Code | 50-59 vs. 40-49, Male | | 60-69 vs. 40-49, Male | | 70+ vs. 40-49, Male | |
|---|---|---|---|---|---|---|
| | Ratio | ttest | Ratio | ttest | Ratio | ttest |
| M01 | 0.955 | 6.0E−01 | 1.110 | 2.2E−01 | 1.097 | 2.4E−01 |
| M02 | 0.998 | 9.9E−01 | 1.024 | 8.8E−01 | 0.965 | 8.1E−01 |
| M03 | 1.125 | 2.3E−01 | 1.213 | 9.4E−02 | 1.296 | 5.0E−02 |
| M04 | 0.954 | 7.0E−01 | 1.019 | 9.1E−01 | 1.015 | 9.3E−01 |
| M05 | 0.953 | 6.3E−01 | 1.011 | 9.3E−01 | 0.979 | 8.5E−01 |
| M06 | 1.031 | 7.5E−01 | 0.976 | 8.3E−01 | 1.054 | 6.2E−01 |
| M07 | 1.198 | 2.4E−01 | 1.164 | 4.1E−01 | 1.133 | 4.8E−01 |
| M08 | 1.031 | 8.2E−01 | 1.014 | 9.4E−01 | 0.907 | 5.4E−01 |
| M09 | 1.443 | 2.7E−02 | 1.473 | 4.5E−02 | 1.701 | 2.1E−02 |
| M10 | 0.953 | 5.9E−01 | 1.061 | 5.9E−01 | 1.013 | 8.9E−01 |
| M11 | 0.992 | 9.3E−01 | 1.004 | 9.7E−01 | 1.058 | 5.6E−01 |
| M12 | 1.128 | 2.5E−01 | 1.147 | 2.5E−01 | 1.085 | 4.8E−01 |
| M13 | 1.007 | 9.4E−01 | 1.032 | 8.0E−01 | 0.921 | 4.4E−01 |
| M14 | 1.383 | 1.5E−02 | 1.536 | 7.0E−03 | 1.802 | 2.8E−03 |
| M15 | 0.987 | 8.9E−01 | 0.985 | 8.9E−01 | 1.020 | 8.5E−01 |
| M16 | 1.109 | 2.7E−01 | 1.013 | 9.1E−01 | 1.118 | 2.9E−01 |
| M17 | 1.291 | 5.4E−02 | 1.241 | 2.1E−01 | 1.235 | 1.9E−01 |
| M18 | 1.055 | 6.6E−01 | 1.032 | 8.7E−01 | 0.904 | 4.9E−01 |
| M19 | 1.484 | 1.9E−02 | 1.540 | 2.6E−02 | 1.789 | 1.9E−02 |
| M20 | 0.971 | 7.8E−01 | 0.976 | 8.4E−01 | 1.014 | 9.0E−01 |
| M21 | 1.048 | 6.3E−01 | 0.941 | 5.8E−01 | 1.000 | 1.0E+00 |
| M22 | 1.179 | 2.1E−01 | 1.183 | 2.9E−01 | 1.149 | 3.9E−01 |
| M23 | 1.008 | 9.3E−01 | 1.066 | 7.5E−01 | 0.900 | 3.6E−01 |
| M24 | 1.365 | 5.2E−02 | 1.403 | 6.0E−02 | 1.642 | 4.7E−02 |
| M25 | 1.405 | 9.0E−03 | 1.589 | 6.7E−04 | 1.912 | 1.7E−05 |
| M26 | 1.175 | 1.8E−02 | 1.324 | 1.7E−02 | 1.389 | 6.3E−03 |

TABLE 10

Effect of Age on Serum Ethanolamine Phospholipid Levels in Females

| | Age Ctl, 30-39, Female | | Age Ctl, 40-49, Female | | Age Ctl, 50-59, Female | | Age Ctl, 60-69, Female | | Age Ctl, 70+, Female | |
|---|---|---|---|---|---|---|---|---|---|---|
| Metabolite Code | Mean | SEM | Mean | SEM | Mean | SEM | Mean | SEM | Mean | SEM |
| M01 | 0.103 | 0.012 | 0.114 | 0.006 | 0.105 | 0.006 | 0.127 | 0.007 | 0.126 | 0.009 |
| M02 | 0.047 | 0.006 | 0.069 | 0.006 | 0.058 | 0.004 | 0.058 | 0.004 | 0.056 | 0.004 |
| M03 | 0.095 | 0.015 | 0.101 | 0.007 | 0.093 | 0.005 | 0.091 | 0.006 | 0.100 | 0.005 |
| M04 | 0.028 | 0.005 | 0.033 | 0.003 | 0.025 | 0.002 | 0.023 | 0.002 | 0.026 | 0.002 |
| M05 | 0.011 | 0.002 | 0.013 | 0.001 | 0.010 | 0.000 | 0.010 | 0.001 | 0.011 | 0.001 |
| M06 | 0.031 | 0.005 | 0.031 | 0.002 | 0.025 | 0.001 | 0.023 | 0.001 | 0.025 | 0.002 |
| M07 | 0.061 | 0.010 | 0.071 | 0.007 | 0.057 | 0.003 | 0.051 | 0.005 | 0.052 | 0.005 |
| M08 | 0.008 | 0.001 | 0.010 | 0.001 | 0.007 | 0.000 | 0.006 | 0.001 | 0.006 | 0.001 |
| M09 | 0.021 | 0.004 | 0.021 | 0.002 | 0.020 | 0.001 | 0.017 | 0.002 | 0.019 | 0.002 |
| M10 | 0.050 | 0.007 | 0.059 | 0.003 | 0.049 | 0.002 | 0.052 | 0.003 | 0.051 | 0.003 |
| M11 | 0.120 | 0.018 | 0.119 | 0.008 | 0.100 | 0.004 | 0.099 | 0.006 | 0.100 | 0.008 |
| M12 | 0.196 | 0.022 | 0.222 | 0.015 | 0.191 | 0.009 | 0.181 | 0.011 | 0.188 | 0.013 |
| M13 | 0.013 | 0.001 | 0.015 | 0.001 | 0.012 | 0.001 | 0.011 | 0.001 | 0.012 | 0.001 |
| M14 | 0.040 | 0.007 | 0.043 | 0.004 | 0.042 | 0.003 | 0.041 | 0.003 | 0.049 | 0.004 |
| M15 | 0.071 | 0.009 | 0.079 | 0.005 | 0.068 | 0.003 | 0.066 | 0.004 | 0.069 | 0.004 |
| M16 | 0.274 | 0.044 | 0.268 | 0.021 | 0.226 | 0.011 | 0.210 | 0.013 | 0.232 | 0.017 |
| M17 | 0.419 | 0.076 | 0.458 | 0.053 | 0.392 | 0.024 | 0.354 | 0.036 | 0.360 | 0.033 |
| M18 | 0.028 | 0.004 | 0.032 | 0.003 | 0.025 | 0.002 | 0.019 | 0.002 | 0.023 | 0.003 |
| M19 | 0.107 | 0.024 | 0.100 | 0.012 | 0.099 | 0.007 | 0.087 | 0.009 | 0.103 | 0.008 |
| M20 | 0.074 | 0.013 | 0.075 | 0.006 | 0.063 | 0.003 | 0.063 | 0.004 | 0.068 | 0.005 |
| M21 | 0.294 | 0.057 | 0.275 | 0.024 | 0.228 | 0.012 | 0.210 | 0.014 | 0.229 | 0.020 |
| M22 | 0.938 | 0.170 | 1.025 | 0.108 | 0.853 | 0.055 | 0.759 | 0.068 | 0.837 | 0.096 |
| M23 | 0.021 | 0.003 | 0.022 | 0.002 | 0.017 | 0.001 | 0.015 | 0.001 | 0.017 | 0.002 |
| M24 | 0.102 | 0.025 | 0.093 | 0.011 | 0.089 | 0.006 | 0.081 | 0.008 | 0.096 | 0.008 |
| M25 | 0.239 | 0.023 | 0.236 | 0.014 | 0.277 | 0.012 | 0.326 | 0.022 | 0.373 | 0.020 |
| M26 | 0.091 | 0.012 | 0.093 | 0.006 | 0.093 | 0.003 | 0.094 | 0.004 | 0.107 | 0.007 |

TABLE 11

Ratio and T-test values between females of different ages

| | 50-59 vs. 40-49, Female | | 60-69 vs. 40-49, Female | | 70+ vs. 40-49, Female | |
|---|---|---|---|---|---|---|
| Metabolite Code | Ratio | ttest | Ratio | ttest | Ratio | ttest |
| M01 | 0.925 | 3.7E−01 | 1.118 | 1.8E−01 | 1.110 | 2.6E−01 |
| M02 | 0.838 | 1.3E−01 | 0.835 | 9.5E−02 | 0.812 | 1.1E−01 |
| M03 | 0.927 | 4.0E−01 | 0.906 | 2.9E−01 | 0.989 | 9.0E−01 |
| M04 | 0.772 | 2.1E−02 | 0.709 | 5.1E−03 | 0.811 | 1.2E−01 |
| M05 | 0.811 | 1.1E−02 | 0.798 | 2.0E−02 | 0.832 | 8.7E−02 |
| M06 | 0.815 | 1.1E−02 | 0.731 | 1.5E−03 | 0.805 | 5.7E−02 |
| M07 | 0.798 | 3.4E−02 | 0.718 | 1.9E−02 | 0.726 | 4.9E−02 |
| M08 | 0.721 | 4.2E−03 | 0.569 | 1.3E−04 | 0.640 | 1.9E−02 |
| M09 | 0.934 | 5.8E−01 | 0.784 | 9.4E−02 | 0.912 | 5.6E−01 |
| M10 | 0.841 | 3.1E−02 | 0.882 | 1.3E−01 | 0.863 | 1.1E−01 |
| M11 | 0.843 | 2.3E−02 | 0.832 | 3.5E−02 | 0.843 | 1.1E−01 |
| M12 | 0.862 | 6.2E−02 | 0.815 | 2.5E−02 | 0.848 | 1.2E−01 |
| M13 | 0.806 | 8.8E−03 | 0.737 | 2.0E−03 | 0.839 | 1.3E−01 |
| M14 | 0.981 | 8.6E−01 | 0.953 | 6.9E−01 | 1.149 | 2.6E−01 |
| M15 | 0.864 | 5.6E−02 | 0.841 | 3.7E−02 | 0.871 | 1.5E−01 |
| M16 | 0.846 | 5.3E−02 | 0.786 | 1.5E−02 | 0.867 | 2.3E−01 |
| M17 | 0.856 | 2.0E−01 | 0.773 | 1.0E−01 | 0.786 | 1.9E−01 |
| M18 | 0.778 | 2.4E−02 | 0.594 | 1.8E−04 | 0.733 | 7.4E−02 |
| M19 | 0.986 | 9.2E−01 | 0.872 | 3.8E−01 | 1.030 | 8.5E−01 |
| M20 | 0.843 | 5.6E−02 | 0.842 | 9.5E−02 | 0.905 | 4.0E−01 |
| M21 | 0.829 | 5.0E−02 | 0.763 | 1.8E−02 | 0.832 | 1.9E−01 |
| M22 | 0.832 | 1.2E−01 | 0.741 | 3.3E−02 | 0.817 | 2.3E−01 |
| M23 | 0.797 | 1.5E−02 | 0.663 | 3.3E−04 | 0.776 | 7.4E−02 |
| M24 | 0.957 | 7.4E−01 | 0.871 | 3.6E−01 | 1.040 | 8.1E−01 |
| M25 | 1.176 | 4.8E−02 | 1.381 | 1.7E−03 | 1.581 | 2.4E−07 |
| M26 | 1.003 | 9.6E−01 | 1.021 | 7.9E−01 | 1.159 | 1.2E−01 |

TABLE 12

Effect of Dementia State on White and Gray Matter Scores in Males

| Cohort | White Matter Score Mean | SEM | Gray Matter Score Mean | SEM |
|---|---|---|---|---|
| Cognitive Normal, Male | −0.25 | 0.08 | −0.44 | 0.11 |
| SDAT_all, Male | −0.63 | 0.06 | −1.11 | 0.08 |
| SDAT, ADAS 5-19, Male | −0.56 | 0.09 | −1.00 | 0.13 |
| SDAT, ADAS 20-39, Male | −0.67 | 0.08 | −1.11 | 0.10 |
| SDAT, ADAS 40-70, Male | −0.71 | 0.14 | −1.45 | 0.16 |
| Post Mortem Ctl, Male | −0.44 | 0.13 | −0.41 | 0.21 |
| Post Mortem SDAT Male | −1.62 | 0.19 | −1.28 | 0.23 |

| Comparison | White Matter Score | | Gray Matter Score | |
|---|---|---|---|---|
| AD, All to CN, Male | Delta | −0.37 | Delta | −0.67 |
| | ttest | 1.9E−03 | ttest | 2.4E−05 |
| ADAS 5-19 to CN, Male | Delta | −0.31 | Delta | −0.56 |
| | ttest | 1.8E−02 | ttest | 2.5E−03 |
| ADAS 20-39 to CN, Male | Delta | −0.41 | Delta | −0.67 |
| | ttest | 1.5E−03 | ttest | 7.8E−05 |
| ADAS 40-70 to CN, Male | Delta | −0.46 | Delta | −1.01 |
| | ttest | 3.7E−03 | ttest | 1.8E−06 |
| ADAS 20-39 to 5-19, Male | Delta | −0.10 | Delta | −0.11 |
| | ttest | 4.2E−01 | ttest | 5.0E−01 |
| ADAS 40-70 to 5-19, Male | Delta | −0.15 | Delta | −0.45 |
| | ttest | 3.9E−01 | ttest | 5.2E−02 |
| ADAS 40-70 to 20-39, Male | Delta | −0.04 | Delta | −0.34 |
| | ttest | 8.0E−01 | ttest | 1.1E−01 |
| Autopsy AD vs. Control, Male | Delta | −0.89 | Delta | −1.13 |
| | ttest | 8.9E−03 | ttest | 2.8E−03 |

TABLE 13

Effect of Dementia State on White and Gray Matter Scores in Females

| Cohort | White Matter Score Mean | SEM | Gray Matter Score Mean | SEM |
|---|---|---|---|---|
| Cognitive Normal, Female | −0.27 | 0.09 | −0.42 | 0.13 |
| SDAT_all, Female | −0.73 | 0.05 | −1.01 | 0.07 |
| SDAT, ADAS 5-19, Female | −0.55 | 0.08 | −0.85 | 0.11 |
| SDAT, ADAS 20-39, Female | −0.69 | 0.09 | −0.94 | 0.11 |
| SDAT, ADAS 40-70, Female | −0.91 | 0.08 | −1.21 | 0.12 |
| Post Mortem Ctl, Female | −0.50 | 0.29 | −0.53 | 0.26 |
| Post Mortem SDAT Female | −1.34 | 0.27 | −1.54 | 0.25 |

| Comparison | White Matter Score | | Gray Matter Score | |
|---|---|---|---|---|
| AD, All to CN, Female | Delta | −0.46 | Delta | −0.59 |
| | ttest | 4.6E−05 | ttest | 1.1E−04 |
| ADAS 5-19 to CN, Female | Delta | −0.29 | Delta | −0.43 |
| | ttest | 1.7E−02 | ttest | 1.3E−02 |
| ADAS 20-39 to CN, Female | Delta | −0.43 | Delta | −0.52 |
| | ttest | 1.9E−03 | ttest | 3.6E−03 |
| ADAS 40-70 to CN, Female | Delta | −0.64 | Delta | −0.79 |
| | ttest | 9.5E−07 | ttest | 2.2E−05 |
| ADAS 20-39 to 5-19, Female | Delta | −0.14 | Delta | −0.09 |
| | ttest | 2.7E−01 | ttest | 5.8E−01 |
| ADAS 40-70 to 5-19, Female | Delta | −0.36 | Delta | −0.37 |
| | ttest | 2.9E−03 | ttest | 3.1E−02 |
| ADAS 40-70 to 20-39, Female | Delta | −0.21 | Delta | −0.27 |
| | ttest | 9.4E−02 | ttest | 1.0E−01 |
| Autopsy AD vs. Control, Female | Delta | −1.17 | Delta | −0.81 |
| | ttest | 2.0E−03 | ttest | 2.5E−02 |

TABLE 14

Distribution of White and Gray Matter Scores in Males (Mean Normalized to CN Male)

| Bin | MMSE ≥ 28 Frequency | ADAS-cog 8-19 Frequency | ADAS-cog 20-39 Frequency | ADAS-cog 40-70 Frequency | Autopsy Control Frequency | Autopsy AD Frequency |
|---|---|---|---|---|---|---|
| White Matter Distribution | | | | | | |
| −2 | 0 | 1 | 1 | 0 | 0 | 2 |
| −1.75 | 0 | 0 | 0 | 0 | 0 | 0 |
| −1.5 | 0 | 0 | 3 | 1 | 0 | 0 |
| −1.25 | 0 | 2 | 4 | 0 | 0 | 1 |
| −1 | 1 | 2 | 3 | 1 | 0 | 2 |
| −0.75 | 1 | 3 | 3 | 4 | 0 | 2 |
| −0.5 | 3 | 2 | 6 | 4 | 2 | 0 |
| −0.25 | 3 | 8 | 13 | 4 | 3 | 1 |
| 0 | 7 | 13 | 12 | 0 | 2 | 1 |
| 0.25 | 9 | 6 | 5 | 1 | 2 | 1 |
| 0.5 | 5 | 1 | 5 | 2 | 0 | 0 |
| 0.75 | 1 | 0 | 1 | 0 | 1 | 0 |
| 1 | 2 | 0 | 2 | 1 | 0 | 0 |
| More | 0 | 2 | 0 | 0 | 0 | 0 |
| Gray Matter distribution | | | | | | |
| −2 | 0 | 1 | 4 | 2 | 0 | 2 |
| −1.75 | 0 | 2 | 2 | 1 | 0 | 0 |
| −1.5 | 0 | 1 | 3 | 0 | 0 | 0 |
| −1.25 | 1 | 4 | 2 | 2 | 0 | 1 |
| −1 | 0 | 6 | 7 | 4 | 0 | 2 |
| −0.75 | 1 | 4 | 9 | 2 | 1 | 3 |
| −0.5 | 7 | 3 | 5 | 4 | 1 | 1 |
| −0.25 | 3 | 5 | 9 | 1 | 2 | 0 |
| 0 | 3 | 2 | 7 | 1 | 1 | 0 |
| 0.25 | 5 | 4 | 2 | 1 | 3 | 0 |
| 0.5 | 7 | 3 | 4 | 0 | 1 | 1 |
| 0.75 | 3 | 1 | 2 | 0 | 0 | 0 |

TABLE 14-continued

Distribution of White and Gray Matter Scores
in Males (Mean Normalized to CN Male)

| Bin | MMSE ≥ 28 Frequency | ADAS-cog 8-19 Frequency | ADAS-cog 20-39 Frequency | ADAS-cog 40-70 Frequency | Autopsy Control Frequency | Autopsy AD Frequency |
|---|---|---|---|---|---|---|
| 1 | 0 | 3 | 2 | 0 | 0 | 0 |
| More | 2 | 1 | 0 | 0 | 1 | 0 |

TABLE 15

Risk prediction in Males
Stats

| | | CN White Matter Score Control Normalized | Low White Matter Score Control Normalized | Moderate White Matter Score Control Normalized | Severe White Matter Score Control Normalized | PM Ctl White Matter Score Control Normalized | PM SDAT White Matter Score Control Normalized |
|---|---|---|---|---|---|---|---|
| Total N | | 32 | 40 | 58 | 18 | 10 | 10 |
| Total L | | 27 | 30 | 38 | 8 | 8 | 3 |
| Total H | | 5 | 10 | 20 | 10 | 2 | 7 |
| L % | | 84.4 | 75.0 | 65.5 | 44.4 | 80.0 | 30.0 |
| | | Gray Matter Score Control Normalized | Gray Matter Score Control Normalized | Gray Matter Score Control Normalized | Gray Matter Score Control Normalized | Gray Matter Score Control Normalized | Gray Matter Score Control Normalized |
| | Total N | 32 | 40 | 58 | 18 | 10 | 10 |
| | Total L | 23 | 19 | 26 | 3 | 8 | 1 |
| | Total H | 9 | 21 | 32 | 15 | 2 | 9 |
| | L % | 71.9 | 47.5 | 44.8 | 16.7 | 80.0 | 10.0 |
| Low risk | LL | 22 | 19 | 25 | 3 | 7 | 1 |
| % | LL | 68.8 | 47.5 | 43.1 | 16.7 | 70.0 | 10.0 |
| Intermediate risk | IM | 6 | 11 | 14 | 5 | 2 | 2 |
| % | IM | 18.8 | 27.5 | 24.1 | 27.8 | 20.0 | 20.0 |
| High risk | HH | 4 | 10 | 19 | 10 | 1 | 7 |
| % | HH | 12.5 | 25.0 | 32.8 | 55.6 | 10.0 | 70.0 |

TABLE 16

Distribution of White and Gray Matter Scores
in Females (Mean Normalized to CN Female)

| Bin | MMSE ≥ 28 Frequency | ADAS-cog 8-19 Frequency | ADAS-cog 20-39 Frequency | ADAS-cog 40-70 Frequency | Autopsy Control Frequency | Autopsy AD Frequency |
|---|---|---|---|---|---|---|
| White Matter Distribution | | | | | | |
| -2 | 0 | 0 | 0 | 1 | 0 | 1 |
| -1.75 | 0 | 0 | 0 | 0 | 0 | 1 |
| -1.5 | 0 | 0 | 3 | 4 | 1 | 3 |
| -1.25 | 1 | 0 | 2 | 1 | 0 | 0 |
| -1 | 1 | 2 | 8 | 4 | 0 | 3 |
| -0.75 | 1 | 5 | 6 | 11 | 1 | 0 |
| -0.5 | 2 | 6 | 6 | 10 | 1 | 1 |
| -0.25 | 4 | 8 | 6 | 3 | 2 | 1 |
| 0 | 9 | 5 | 8 | 9 | 1 | 0 |
| 0.25 | 8 | 6 | 5 | 3 | 2 | 0 |
| 0.5 | 3 | 3 | 6 | 1 | 0 | 0 |
| 0.75 | 4 | 3 | 1 | 1 | 0 | 0 |
| 1 | 3 | 0 | 2 | 0 | 0 | 0 |
| More | 0 | 0 | 1 | 0 | 1 | 0 |
| Gray Matter distribution | | | | | | |
| -2 | 0 | 0 | 1 | 4 | 0 | 1 |
| -1.75 | 0 | 1 | 2 | 1 | 0 | 1 |

TABLE 16-continued

Distribution of White and Gray Matter Scores in Females (Mean Normalized to CN Female)

| Bin | MMSE ≥ 28 Frequency | ADAS-cog 8-19 Frequency | ADAS-cog 20-39 Frequency | ADAS-cog 40-70 Frequency | Autopsy Control Frequency | Autopsy AD Frequency |
|---|---|---|---|---|---|---|
| -1.5 | 1 | 1 | 3 | 6 | 0 | 0 |
| -1.25 | 2 | 2 | 4 | 6 | 0 | 0 |
| -1 | 2 | 3 | 8 | 4 | 1 | 2 |
| -0.75 | 1 | 5 | 6 | 5 | 0 | 1 |
| -0.5 | 1 | 6 | 4 | 6 | 1 | 2 |
| -0.25 | 5 | 6 | 7 | 3 | 2 | 0 |
| 0 | 4 | 5 | 4 | 3 | 2 | 2 |
| 0.25 | 6 | 3 | 6 | 6 | 2 | 1 |
| 0.5 | 5 | 2 | 2 | 1 | 0 | 0 |
| 0.75 | 3 | 1 | 2 | 2 | 0 | 0 |
| 1 | 3 | 2 | 2 | 0 | 0 | 0 |
| More | 3 | 1 | 3 | 1 | 1 | 0 |

TABLE 17

Risk Prediction in Females Stats

| | | CN White Matter Score Control Normalized | Low White Matter Score Control Normalized | Moderate White Matter Score Control Normalized | Severe White Matter Score Control Normalized | PM Ctl White Matter Score Control Normalized | PM SDAT White Matter Score Control Normalized |
|---|---|---|---|---|---|---|---|
| | Total N | 36 | 38 | 54 | 48 | 9 | 10 |
| | Total L | 31 | 25 | 29 | 17 | 6 | 1 |
| | Total H | 5 | 13 | 25 | 31 | 3 | 9 |
| | L % | 86.1 | 65.8 | 53.7 | 35.4 | 66.7 | 10.0 |

| | | Gray Matter Score Control Normalized | Gray Matter Score Control Normalized | Gray Matter Score Control Normalized | Gray Matter Score Control Normalized | Gray Matter Score Control Normalized | Gray Matter Score Control Normalized |
|---|---|---|---|---|---|---|---|
| | Total N | 36 | 38 | 54 | 48 | 9 | 10 |
| | Total L | 29 | 20 | 26 | 16 | 7 | 3 |
| | Total H | 7 | 18 | 28 | 32 | 2 | 7 |
| | L % | 80.6 | 52.6 | 48.1 | 33.3 | 77.8 | 30.0 |
| Low risk | LL | 29 | 17 | 24 | 11 | 5 | 0 |
| % | LL | 80.6 | 44.7 | 44.4 | 22.9 | 55.6 | 0.0 |
| Intermediate risk | IM | 2 | 11 | 7 | 11 | 3 | 4 |
| % | IM | 5.6 | 28.9 | 13.0 | 22.9 | 33.3 | 40.0 |
| High risk | HH | 5 | 10 | 23 | 26 | 1 | 6 |
| % | HH | 13.9 | 26.3 | 42.6 | 54.2 | 11.1 | 60.0 |

TABLE 18

Effect of Age on White and Gray Matter Scores in Males

| | White Matter Score | | Gray Matter Score | |
|---|---|---|---|---|
| Cohort | Mean | SEM | Mean | SEM |
| Age Ctl, 30-39, Male | -0.25 | 0.29 | -0.92 | 0.28 |
| Age Ctl, 40-49, Male | -0.48 | 0.10 | -1.28 | 0.14 |
| Age Ctl, 50-59, Male | -0.47 | 0.08 | -0.90 | 0.11 |
| Age Ctl, 60-69, Male | -0.53 | 0.10 | -0.84 | 0.14 |
| Age Ctl, 70+_Male | -0.43 | 0.09 | -0.78 | 0.14 |

| Comparison | White Matter Score | | Gray Matter Score | |
|---|---|---|---|---|
| 50-59 vs. 40-49, Male | Delta | 0.01 | Delta | 0.38 |
| | ttest | 9.4E-01 | ttest | 4.2E-02 |
| 60-69 vs. 40-49, Male | Delta | -0.05 | Delta | 0.45 |
| | ttest | 7.4E-01 | ttest | 3.2E-02 |
| 70+ vs. 40-49, Male | Delta | 0.05 | Delta | 0.50 |
| | ttest | 7.2E-01 | ttest | 1.4E-02 |

TABLE 19

Effect of Age on White and Gray Matter Scores in Females

| | White Matter Score | | Gray Matter Score | |
|---|---|---|---|---|
| Cohort | Mean | SEM | Mean | SEM |
| Age Ctl, 30-39, Female | -0.36 | 0.18 | -0.56 | 0.27 |
| Age Ctl, 40-49, Female | -0.33 | 0.10 | -0.61 | 0.13 |
| Age Ctl, 50-59, Female | -0.55 | 0.06 | -0.71 | 0.09 |

TABLE 19-continued

Effect of Age on White and Gray Matter Scores in Females

| | | | | |
|---|---|---|---|---|
| Age Ctl, 60-69, Female | −0.62 | 0.09 | −0.90 | 0.12 |
| Age Ctl, 70+_Female | −0.47 | 0.11 | −0.58 | 0.14 |
| Comparison | White Matter Score | | Gray Matter Score | |
| 50-59 vs. 40-49, Female | Delta | −0.22 | Delta | −0.10 |
| | ttest | 6.9E−02 | ttest | 5.4E−01 |
| 60-69 vs. 40-49, Female | Delta | −0.29 | Delta | −0.30 |
| | ttest | 3.6E−02 | ttest | 1.1E−01 |
| 70+ vs. 40-49, Female | Delta | −0.14 | Delta | 0.03 |
| | ttest | 3.7E−01 | ttest | 8.8E−01 |

TABLE 20

Average Serum Ethanolamine Phospholipid Ratios to M01 in Males of Different Levels of Dementia Severity

| | Cognitive Normal, Male | | SDAT_all, Male | | SDAT, ADAS 5-19, Male | | SDAT, ADAS 20-39, Male | | SDAT ADAS 40-70, Male | |
|---|---|---|---|---|---|---|---|---|---|---|
| Metabolite Code | Mean | SEM | Mean | SEM | Mean | SEM | Mean | SEM | Mean | SEM |
| M01 | 1.000 | 0.000 | 1.000 | 0.000 | 1.000 | 0.000 | 1.000 | 0.000 | 1.000 | 0.000 |
| M02 | 0.564 | 0.031 | 0.453 | 0.015 | 0.475 | 0.032 | 0.455 | 0.017 | 0.383 | 0.022 |
| M03 | 0.960 | 0.050 | 0.712 | 0.018 | 0.779 | 0.037 | 0.694 | 0.024 | 0.617 | 0.027 |
| M04 | 0.262 | 0.015 | 0.210 | 0.009 | 0.203 | 0.017 | 0.219 | 0.013 | 0.183 | 0.014 |
| M05 | 0.106 | 0.006 | 0.089 | 0.002 | 0.091 | 0.004 | 0.089 | 0.003 | 0.085 | 0.004 |
| M06 | 0.255 | 0.014 | 0.213 | 0.007 | 0.211 | 0.012 | 0.214 | 0.010 | 0.211 | 0.012 |
| M07 | 0.554 | 0.041 | 0.373 | 0.014 | 0.396 | 0.025 | 0.375 | 0.020 | 0.321 | 0.028 |
| M08 | 0.062 | 0.005 | 0.044 | 0.002 | 0.047 | 0.004 | 0.045 | 0.003 | 0.038 | 0.003 |
| M09 | 0.195 | 0.015 | 0.126 | 0.006 | 0.139 | 0.012 | 0.127 | 0.009 | 0.093 | 0.008 |
| M10 | 0.483 | 0.021 | 0.440 | 0.009 | 0.450 | 0.016 | 0.441 | 0.013 | 0.408 | 0.016 |
| M11 | 0.985 | 0.043 | 0.817 | 0.025 | 0.828 | 0.051 | 0.824 | 0.035 | 0.761 | 0.036 |
| M12 | 1.843 | 0.088 | 1.399 | 0.036 | 1.460 | 0.059 | 1.406 | 0.053 | 1.252 | 0.090 |
| M13 | 0.114 | 0.006 | 0.092 | 0.002 | 0.096 | 0.004 | 0.091 | 0.003 | 0.088 | 0.006 |
| M14 | 0.442 | 0.023 | 0.310 | 0.013 | 0.348 | 0.028 | 0.301 | 0.015 | 0.255 | 0.025 |
| M15 | 0.682 | 0.031 | 0.548 | 0.012 | 0.571 | 0.022 | 0.541 | 0.016 | 0.520 | 0.024 |
| M16 | 2.398 | 0.128 | 1.790 | 0.057 | 1.856 | 0.105 | 1.777 | 0.082 | 1.687 | 0.115 |
| M17 | 4.203 | 0.304 | 2.569 | 0.105 | 2.853 | 0.205 | 2.501 | 0.135 | 2.187 | 0.243 |
| M18 | 0.232 | 0.017 | 0.156 | 0.006 | 0.166 | 0.012 | 0.155 | 0.009 | 0.140 | 0.010 |
| M19 | 1.103 | 0.092 | 0.663 | 0.032 | 0.740 | 0.066 | 0.660 | 0.041 | 0.503 | 0.045 |
| M20 | 0.692 | 0.037 | 0.548 | 0.016 | 0.593 | 0.030 | 0.532 | 0.021 | 0.509 | 0.034 |
| M21 | 2.377 | 0.126 | 1.857 | 0.066 | 1.951 | 0.128 | 1.829 | 0.090 | 1.754 | 0.143 |
| M22 | 9.309 | 0.674 | 6.230 | 0.231 | 6.651 | 0.434 | 6.157 | 0.305 | 5.616 | 0.592 |
| M23 | 0.164 | 0.009 | 0.125 | 0.004 | 0.133 | 0.008 | 0.124 | 0.006 | 0.114 | 0.008 |
| M24 | 1.010 | 0.088 | 0.672 | 0.034 | 0.770 | 0.076 | 0.647 | 0.039 | 0.539 | 0.053 |
| M25 | 2.160 | 0.133 | 2.085 | 0.115 | 2.215 | 0.145 | 2.102 | 0.197 | 1.811 | 0.222 |

TABLE 21a

Ratio and T-test Values of Ethanolamine Phospholipid Ratios to M01 between Males of Various Levels of Dementia

| | AD, All to CN, Male | | ADAS 5-19 to CN, Male | | ADAS 20-39 to CN, Male | | ADAS 40-70 to CN, Male | |
|---|---|---|---|---|---|---|---|---|
| Metabolite Code | Ratio | ttest | Ratio | ttest | Ratio | ttest | Ratio | ttest |
| M01 | 1.000 | #DIV/0! | 1.000 | #DIV/0! | 1.000 | #DIV/0! | 1.000 | #DIV/0! |
| M02 | 0.803 | 7.2E−04 | 0.842 | 5.2E−02 | 0.807 | 1.2E−03 | 0.680 | 1.8E−04 |
| M03 | 0.742 | 6.4E−08 | 0.812 | 3.8E−03 | 0.724 | 4.5E−07 | 0.643 | 9.8E−06 |
| M04 | 0.802 | 8.4E−03 | 0.774 | 1.6E−02 | 0.836 | 4.1E−02 | 0.700 | 1.3E−03 |
| M05 | 0.840 | 9.2E−04 | 0.858 | 2.9E−02 | 0.841 | 5.5E−03 | 0.798 | 1.2E−02 |
| M06 | 0.833 | 5.0E−03 | 0.827 | 2.0E−02 | 0.840 | 2.2E−02 | 0.828 | 4.7E−02 |
| M07 | 0.673 | 4.7E−07 | 0.715 | 1.1E−03 | 0.676 | 3.1E−05 | 0.580 | 2.4E−04 |
| M08 | 0.713 | 1.1E−04 | 0.747 | 1.3E−02 | 0.727 | 1.5E−03 | 0.602 | 8.4E−04 |
| M09 | 0.645 | 2.8E−06 | 0.713 | 4.4E−03 | 0.654 | 7.5E−05 | 0.476 | 1.6E−05 |
| M10 | 0.910 | 3.4E−02 | 0.932 | 2.1E−01 | 0.913 | 8.0E−02 | 0.843 | 1.8E−02 |
| M11 | 0.830 | 1.9E−03 | 0.841 | 2.5E−02 | 0.837 | 5.8E−03 | 0.773 | 9.3E−04 |
| M12 | 0.759 | 3.4E−07 | 0.792 | 3.9E−04 | 0.763 | 1.9E−05 | 0.679 | 7.0E−05 |
| M13 | 0.811 | 1.0E−04 | 0.846 | 1.2E−02 | 0.802 | 4.0E−04 | 0.772 | 4.7E−03 |
| M14 | 0.701 | 4.1E−06 | 0.787 | 1.4E−02 | 0.680 | 1.1E−06 | 0.576 | 4.9E−06 |
| M15 | 0.803 | 2.7E−06 | 0.837 | 3.8E−03 | 0.792 | 2.4E−05 | 0.762 | 8.6E−04 |
| M16 | 0.747 | 4.3E−06 | 0.774 | 1.5E−02 | 0.741 | 4.8E−05 | 0.704 | 5.4E−04 |
| M17 | 0.611 | 2.1E−09 | 0.679 | 3.1E−04 | 0.595 | 7.2E−08 | 0.520 | 4.0E−05 |
| M18 | 0.672 | 9.8E−07 | 0.714 | 1.7E−03 | 0.666 | 2.3E−05 | 0.603 | 3.3E−04 |
| M19 | 0.601 | 6.5E−08 | 0.672 | 1.7E−03 | 0.599 | 2.1E−06 | 0.456 | 2.2E−05 |
| M20 | 0.793 | 9.1E−05 | 0.858 | 3.8E−02 | 0.769 | 1.0E−04 | 0.736 | 1.8E−03 |
| M21 | 0.782 | 3.7E−04 | 0.821 | 2.2E−02 | 0.770 | 5.6E−04 | 0.738 | 3.0E−03 |
| M22 | 0.669 | 2.0E−07 | 0.714 | 9.9E−04 | 0.661 | 4.8E−06 | 0.603 | 6.0E−04 |

TABLE 21a-continued

Ratio and T-test Values of Ethanolamine Phospholipid Ratios to M01 between Males of Various Levels of Dementia

| Metabolite Code | AD, All to CN, Male | | ADAS 5-19 to CN, Male | | ADAS 20-39 to CN, Male | | ADAS 40-70 to CN, Male | |
|---|---|---|---|---|---|---|---|---|
| | Ratio | ttest | Ratio | ttest | Ratio | ttest | Ratio | ttest |
| M23 | 0.763 | 1.2E−04 | 0.810 | 1.5E−02 | 0.754 | 4.8E−04 | 0.696 | 6.5E−04 |
| M24 | 0.665 | 3.5E−05 | 0.763 | 4.2E−02 | 0.641 | 3.5E−05 | 0.533 | 4.0E−04 |
| M25 | 0.965 | 7.5E−01 | 1.025 | 7.9E−01 | 0.973 | 8.4E−01 | 0.838 | 1.6E−01 |

TABLE 21b

Ratio and T-test Values of Ethanolamine Phospholipid Ratios to M01 Between Males of Various Levels of Dementia

| Metabolite Code | ADAS 20-39 to 5-19, Male | | ADAS 40-70 to 5-19, Male | | ADAS 40-70 to 20-39, Male | |
|---|---|---|---|---|---|---|
| | Ratio | ttest | Ratio | ttest | Ratio | ttest |
| M01 | 1.000 | #DIV/0! | 1.000 | #DIV/0! | 1.000 | #DIV/0! |
| M02 | 0.958 | 5.5E−01 | 0.807 | 7.1E−02 | 0.843 | 3.5E−02 |
| M03 | 0.891 | 4.6E−02 | 0.792 | 6.9E−03 | 0.888 | 9.3E−02 |
| M04 | 1.080 | 4.5E−01 | 0.903 | 4.8E−01 | 0.837 | 1.4E−01 |
| M05 | 0.980 | 7.2E−01 | 0.930 | 3.2E−01 | 0.948 | 4.4E−01 |
| M06 | 1.016 | 8.4E−01 | 1.002 | 9.8E−01 | 0.987 | 8.9E−01 |
| M07 | 0.946 | 5.1E−01 | 0.811 | 8.4E−02 | 0.857 | 1.8E−01 |
| M08 | 0.973 | 7.8E−01 | 0.806 | 1.3E−01 | 0.828 | 1.3E−01 |
| M09 | 0.917 | 4.2E−01 | 0.668 | 1.5E−02 | 0.728 | 3.5E−02 |
| M10 | 0.980 | 6.6E−01 | 0.905 | 1.1E−01 | 0.923 | 1.9E−01 |
| M11 | 0.995 | 9.4E−01 | 0.919 | 4.0E−01 | 0.924 | 3.5E−01 |
| M12 | 0.964 | 5.1E−01 | 0.858 | 5.8E−02 | 0.890 | 1.6E−01 |
| M13 | 0.948 | 3.5E−01 | 0.913 | 2.6E−01 | 0.963 | 6.3E−01 |
| M14 | 0.864 | 1.1E−01 | 0.732 | 4.1E−02 | 0.847 | 1.4E−01 |
| M15 | 0.947 | 2.6E−01 | 0.911 | 1.7E−01 | 0.962 | 5.2E−01 |
| M16 | 0.957 | 5.5E−01 | 0.909 | 3.4E−01 | 0.950 | 5.8E−01 |
| M17 | 0.877 | 1.4E−01 | 0.767 | 6.0E−02 | 0.875 | 2.6E−01 |
| M18 | 0.932 | 4.5E−01 | 0.844 | 1.9E−01 | 0.905 | 3.9E−01 |
| M19 | 0.891 | 2.8E−01 | 0.679 | 2.6E−02 | 0.762 | 4.5E−02 |
| M20 | 0.896 | 8.6E−02 | 0.858 | 9.6E−02 | 0.957 | 5.9E−01 |
| M21 | 0.937 | 4.2E−01 | 0.899 | 3.6E−01 | 0.959 | 6.8E−01 |
| M22 | 0.926 | 3.4E−01 | 0.844 | 1.8E−01 | 0.912 | 4.0E−01 |
| M23 | 0.931 | 3.9E−01 | 0.860 | 1.8E−01 | 0.923 | 4.5E−01 |
| M24 | 0.840 | 1.2E−01 | 0.699 | 5.7E−02 | 0.832 | 1.5E−01 |
| M25 | 0.949 | 6.7E−01 | 0.818 | 1.3E−01 | 0.862 | 4.4E−01 |

TABLE 22

Effect of Pathology State on Ethanolamine Phospholipid Ratios to M01 in Males

| Metabolite Code | Post Mortem Ctl, Male | | Post Mortem SDAT Male | | SDAT vs Control | |
|---|---|---|---|---|---|---|
| | Mean | SEM | Mean | SEM | Ratio | ttest |
| M01 | 1.000 | 0.000 | 1.000 | 0.000 | 1.000 | #DIV/0! |
| M02 | 0.367 | 0.029 | 0.290 | 0.029 | 0.791 | 0.076 |
| M03 | 0.482 | 0.042 | 0.391 | 0.013 | 0.811 | 0.054 |
| M04 | 0.143 | 0.031 | 0.076 | 0.009 | 0.529 | 0.052 |
| M05 | 0.048 | 0.009 | 0.029 | 0.002 | 0.607 | 0.052 |
| M06 | 0.080 | 0.014 | 0.046 | 0.003 | 0.581 | 0.033 |
| M07 | 0.107 | 0.025 | 0.059 | 0.005 | 0.549 | 0.074 |
| M08 | 0.024 | 0.005 | 0.012 | 0.001 | 0.511 | 0.037 |
| M09 | 0.052 | 0.018 | 0.018 | 0.002 | 0.341 | 0.074 |
| M10 | 0.337 | 0.038 | 0.269 | 0.013 | 0.798 | 0.107 |
| M11 | 0.452 | 0.066 | 0.272 | 0.017 | 0.602 | 0.016 |
| M12 | 0.819 | 0.130 | 0.616 | 0.024 | 0.753 | 0.143 |
| M13 | 0.079 | 0.009 | 0.060 | 0.005 | 0.759 | 0.085 |
| M14 | 0.212 | 0.039 | 0.115 | 0.010 | 0.542 | 0.026 |
| M15 | 0.375 | 0.035 | 0.344 | 0.025 | 0.918 | 0.483 |
| M16 | 0.792 | 0.128 | 0.627 | 0.047 | 0.791 | 0.240 |
| M17 | 0.849 | 0.191 | 0.561 | 0.040 | 0.660 | 0.156 |
| M18 | 0.085 | 0.011 | 0.056 | 0.004 | 0.656 | 0.018 |

TABLE 22-continued

Effect of Pathology State on Ethanolamine Phospholipid Ratios to M01 in Males

| | Post Mortem Ctl, Male | | Post Mortem SDAT Male | | SDAT vs Control | |
|---|---|---|---|---|---|---|
| Metabolite Code | Mean | SEM | Mean | SEM | Ratio | ttest |
| M19 | 0.273 | 0.051 | 0.164 | 0.015 | 0.601 | 0.056 |
| M20 | 0.254 | 0.027 | 0.187 | 0.009 | 0.737 | 0.028 |
| M21 | 0.613 | 0.109 | 0.371 | 0.021 | 0.605 | 0.042 |
| M22 | 1.890 | 0.379 | 1.199 | 0.083 | 0.634 | 0.092 |
| M23 | 0.074 | 0.008 | 0.055 | 0.004 | 0.750 | 0.061 |
| M24 | 0.241 | 0.039 | 0.142 | 0.011 | 0.588 | 0.025 |
| M25 | 2.066 | 0.225 | 2.384 | 0.388 | 1.154 | 0.487 |

TABLE 23

Effect of Dementia State on Ethanolamine Phospholipid Ratios to M01 in Females

| | Cognitive Normal, Female | | SDAT_all, Female | | SDAT, ADAS 5-19, Female | | SDAT, ADAS 23-39, Female | | SDAT, ADAS 40-70, Female | |
|---|---|---|---|---|---|---|---|---|---|---|
| Metabolite Code | Mean | SEM | Mean | SEM | Mean | SEM | Mean | SEM | Mean | SEM |
| M01 | 1.000 | 0.000 | 1.000 | 0.000 | 1.000 | 0.000 | 1.000 | 0.000 | 1.000 | 0.000 |
| M02 | 0.520 | 0.029 | 0.463 | 0.012 | 0.454 | 0.021 | 0.499 | 0.023 | 0.431 | 0.018 |
| M03 | 0.852 | 0.034 | 0.687 | 0.017 | 0.742 | 0.030 | 0.704 | 0.031 | 0.624 | 0.022 |
| M04 | 0.222 | 0.013 | 0.219 | 0.010 | 0.215 | 0.013 | 0.241 | 0.021 | 0.197 | 0.015 |
| M05 | 0.092 | 0.004 | 0.086 | 0.003 | 0.091 | 0.004 | 0.088 | 0.005 | 0.081 | 0.004 |
| M06 | 0.234 | 0.012 | 0.207 | 0.007 | 0.226 | 0.011 | 0.217 | 0.013 | 0.180 | 0.009 |
| M07 | 0.474 | 0.034 | 0.368 | 0.018 | 0.422 | 0.039 | 0.377 | 0.028 | 0.314 | 0.025 |
| M08 | 0.054 | 0.004 | 0.047 | 0.002 | 0.050 | 0.003 | 0.051 | 0.004 | 0.039 | 0.002 |
| M09 | 0.167 | 0.013 | 0.121 | 0.005 | 0.140 | 0.010 | 0.123 | 0.009 | 0.103 | 0.008 |
| M10 | 0.469 | 0.016 | 0.431 | 0.010 | 0.451 | 0.016 | 0.428 | 0.018 | 0.418 | 0.016 |
| M11 | 0.929 | 0.039 | 0.807 | 0.023 | 0.886 | 0.041 | 0.839 | 0.044 | 0.708 | 0.030 |
| M12 | 1.682 | 0.078 | 1.384 | 0.042 | 1.568 | 0.090 | 1.384 | 0.067 | 1.239 | 0.062 |
| M13 | 0.111 | 0.005 | 0.095 | 0.003 | 0.101 | 0.005 | 0.095 | 0.005 | 0.089 | 0.004 |
| M14 | 0.392 | 0.023 | 0.315 | 0.013 | 0.367 | 0.029 | 0.309 | 0.019 | 0.279 | 0.019 |
| M15 | 0.627 | 0.024 | 0.539 | 0.014 | 0.564 | 0.021 | 0.563 | 0.030 | 0.493 | 0.016 |
| M16 | 2.214 | 0.114 | 1.780 | 0.064 | 1.994 | 0.107 | 1.906 | 0.127 | 1.470 | 0.069 |
| M17 | 3.497 | 0.247 | 2.593 | 0.127 | 2.976 | 0.266 | 2.750 | 0.226 | 2.115 | 0.146 |
| M18 | 0.202 | 0.014 | 0.161 | 0.007 | 0.178 | 0.011 | 0.170 | 0.014 | 0.138 | 0.008 |
| M19 | 0.895 | 0.061 | 0.634 | 0.030 | 0.728 | 0.057 | 0.656 | 0.055 | 0.537 | 0.041 |
| M20 | 0.669 | 0.035 | 0.535 | 0.018 | 0.587 | 0.032 | 0.553 | 0.036 | 0.474 | 0.022 |
| M21 | 2.318 | 0.118 | 1.798 | 0.076 | 2.039 | 0.132 | 1.922 | 0.147 | 1.467 | 0.086 |
| M22 | 8.068 | 0.596 | 6.310 | 0.304 | 7.041 | 0.600 | 6.681 | 0.568 | 5.313 | 0.360 |
| M23 | 0.158 | 0.009 | 0.127 | 0.005 | 0.139 | 0.009 | 0.131 | 0.010 | 0.112 | 0.006 |
| M24 | 0.893 | 0.068 | 0.651 | 0.034 | 0.724 | 0.063 | 0.669 | 0.059 | 0.573 | 0.053 |
| M25 | 2.145 | 0.127 | 2.031 | 0.086 | 2.072 | 0.129 | 2.109 | 0.162 | 1.910 | 0.139 |

TABLE 24a

Ratio and T-test values of Ethanolamine Phospholipid Ratios to M01 between females of various levels of dementia

| | AD, All to CN, Female | | ADAS 5-19 to CN, Female | | ADAS 20-39 to CN, Female | | ADAS 40-70 to CN, Female | |
|---|---|---|---|---|---|---|---|---|
| Metabolite Code | Ratio | ttest | Ratio | ttest | Ratio | ttest | Ratio | ttest |
| M01 | 1.000 | #DIV/0! | 1.000 | #DIV/0! | 1.000 | #DIV/0! | 1.000 | #DIV/0! |
| M02 | 0.891 | 4.7E−02 | 0.872 | 6.4E−02 | 0.960 | 5.7E−01 | 0.828 | 7.0E−03 |
| M03 | 0.806 | 1.3E−05 | 0.871 | 1.6E−02 | 0.826 | 2.1E−03 | 0.732 | 6.8E−08 |
| M04 | 0.986 | 8.8E−01 | 0.968 | 7.0E−01 | 1.086 | 4.9E−01 | 0.887 | 2.3E−01 |
| M05 | 0.941 | 3.5E−01 | 0.989 | 8.7E−01 | 0.962 | 6.4E−01 | 0.879 | 5.5E−02 |
| M06 | 0.885 | 6.6E−02 | 0.966 | 6.3E−01 | 0.928 | 3.7E−01 | 0.771 | 2.8E−04 |
| M07 | 0.776 | 6.7E−03 | 0.890 | 3.2E−01 | 0.796 | 3.2E−02 | 0.663 | 2.3E−04 |
| M08 | 0.869 | 1.3E−01 | 0.934 | 4.9E−01 | 0.943 | 6.2E−01 | 0.735 | 1.5E−03 |
| M09 | 0.724 | 3.1E−04 | 0.837 | 1.0E−01 | 0.740 | 5.4E−03 | 0.618 | 4.2E−05 |
| M10 | 0.919 | 7.3E−02 | 0.963 | 4.4E−01 | 0.913 | 1.1E−01 | 0.892 | 3.1E−02 |
| M11 | 0.868 | 1.6E−02 | 0.953 | 4.4E−01 | 0.902 | 1.5E−01 | 0.762 | 2.0E−05 |
| M12 | 0.823 | 1.5E−03 | 0.932 | 3.4E−01 | 0.823 | 5.0E−03 | 0.736 | 2.0E−05 |
| M13 | 0.854 | 6.6E−03 | 0.914 | 1.8E−01 | 0.854 | 3.1E−02 | 0.806 | 9.4E−04 |
| M14 | 0.802 | 5.5E−03 | 0.935 | 4.9E−01 | 0.789 | 6.6E−03 | 0.711 | 2.4E−04 |

TABLE 24a-continued

Ratio and T-test values of Ethanolamine Phospholipid Ratios to M01 between females of various levels of dementia

| | AD, All to CN, Female | | ADAS 5-19 to CN, Female | | ADAS 20-39 to CN, Female | | ADAS 40-70 to CN, Female | |
|---|---|---|---|---|---|---|---|---|
| Metabolite Code | Ratio | ttest | Ratio | ttest | Ratio | ttest | Ratio | ttest |
| M15 | 0.860 | 4.8E−03 | 0.900 | 5.1E−02 | 0.897 | 1.3E−01 | 0.786 | 9.1E−06 |
| M16 | 0.804 | 2.1E−03 | 0.901 | 1.6E−01 | 0.861 | 9.3E−02 | 0.664 | 8.8E−08 |
| M17 | 0.742 | 1.5E−03 | 0.851 | 1.6E−01 | 0.786 | 3.2E−02 | 0.605 | 2.3E−06 |
| M18 | 0.798 | 9.5E−03 | 0.879 | 1.8E−01 | 0.844 | 1.4E−01 | 0.683 | 6.3E−05 |
| M19 | 0.709 | 1.6E−04 | 0.813 | 5.1E−02 | 0.733 | 5.3E−03 | 0.600 | 3.2E−06 |
| M20 | 0.800 | 1.0E−03 | 0.878 | 8.7E−02 | 0.826 | 2.8E−02 | 0.709 | 3.4E−06 |
| M21 | 0.776 | 1.4E−03 | 0.879 | 1.2E−01 | 0.829 | 5.6E−02 | 0.633 | 5.4E−08 |
| M22 | 0.782 | 9.6E−03 | 0.873 | 2.3E−01 | 0.828 | 1.1E−01 | 0.659 | 7.8E−05 |
| M23 | 0.801 | 5.3E−03 | 0.877 | 1.3E−01 | 0.831 | 6.8E−02 | 0.707 | 4.5E−05 |
| M24 | 0.729 | 1.6E−03 | 0.811 | 7.2E−02 | 0.750 | 1.7E−02 | 0.642 | 3.3E−04 |
| M25 | 0.947 | 5.3E−01 | 0.966 | 6.9E−01 | 0.983 | 8.7E−01 | 0.890 | 2.3E−01 |

TABLE 24b

Ratio and T-test values of Ethanolamine Phospholipid Ratios to M01 between females of various levels of dementia

| | ADAS 20-39 to 5-19, Female | | ADAS 40-70 to 5-19, Female | | ADAS 40-70 to 20-39, Female | |
|---|---|---|---|---|---|---|
| Metabolite Code | Ratio | ttest | Ratio | ttest | Ratio | ttest |
| M01 | 1.000 | #DIV/0! | 1.000 | #DIV/0! | 1.000 | #DIV/0! |
| M02 | 1.101 | 1.6E−01 | 0.949 | 4.1E−01 | 0.862 | 2.2E−02 |
| M03 | 0.949 | 4.0E−01 | 0.841 | 1.5E−03 | 0.887 | 4.2E−02 |
| M04 | 1.122 | 3.3E−01 | 0.917 | 3.8E−01 | 0.817 | 9.2E−02 |
| M05 | 0.972 | 7.3E−01 | 0.889 | 7.6E−02 | 0.914 | 2.6E−01 |
| M06 | 0.961 | 6.3E−01 | 0.797 | 1.3E−03 | 0.830 | 2.4E−02 |
| M07 | 0.895 | 3.4E−01 | 0.745 | 1.7E−02 | 0.833 | 9.8E−02 |
| M08 | 1.010 | 9.4E−01 | 0.787 | 1.1E−02 | 0.780 | 3.5E−02 |
| M09 | 0.884 | 2.4E−01 | 0.738 | 6.7E−03 | 0.835 | 1.0E−01 |
| M10 | 0.948 | 3.5E−01 | 0.926 | 1.5E−01 | 0.977 | 6.8E−01 |
| M11 | 0.947 | 4.6E−01 | 0.799 | 6.4E−04 | 0.844 | 1.9E−02 |
| M12 | 0.883 | 9.7E−02 | 0.790 | 2.5E−03 | 0.895 | 1.2E−01 |
| M13 | 0.934 | 3.6E−01 | 0.882 | 5.3E−02 | 0.944 | 4.1E−01 |
| M14 | 0.844 | 8.6E−02 | 0.761 | 9.9E−03 | 0.902 | 2.6E−01 |
| M15 | 0.998 | 9.7E−01 | 0.874 | 7.7E−03 | 0.876 | 5.3E−02 |
| M16 | 0.956 | 6.2E−01 | 0.737 | 5.0E−05 | 0.771 | 4.2E−03 |
| M17 | 0.924 | 5.2E−01 | 0.711 | 3.6E−03 | 0.769 | 2.4E−02 |
| M18 | 0.960 | 7.2E−01 | 0.777 | 4.1E−03 | 0.809 | 5.7E−02 |
| M19 | 0.901 | 3.8E−01 | 0.738 | 7.1E−03 | 0.819 | 9.2E−02 |
| M20 | 0.941 | 4.9E−01 | 0.808 | 3.7E−03 | 0.858 | 7.3E−02 |
| M21 | 0.943 | 5.8E−01 | 0.720 | 3.1E−04 | 0.763 | 1.1E−02 |
| M22 | 0.949 | 6.7E−01 | 0.755 | 1.2E−02 | 0.795 | 5.1E−02 |
| M23 | 0.948 | 6.1E−01 | 0.806 | 1.4E−02 | 0.851 | 1.1E−01 |
| M24 | 0.925 | 5.4E−01 | 0.791 | 6.9E−02 | 0.856 | 2.3E−01 |
| M25 | 1.018 | 8.7E−01 | 0.922 | 4.0E−01 | 0.906 | 3.6E−01 |

TABLE 25

Effect of Pathology State on Ethanolamine Phospholipid Ratios to M01 in Females

| | Post Mortem Ctl, Female | | Post Mortem SDAT Female | | Autopsy AD vs. Control, Female | |
|---|---|---|---|---|---|---|
| Metabolite Code | Mean | SEM | Mean | SEM | Ratio | ttest |
| M01 | 1.000 | 0.000 | 1.000 | 0.000 | 1.000 | #DIV/0! |
| M02 | 0.322 | 0.028 | 0.367 | 0.047 | 1.140 | 0.440 |
| M03 | 0.400 | 0.022 | 0.361 | 0.023 | 0.902 | 0.237 |
| M04 | 0.086 | 0.012 | 0.092 | 0.019 | 1.069 | 0.798 |
| M05 | 0.040 | 0.003 | 0.032 | 0.005 | 0.809 | 0.225 |
| M06 | 0.069 | 0.008 | 0.059 | 0.017 | 0.855 | 0.605 |
| M07 | 0.102 | 0.016 | 0.077 | 0.013 | 0.752 | 0.242 |
| M08 | 0.017 | 0.002 | 0.017 | 0.002 | 0.981 | 0.922 |
| M09 | 0.033 | 0.005 | 0.024 | 0.003 | 0.725 | 0.133 |
| M10 | 0.290 | 0.025 | 0.291 | 0.027 | 1.003 | 0.981 |

TABLE 25-continued

Effect of Pathology State on Ethanolamine Phospholipid Ratios to M01 in Females

| | Post Mortem Ctl, Female | | Post Mortem SDAT Female | | Autopsy AD vs. Control, Female | |
|---|---|---|---|---|---|---|
| Metabolite Code | Mean | SEM | Mean | SEM | Ratio | ttest |
| M11 | 0.384 | 0.044 | 0.364 | 0.057 | 0.950 | 0.797 |
| M12 | 0.731 | 0.096 | 0.699 | 0.059 | 0.957 | 0.777 |
| M13 | 0.061 | 0.008 | 0.069 | 0.007 | 1.122 | 0.489 |
| M14 | 0.144 | 0.015 | 0.155 | 0.033 | 1.071 | 0.791 |
| M15 | 0.339 | 0.021 | 0.301 | 0.027 | 0.889 | 0.297 |
| M16 | 0.670 | 0.066 | 0.599 | 0.112 | 0.895 | 0.605 |
| M17 | 0.697 | 0.063 | 0.591 | 0.082 | 0.848 | 0.329 |
| M18 | 0.081 | 0.014 | 0.069 | 0.008 | 0.854 | 0.462 |
| M19 | 0.211 | 0.017 | 0.180 | 0.018 | 0.853 | 0.230 |
| M20 | 0.283 | 0.025 | 0.193 | 0.032 | 0.680 | 0.042 |
| M21 | 0.624 | 0.079 | 0.421 | 0.127 | 0.674 | 0.203 |
| M22 | 1.782 | 0.251 | 1.480 | 0.225 | 0.831 | 0.382 |
| M23 | 0.073 | 0.011 | 0.060 | 0.006 | 0.816 | 0.275 |
| M24 | 0.214 | 0.018 | 0.149 | 0.016 | 0.697 | 0.016 |
| M25 | 1.382 | 0.214 | 1.767 | 0.221 | 1.279 | 0.229 |

TABLE 26

Effect of Age on Ethanolamine Phospholipid Ratios to M01 in Males

| | Age Ctl, 30-39, Male | | Age Ctl, 40-49, Male | | Age Ctl, 50-59, Male | | Age Ctl, 60-69, Male | | Age Ctl, 70+ Male | |
|---|---|---|---|---|---|---|---|---|---|---|
| Metabolite Code | Mean | SEM | Mean | SEM | Mean | SEM | Mean | SEM | Mean | SEM |
| M01 | 1.000 | 0.000 | 1.000 | 0.000 | 1.000 | 0.000 | 1.000 | 0.000 | 1.000 | 0.000 |
| M02 | 0.476 | 0.042 | 0.477 | 0.034 | 0.517 | 0.027 | 0.431 | 0.031 | 0.420 | 0.028 |
| M03 | 0.863 | 0.063 | 0.751 | 0.049 | 0.864 | 0.030 | 0.792 | 0.051 | 0.848 | 0.071 |
| M04 | 0.224 | 0.025 | 0.229 | 0.026 | 0.235 | 0.013 | 0.203 | 0.019 | 0.204 | 0.017 |
| M05 | 0.113 | 0.008 | 0.102 | 0.007 | 0.101 | 0.004 | 0.091 | 0.005 | 0.088 | 0.005 |
| M06 | 0.263 | 0.029 | 0.234 | 0.021 | 0.243 | 0.012 | 0.199 | 0.016 | 0.210 | 0.012 |
| M07 | 0.683 | 0.136 | 0.493 | 0.070 | 0.581 | 0.041 | 0.479 | 0.052 | 0.457 | 0.039 |
| M08 | 0.079 | 0.010 | 0.064 | 0.007 | 0.067 | 0.004 | 0.054 | 0.005 | 0.049 | 0.004 |
| M09 | 0.161 | 0.025 | 0.124 | 0.017 | 0.173 | 0.013 | 0.154 | 0.018 | 0.172 | 0.024 |
| M10 | 0.464 | 0.025 | 0.454 | 0.022 | 0.445 | 0.012 | 0.419 | 0.018 | 0.407 | 0.016 |
| M11 | 1.063 | 0.111 | 0.899 | 0.069 | 0.908 | 0.037 | 0.789 | 0.052 | 0.811 | 0.038 |
| M12 | 2.068 | 0.251 | 1.728 | 0.168 | 1.942 | 0.099 | 1.664 | 0.111 | 1.552 | 0.087 |
| M13 | 0.126 | 0.009 | 0.117 | 0.009 | 0.121 | 0.005 | 0.102 | 0.006 | 0.092 | 0.005 |
| M14 | 0.294 | 0.033 | 0.242 | 0.029 | 0.332 | 0.020 | 0.316 | 0.029 | 0.363 | 0.041 |
| M15 | 0.699 | 0.034 | 0.658 | 0.041 | 0.675 | 0.023 | 0.567 | 0.031 | 0.590 | 0.029 |
| M16 | 2.429 | 0.285 | 2.020 | 0.175 | 2.284 | 0.118 | 1.778 | 0.145 | 1.922 | 0.112 |
| M17 | 4.127 | 0.757 | 3.164 | 0.418 | 3.980 | 0.257 | 3.167 | 0.320 | 3.178 | 0.294 |
| M18 | 0.258 | 0.025 | 0.229 | 0.025 | 0.244 | 0.014 | 0.195 | 0.021 | 0.174 | 0.014 |
| M19 | 0.725 | 0.101 | 0.607 | 0.094 | 0.865 | 0.063 | 0.769 | 0.085 | 0.881 | 0.131 |
| M20 | 0.691 | 0.049 | 0.616 | 0.043 | 0.619 | 0.030 | 0.529 | 0.034 | 0.553 | 0.034 |
| M21 | 2.395 | 0.215 | 2.163 | 0.189 | 2.287 | 0.122 | 1.773 | 0.148 | 1.840 | 0.108 |
| M22 | 8.811 | 1.529 | 7.346 | 0.883 | 8.537 | 0.549 | 7.124 | 0.644 | 6.920 | 0.635 |
| M23 | 0.189 | 0.019 | 0.175 | 0.016 | 0.178 | 0.009 | 0.150 | 0.016 | 0.133 | 0.008 |
| M24 | 0.649 | 0.086 | 0.606 | 0.098 | 0.787 | 0.057 | 0.700 | 0.072 | 0.799 | 0.122 |
| M25 | 2.182 | 0.444 | 1.975 | 0.265 | 2.747 | 0.211 | 2.608 | 0.251 | 3.066 | 0.284 |

TABLE 27

Ratio and T-test values of Ethanolamine Phospholipid
Ratios to M01 between males of different ages

| | 50-59 vs. 40-49, Male | | 60-69 vs. 40-49, Male | | 70+ vs. 40-49, Male | |
|---|---|---|---|---|---|---|
| Metabolite Code | Ratio | ttest | Ratio | ttest | Ratio | ttest |
| M01 | 1.000 | #DIV/0! | 1.000 | #DIV/0! | 1.000 | #DIV/0! |
| M02 | 1.082 | 3.9E−01 | 0.903 | 3.2E−01 | 0.879 | 1.9E−01 |
| M03 | 1.149 | 4.5E−02 | 1.054 | 5.8E−01 | 1.128 | 3.0E−01 |
| M04 | 1.023 | 8.4E−01 | 0.883 | 4.0E−01 | 0.889 | 3.9E−01 |
| M05 | 0.984 | 8.3E−01 | 0.884 | 1.6E−01 | 0.863 | 8.5E−02 |
| M06 | 1.041 | 6.8E−01 | 0.851 | 1.9E−01 | 0.898 | 3.1E−01 |

TABLE 27-continued

Ratio and T-test values of Ethanolamine Phospholipid
Ratios to M01 between males of different ages

| | 50-59 vs. 40-49, Male | | 60-69 vs. 40-49, Male | | 70+ vs. 40-49, Male | |
|---|---|---|---|---|---|---|
| Metabolite Code | Ratio | ttest | Ratio | ttest | Ratio | ttest |
| M07 | 1.177 | 2.6E−01 | 0.970 | 8.6E−01 | 0.927 | 6.4E−01 |
| M08 | 1.053 | 6.7E−01 | 0.847 | 2.6E−01 | 0.765 | 5.4E−02 |
| M09 | 1.404 | 2.5E−02 | 1.243 | 2.4E−01 | 1.391 | 1.3E−01 |
| M10 | 0.981 | 7.1E−01 | 0.924 | 2.3E−01 | 0.896 | 7.6E−02 |
| M11 | 1.010 | 9.0E−01 | 0.878 | 2.0E−01 | 0.903 | 2.5E−01 |
| M12 | 1.124 | 2.5E−01 | 0.963 | 7.4E−01 | 0.898 | 3.3E−01 |
| M13 | 1.035 | 6.7E−01 | 0.873 | 1.7E−01 | 0.787 | 1.3E−02 |
| M14 | 1.372 | 1.2E−02 | 1.306 | 7.7E−02 | 1.500 | 2.7E−02 |
| M15 | 1.026 | 7.0E−01 | 0.862 | 7.8E−02 | 0.896 | 1.7E−01 |
| M16 | 1.131 | 2.1E−01 | 0.880 | 2.9E−01 | 0.951 | 6.2E−01 |
| M17 | 1.258 | 8.8E−02 | 1.001 | 1.0E+00 | 1.004 | 9.8E−01 |
| M18 | 1.067 | 5.6E−01 | 0.851 | 3.0E−01 | 0.761 | 4.9E−02 |
| M19 | 1.426 | 2.4E−02 | 1.266 | 2.1E−01 | 1.451 | 1.1E−01 |
| M20 | 1.004 | 9.6E−01 | 0.858 | 1.1E−01 | 0.898 | 2.5E−01 |
| M21 | 1.057 | 5.8E−01 | 0.820 | 1.0E−01 | 0.851 | 1.2E−01 |
| M22 | 1.162 | 2.4E−01 | 0.970 | 8.4E−01 | 0.942 | 6.9E−01 |
| M23 | 1.016 | 8.7E−01 | 0.858 | 2.8E−01 | 0.759 | 1.5E−02 |
| M24 | 1.300 | 9.4E−02 | 1.156 | 4.3E−01 | 1.319 | 2.4E−01 |
| M25 | 1.391 | 3.5E−02 | 1.321 | 9.0E−02 | 1.553 | 8.2E−03 |

TABLE 28

Effect of Age on Ethanolamine Phospholipid Ratios to M01 in Females

| | Age Ctl, 30-39, Female | | Age Ctl, 40-49, Female | | Age Ctl, 50-59, Female | | Age Ctl, 60-69, Female | | Age Ctl, 70+ Female | |
|---|---|---|---|---|---|---|---|---|---|---|
| Metabolite Code | Mean | SEM | Mean | SEM | Mean | SEM | Mean | SEM | Mean | SEM |
| M01 | 1.000 | 0.000 | 1.000 | 0.000 | 1.000 | 0.000 | 1.000 | 0.000 | 1.000 | 0.000 |
| M02 | 0.474 | 0.037 | 0.597 | 0.028 | 0.551 | 0.020 | 0.460 | 0.018 | 0.455 | 0.023 |
| M03 | 0.931 | 0.089 | 0.911 | 0.043 | 0.926 | 0.030 | 0.750 | 0.034 | 0.838 | 0.048 |
| M04 | 0.279 | 0.036 | 0.283 | 0.017 | 0.241 | 0.011 | 0.184 | 0.010 | 0.221 | 0.020 |
| M05 | 0.112 | 0.009 | 0.118 | 0.006 | 0.105 | 0.003 | 0.085 | 0.005 | 0.089 | 0.006 |
| M06 | 0.311 | 0.044 | 0.291 | 0.019 | 0.261 | 0.010 | 0.193 | 0.012 | 0.213 | 0.017 |
| M07 | 0.618 | 0.090 | 0.667 | 0.056 | 0.582 | 0.030 | 0.435 | 0.039 | 0.430 | 0.041 |
| M08 | 0.079 | 0.008 | 0.089 | 0.007 | 0.070 | 0.003 | 0.047 | 0.004 | 0.052 | 0.007 |
| M09 | 0.204 | 0.036 | 0.194 | 0.017 | 0.197 | 0.011 | 0.139 | 0.012 | 0.163 | 0.015 |
| M10 | 0.491 | 0.027 | 0.535 | 0.024 | 0.490 | 0.010 | 0.424 | 0.015 | 0.422 | 0.022 |
| M11 | 1.220 | 0.159 | 1.092 | 0.060 | 1.021 | 0.031 | 0.823 | 0.037 | 0.840 | 0.058 |
| M12 | 1.979 | 0.150 | 2.044 | 0.117 | 1.952 | 0.063 | 1.534 | 0.086 | 1.564 | 0.100 |
| M13 | 0.129 | 0.008 | 0.136 | 0.007 | 0.122 | 0.004 | 0.092 | 0.005 | 0.104 | 0.010 |
| M14 | 0.379 | 0.047 | 0.381 | 0.024 | 0.414 | 0.018 | 0.333 | 0.021 | 0.412 | 0.033 |
| M15 | 0.706 | 0.044 | 0.720 | 0.034 | 0.699 | 0.019 | 0.560 | 0.024 | 0.578 | 0.033 |
| M16 | 2.739 | 0.333 | 2.483 | 0.161 | 2.345 | 0.091 | 1.783 | 0.096 | 1.964 | 0.136 |
| M17 | 4.055 | 0.499 | 4.149 | 0.401 | 3.987 | 0.209 | 2.963 | 0.275 | 3.010 | 0.268 |
| M18 | 0.282 | 0.022 | 0.289 | 0.022 | 0.245 | 0.010 | 0.160 | 0.012 | 0.191 | 0.024 |
| M19 | 1.009 | 0.175 | 0.902 | 0.085 | 0.974 | 0.056 | 0.716 | 0.061 | 0.877 | 0.077 |
| M20 | 0.708 | 0.059 | 0.682 | 0.045 | 0.637 | 0.021 | 0.524 | 0.029 | 0.565 | 0.039 |
| M21 | 2.885 | 0.411 | 2.537 | 0.187 | 2.331 | 0.092 | 1.757 | 0.105 | 1.935 | 0.158 |
| M22 | 8.971 | 0.932 | 9.244 | 0.790 | 8.625 | 0.450 | 6.263 | 0.484 | 6.923 | 0.683 |
| M23 | 0.198 | 0.011 | 0.202 | 0.014 | 0.177 | 0.006 | 0.124 | 0.008 | 0.140 | 0.014 |
| M24 | 0.955 | 0.174 | 0.834 | 0.078 | 0.882 | 0.049 | 0.661 | 0.054 | 0.814 | 0.071 |
| M25 | 2.505 | 0.217 | 2.286 | 0.164 | 3.219 | 0.181 | 2.995 | 0.239 | 3.280 | 0.248 |

TABLE 29

Ratio and T-test values of Ethanolamine Phospholipid
Ratios to M01 between females of different ages

| | 50-59 vs. 40-49, Female | | 60-69 vs. 40-49, Female | | 70+ vs. 40-49, Female | |
|---|---|---|---|---|---|---|
| Metabolite Code | Ratio | ttest | Ratio | ttest | Ratio | ttest |
| M01 | 1.000 | #DIV/0! | 1.000 | #DIV/0! | 1.000 | #DIV/0! |
| M02 | 0.923 | 2.1E−01 | 0.771 | 5.7E−05 | 0.763 | 8.4E−04 |
| M03 | 1.017 | 7.8E−01 | 0.823 | 3.7E−03 | 0.920 | 2.8E−01 |
| M04 | 0.850 | 3.5E−02 | 0.652 | 1.1E−06 | 0.782 | 2.3E−02 |
| M05 | 0.892 | 4.7E−02 | 0.721 | 5.0E−05 | 0.758 | 3.7E−03 |

TABLE 29-continued

Ratio and T-test values of Ethanolamine Phospholipid Ratios to M01 between females of different ages

| Metabolite Code | 50-59 vs. 40-49, Female | | 60-69 vs. 40-49, Female | | 70+ vs. 40-49, Female | |
| --- | --- | --- | --- | --- | --- | --- |
| | Ratio | ttest | Ratio | ttest | Ratio | ttest |
| M06 | 0.896 | 1.3E−01 | 0.662 | 1.3E−05 | 0.733 | 6.5E−03 |
| M07 | 0.873 | 1.5E−01 | 0.652 | 7.2E−04 | 0.644 | 3.5E−03 |
| M08 | 0.783 | 4.7E−03 | 0.533 | 6.9E−07 | 0.583 | 9.9E−04 |
| M09 | 1.016 | 8.8E−01 | 0.717 | 7.8E−03 | 0.841 | 2.2E−01 |
| M10 | 0.917 | 4.8E−02 | 0.792 | 7.9E−05 | 0.789 | 2.0E−03 |
| M11 | 0.935 | 2.5E−01 | 0.754 | 1.3E−04 | 0.770 | 5.9E−03 |
| M12 | 0.955 | 4.6E−01 | 0.751 | 5.1E−04 | 0.765 | 5.8E−03 |
| M13 | 0.900 | 7.0E−02 | 0.680 | 4.8E−06 | 0.764 | 9.1E−03 |
| M14 | 1.088 | 3.1E−01 | 0.876 | 1.4E−01 | 1.083 | 4.3E−01 |
| M15 | 0.970 | 5.6E−01 | 0.778 | 1.8E−04 | 0.802 | 6.7E−03 |
| M16 | 0.944 | 4.3E−01 | 0.718 | 1.8E−04 | 0.791 | 2.8E−02 |
| M17 | 0.961 | 7.0E−01 | 0.714 | 1.4E−02 | 0.726 | 4.4E−02 |
| M18 | 0.847 | 4.1E−02 | 0.552 | 6.0E−07 | 0.660 | 5.6E−03 |
| M19 | 1.079 | 4.9E−01 | 0.794 | 7.2E−02 | 0.972 | 8.4E−01 |
| M20 | 0.935 | 3.1E−01 | 0.769 | 2.9E−03 | 0.828 | 7.5E−02 |
| M21 | 0.919 | 2.7E−01 | 0.693 | 2.4E−04 | 0.763 | 2.9E−02 |
| M22 | 0.933 | 4.8E−01 | 0.678 | 1.2E−03 | 0.749 | 4.6E−02 |
| M23 | 0.876 | 5.5E−02 | 0.614 | 1.3E−06 | 0.696 | 3.9E−03 |
| M24 | 1.058 | 6.0E−01 | 0.793 | 6.5E−02 | 0.976 | 8.6E−01 |
| M25 | 1.408 | 2.4E−03 | 1.310 | 2.2E−02 | 1.435 | 8.6E−04 |

TABLE 30

Summary of key ratio and p-value statistics for EtnPls 16:0/22:6 (M19) to PtdEt 16:0/18:0 (M01) serum ratio for males and females combined.

| Comparison | Ratio | T-test |
| --- | --- | --- |
| 60-69 to 50-59 | 0.75 | 1.2E−02 |
| 70-95 to 50-59 | 0.95 | 6.4E−01 |
| CN to 50-59 | 1.07 | 4.8E−01 |
| SDAT to 50-59 | 0.70 | 4.7E−07 |
| 70-95 to 60-69 | 1.26 | 6.9E−02 |
| CN to 60-69 | 1.42 | 3.8E−04 |
| SDAT to 70-95 | 0.74 | 1.3E−04 |
| SDAT to CN | 0.65 | 7.6E−11 |
| ADAS 5-19 to CN | 0.74 | 3.0E−04 |
| ADAS 20-39 to CN | 0.66 | 1.3E−07 |
| ADAS 40-70 to CN | 0.53 | 3.9E−11 |
| ADAS 20-39 to ADAS 5-19 | 0.90 | 1.6E−01 |
| ADAS 40-70 to ADAS 5-19 | 0.72 | 3.4E−04 |
| ADAS 40-70 to ADAS 20-39 | 0.80 | 1.0E−02 |
| Post-Mortem SDAT to Control* | 0.55 | 4.7E−03 |

*ratio and p-value of EtnPls 16:0/22:6 alone.

The invention claimed is:

1. A method of lowering cholesterol in a patient in need thereof by administering to said patient a therapeutic effective amount of a compound selected from the group consisting of: 1-alkyl, 2-acyl-glyceraldehyde-3-phosphate (G3P); 1-alkyl, 2-acyl-glycerol; and 1-alkyl, 2-acyl-glycerylphosphatidylethanolamine (GPE);

or a pharmaceutically acceptable salt thereof.

2. The method of claim 1, wherein the compound is a 1-alkyl, 2-acyl-glycerol.

3. The method of claim 1, wherein the sidechains include a saturated or unsaturated fatty acid of the following type:

16:0, 18:0, 18:1, 18:2, or 18:3 as alkyl at the sn-1 position, and/or

16:0, 18:0, 18:1, 18:2, 18:3, 20:4, 20:5, 20:6, 22:4, 22:5, 22:6, 24:4, 24:5, or 24:6 as acyl at the sn-2 position.

* * * * *